US010067143B2

(12) United States Patent
Clark

(10) Patent No.: US 10,067,143 B2
(45) Date of Patent: *Sep. 4, 2018

(54) UBIQUITINATION ASSAY

(75) Inventor: Jonathan Peter Clark, Kelty (GB)

(73) Assignee: ITI Scotland Limited, Glasgow (GB)

( * ) Notice: Subject to any disclaimer, the term of this patent is extended or adjusted under 35 U.S.C. 154(b) by 510 days.

This patent is subject to a terminal disclaimer.

(21) Appl. No.: 13/695,271

(22) PCT Filed: Apr. 28, 2011

(86) PCT No.: PCT/GB2011/000656
§ 371 (c)(1),
(2), (4) Date: Jan. 9, 2013

(87) PCT Pub. No.: WO2011/135301
PCT Pub. Date: Nov. 3, 2011

(65) Prior Publication Data
US 2013/0116152 A1 May 9, 2013

(30) Foreign Application Priority Data
Apr. 29, 2010 (GB) .................................. 1007182.7

(51) Int. Cl.
G01N 33/68 (2006.01)
C12Q 1/37 (2006.01)
G01N 33/542 (2006.01)

(52) U.S. Cl.
CPC ........... *G01N 33/6872* (2013.01); *C12Q 1/37* (2013.01); *G01N 33/542* (2013.01); *G01N 33/6842* (2013.01); *G01N 33/6845* (2013.01); *G01N 2500/00* (2013.01)

(58) Field of Classification Search
CPC ........... G01N 33/68; G01N 2333/9015; G01N 33/6872; G01N 33/542; G01N 33/6842; G01N 2500/00; C12Q 1/25; C12Q 1/37
See application file for complete search history.

(56) References Cited

U.S. PATENT DOCUMENTS

| 6,413,725 | B1 | 7/2002 | Deshaies et al. |
| 2003/0207290 | A1 | 11/2003 | Kenten et al. |
| 2005/0032139 | A1* | 2/2005 | Issakani ................. C12Q 1/25 435/7.92 |
| 2006/0105409 | A1 | 5/2006 | Issakani et al. |
| 2006/0194262 | A1 | 8/2006 | Xu et al. |
| 2006/0276520 | A1 | 12/2006 | Singh et al. |
| 2013/0115619 | A1 | 5/2013 | Clark |

FOREIGN PATENT DOCUMENTS

| EP | 1268847 | 1/2003 |
| EP | 1767649 | 3/2007 |
| GB | 1006604.1 | 4/2010 |
| WO | WO 2006/044747 A2 | 4/2006 |
| WO | WO 2006/077407 A2 | 7/2006 |
| WO | WO 2011/131934 | 10/2011 |
| WO | 2011135301 A1 | 11/2011 |
| WO | WO 2011/135302 | 11/2011 |
| WO | WO 2011/135303 | 11/2011 |

OTHER PUBLICATIONS

Sasiela et al., J Biomol Screen, 13 (3); 2008.*
Weissman, Nature Reviews, 2:169-178, 2001.*
Radke et al., Oncogene (2005) 24, 3448-3458.*
IHOP Accession No. Search Results for X56976. www.ihop-net.org/.*
IHOP Accession No. Search Results for P22314. www.ihop-net.org/.*
IHOP Accession No. Search Results for M58028. www.ihop-net.org/.*
PCT International Search Report and Written Opinion for PCT/GB2011/000656, dated Sep. 12, 2011, 14 Pages.
Deshaies, R., et al., "Ring Domain E3 Ubiquitin Ligases," Annual Review of Biochemistry, Jun. 1, 2009, pp. 399-434, vol. 78, No. 1.
Haas, A., et al., "Pathways of ubiquitin conjugation," FASEB Journal, Dec. pp. 1257-1268, vol. 11, 1997.
Hicke, L., et al., "Ubiquitin-Binding Domains," Nature, Aug. 2005, pp. 610-621, vol. 6.
Kipreos, E., et al., "The F-box protein family," Genome Biology, Nov. 10, 2000, pp. 3002.1-3002.7 vol. 1, No. 5.
Xu, S., et al., "Substrate Recognition and Ubiquitination of SCFSkp2/Cks1 Uqbiquitin-Protein Isopeptide Ligase," Journal of Biological Chemistry, Jan. 1, 2007, pp. 15462-15470, vol. 282, No. 21.
U.S. Appl. No. 13/695,263 , "Advisory Action", dated Oct. 31, 2016, 4 pages.
U.S. Appl. No. 13/695,263 , "Final Office Action", dated Jul. 22, 2016, 13 pages.
U.S. Appl. No. 13/695,263 , "Non-Final Office Action", dated Dec. 2, 2015, 11 pages.
U.S. Appl. No. 13/695,263 , "Non-Final Office Action", dated Jul. 12, 2017, 15 pages.
U.S. Appl. No. 13/695,263 , "Notice of Allowance", dated Mar. 19, 2018, 8 pages.
U.S. Appl. No. 13/695,263 , "Restriction Requirement", dated Apr. 17, 2015, 8 pages.
PCT/GB2011/000657 , "International Search Report and Written Opinion", dated Sep. 15, 2011, 18 pages.
Xu et al., "In Vitro SCFβ-Trcp1-Mediated IκBα Ubiquitination Assay for High-Throughput Screen", Methods in Enzymology, vol. 399, Jan. 2005, pp. 729-740.

* cited by examiner

*Primary Examiner* — Andrea S Grossman
(74) *Attorney, Agent, or Firm* — Kilpatrick Townsend & Stockton LLP

(57) ABSTRACT

The present application relates to a method of assaying ubiquitination in a sample by combining ubiquitin together with a substrate in a sample containing UBE1, UbcH3, Skp2-isoform 1, Skp1, Cul1, Rbx1, Cks1, CDK2 and Cyclin E1 under conditions suitable for ubiquitination to take place, exposing the sample to a labelled binding partner which is specific for the ubiquitin, and measuring the amount of ubiquitin bound to the substrate.

20 Claims, 46 Drawing Sheets

Specification includes a Sequence Listing.

Figure 1

| Complex | Protein | Manufacturing Name | Expression System | Accession Number |
|---|---|---|---|---|
| SCF complex | Skp1 | 6His-Skp1-(hu,FL) | BEVS | NM_170679 |
| | Skp2 | GST-Skp2-(hu,FL) | BEVS | NM_032637 |
| | Cul1 | 6His-Cul1-(hu,FL) | BEVS | NM_003592 |
| | Rbx1 | UT-Rbx1-(hu,FL) | BEVS | NM_014248 |
| CDK | CDK2 | UT-CDK2-(hu,FL) | BEVS | NM_001798 |
| | Cyclin E | 6His-Cyclin E-(hu,FL) | BEVS | NM_001238 |
| | p27 (x3) | FLAG/cMyc/HA-p27-(hu,FL) | BEVS | BC001971 |
| Accessory | Cks1 | 6His (C-term)-Cks1-(hu,FL) | E coli | NM_001826 |
| | | GST-Cks1-(hu,FL) | E coli | NM_001826 |
| E2 | UbcH3 (x3) | FLAG/cMyc/HA,6His-UbcH3-(hu,FL) | E coli | NM_004359 |
| E1 | UBE1 | 6His-UBE1-(hu,FL) | BEVS | NM_003334 |

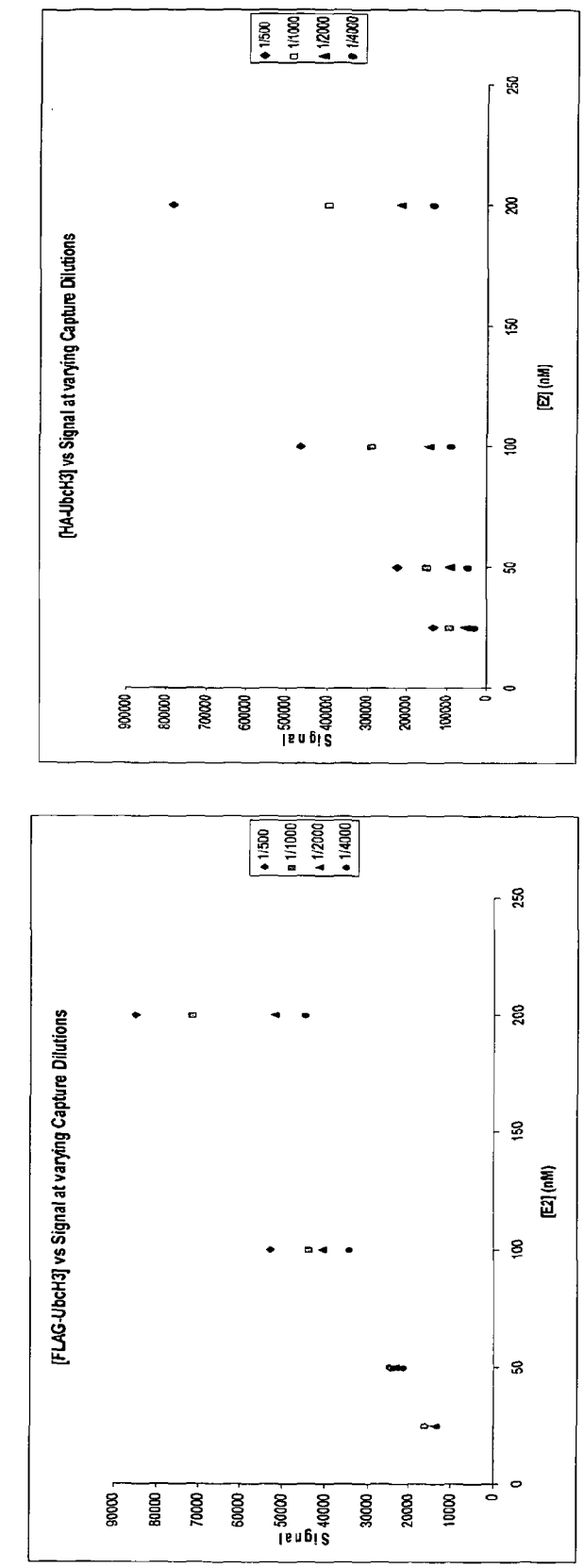
Figure 12 (a) cont.

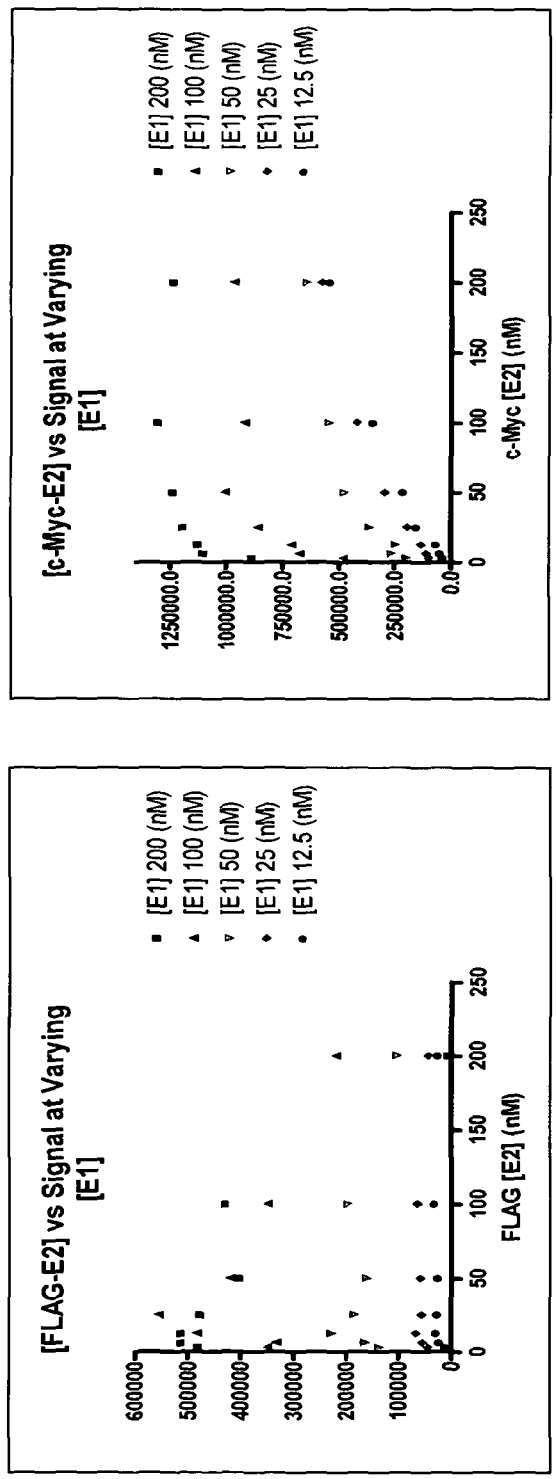
Figure 12 (b) cont.

Figure 14 (b)
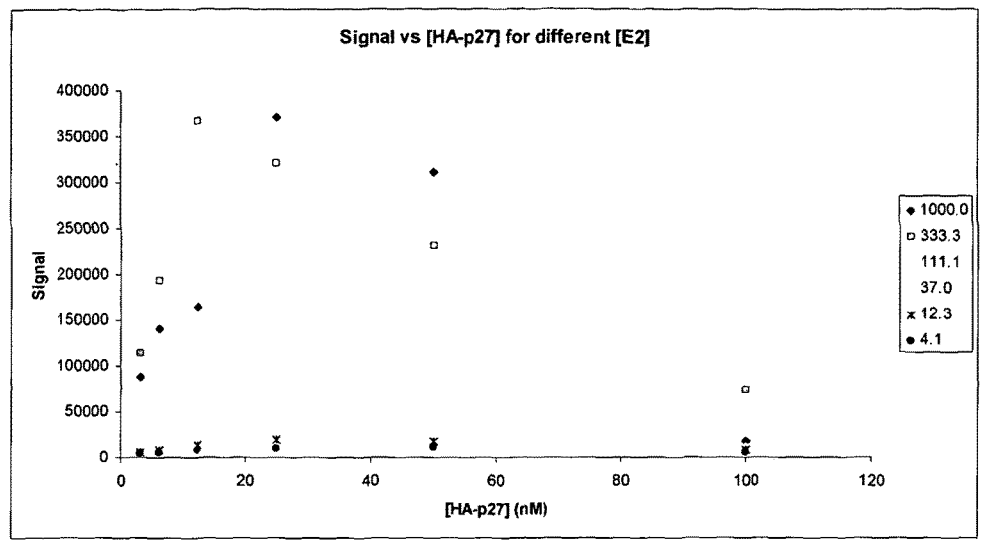
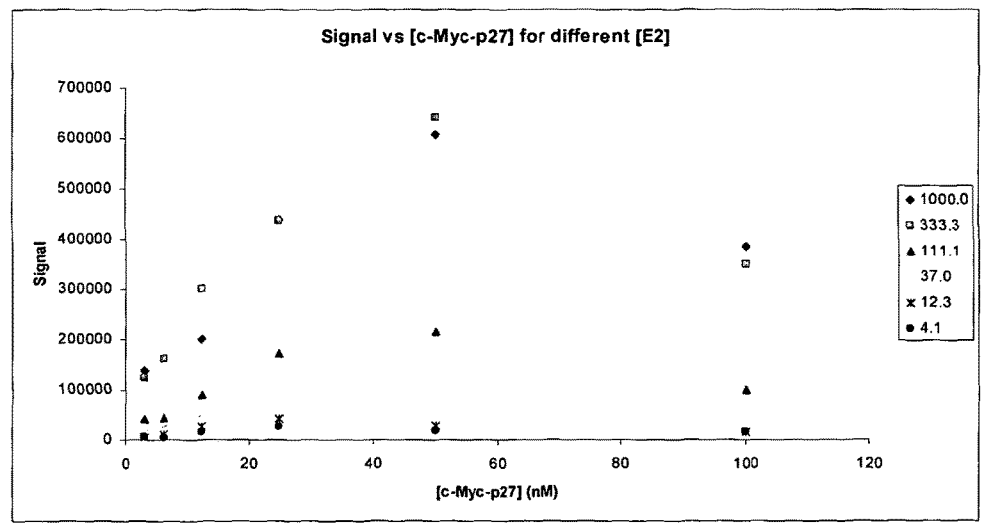

Figure 16
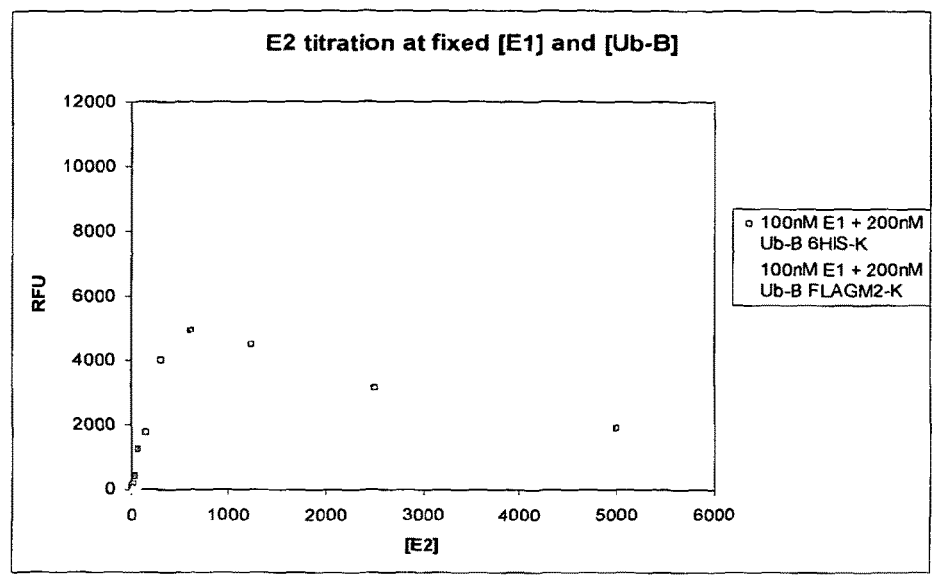
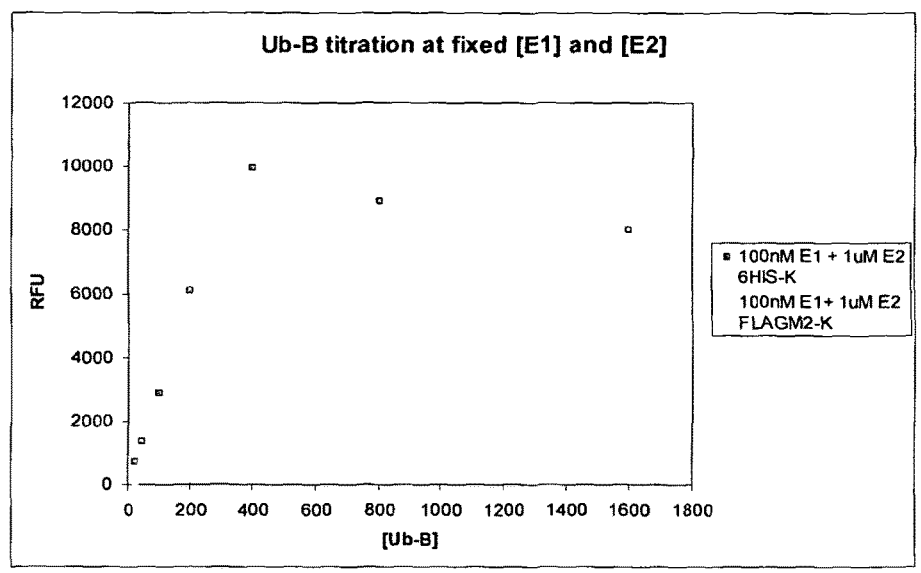

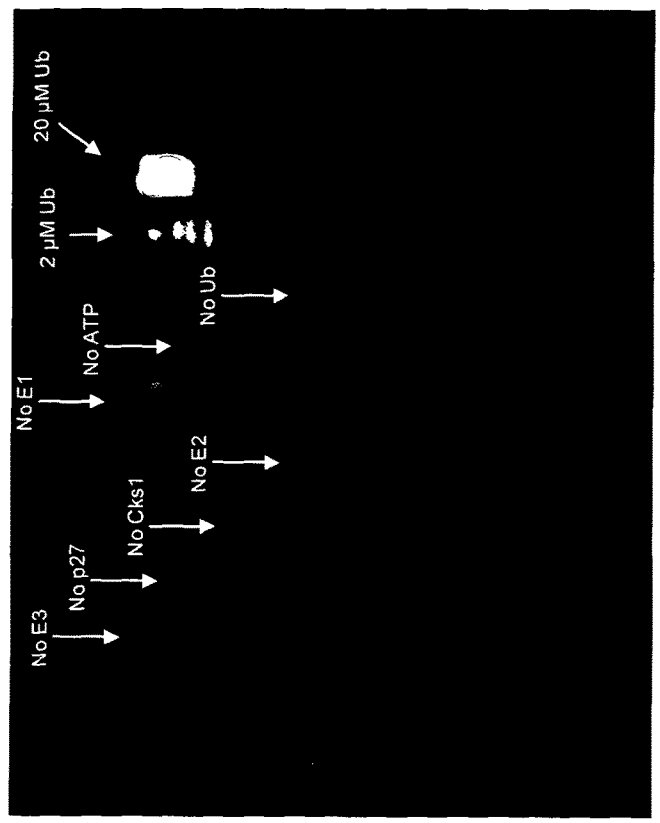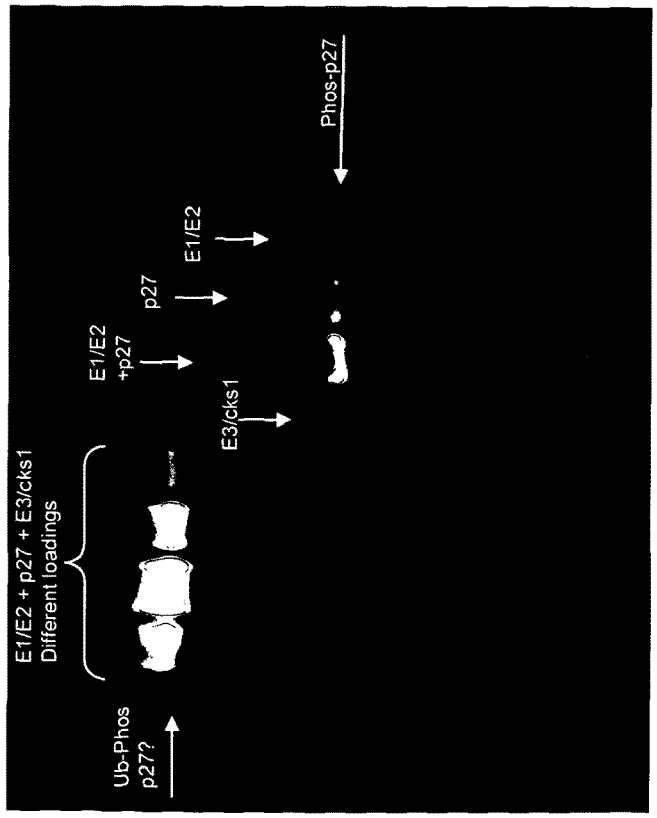
Figure 19

Figure 23 (a)
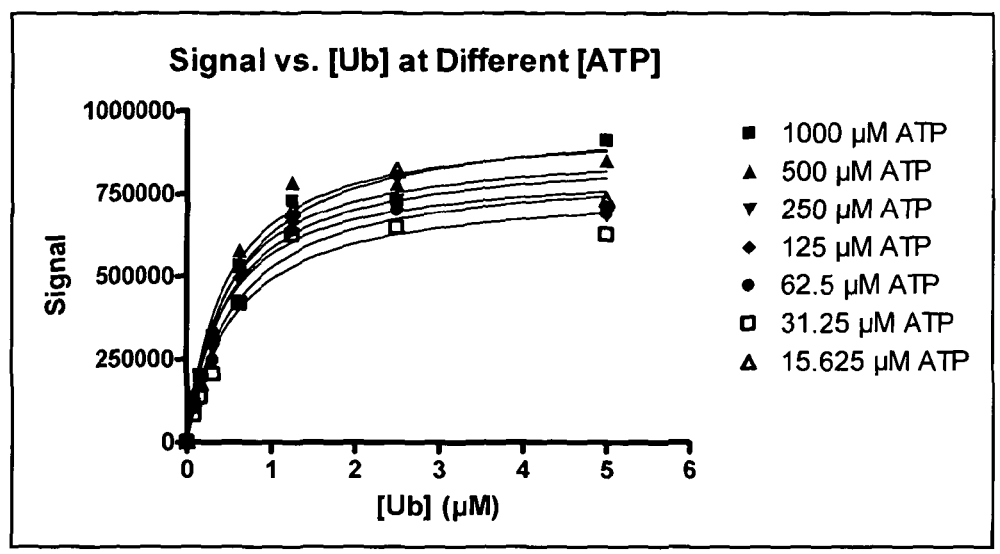
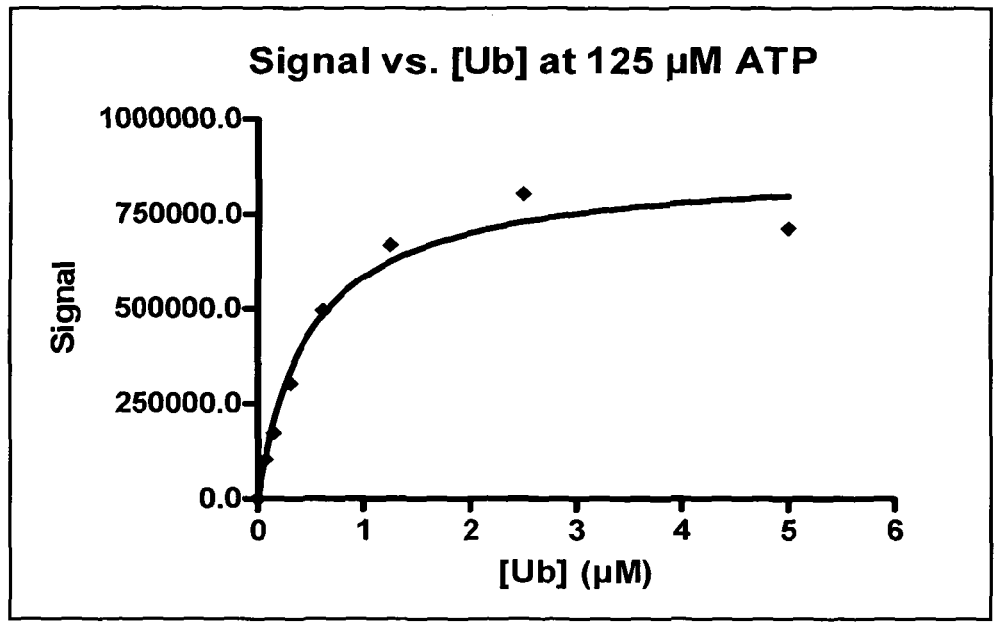

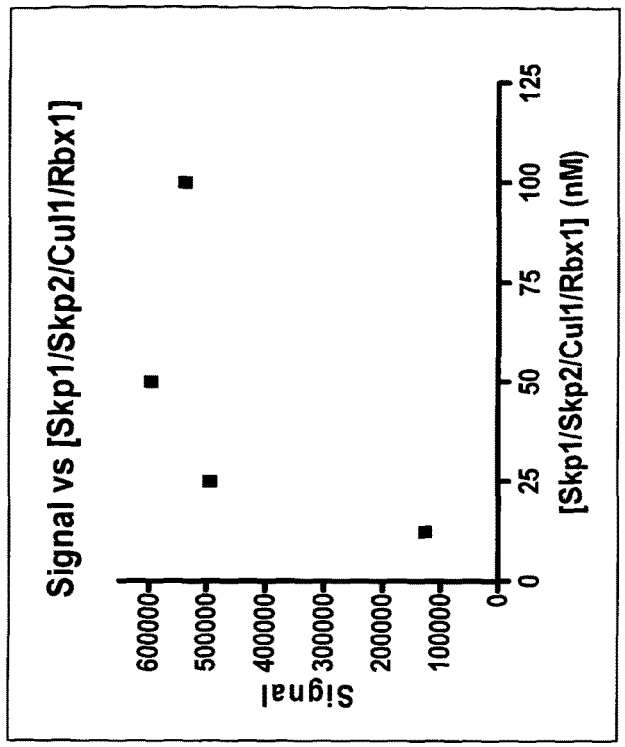
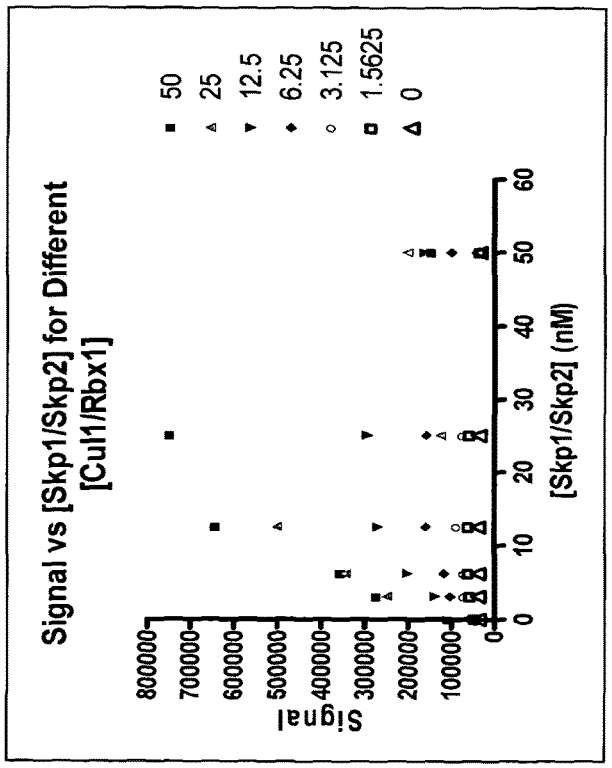
Figure 27

|  | Run 1 | Run 2 | Run 3 |
|---|---|---|---|
| Signal | 640778 | 838244 | 883807 |
| Background | 183 | 181 | 118 |
| Signal/Background | 3502 | 4631 | 7490 |
| % CV (Positive Controls) | 9.24 | 10.71 | 7.06 |
| Z' | 0.723 | 0.679 | 0.788 |

Figure 29

| RI Number | Inhibitor | FAC (µM) |
|---|---|---|
| - | PYR-41 | 100 |
| 1 | PP2 | 1 |
| 2 | PP3 | 1 |
| 3 | LY294002 | 50 |
| 4 | SB203580 | 10 |
| 5 | HA1077 | 10 |
| 6 | Roscovitine | 10 |
| 7 | Rottlerin | 10 |
| 8 | EGCG | 10 |
| 9 | K252c | 1 |
| 10 | Staurosporine | 1 |
| 11 | SU6656 | 10 |
| 12 | AG1296 | 10 |
| 13 | Olomoucine | 50 |
| 14 | Ro31-8220 | 1 |
| 15 | AG183 | 10 |
| 16 | Wortmannin | 1 |
| 17 | Genistein | 10 |
| 18 | AG18 | 10 |
| 19 | AG1024 | 10 |
| 20 | AG538 | 10 |

| RI Number | Inhibitor | FAC (µM) |
|---|---|---|
| 21 | AG1478 | 10 |
| 22 | H89 | 10 |
| 23 | Y27632 | 10 |
| 24 | Alsterpaullone | 1 |
| 25 | Curcumin | 50 |
| 26 | Indirubin monoxime | 10 |
| 27 | CDK2/5 inhibitor | 10 |
| 28 | JNK Inhibitor II | 10 |
| 29 | KT5720 | 1 |
| 30 | ST638 | 10 |
| 31 | ZM336372 | 10 |
| 32 | GW583340 | 10 |
| 33 | GW441756 | 10 |
| 34 | Okadaic acid | 1 |
| 35 | API-2 | 10 |
| 36 | PD153035 | 1 |
| 37 | NECA | 10 |
| 38 | Neomycin B | 10 |
| 39 | JAK Inhibitor I | 1 |
| 40 | UO126 | 10 |

Figure 31

UBIQUITINATION ASSAY

CROSS-REFERENCE TO RELATED APPLICATIONS

This application is the National Stage of International Application No. PCT/GB2011/00656, published in English under PCT Article 21(2), filed Apr. 28, 2011, which claims priority to United Kingdom patent Application No. 1007182.7, filed on Apr. 29, 2010, each of which are incorporated by reference in their entirety.

FIELD OF THE INVENTION

This invention is directed to assays to measure the activity of ubiquitination enzymes and the use of such assays in screening for agents that modulate this activity.

BACKGROUND OF THE INVENTION

Many diseases are caused by aberrant levels of proteins which cause cellular responses to be either heightened or dampened. Under normal conditions, proteins are targeted for proteasomal degradation by the ubiquitination pathway. Ubiquitination is the post-translational modification of a protein by the covalent attachment of one or more ubiquitin monomers.

The cascade leading to ubiquitination by a ubiquitination ligase (E3) is a complex enzymatic process with numerous proteins involved. There are three different catalytic events: ubiquitin activation; ubiquitin conjugation and ubiquitin ligation.

Ubiquitin is first activated in an ATP-dependent manner by a ubiquitin activating enzyme (E1). The C-terminus of a ubiquitin forms a high energy thiolester bond with E1. The ubiquitin is then passed to a ubiquitin conjugating enzyme (E2; also called ubiquitin carrier protein), also linked to this second enzyme via a thiolester bond. The ubiquitin is finally linked to its target protein to form a terminal isopeptide bond under the guidance of a ubiquitin ligase (E3). In this process, chains of ubiquitin are formed on the target protein, each covalently ligated to the next through the activity of E3.

E1 and E2 are structurally related and well characterized enzymes. There are several species of E2 (at least 25 in mammals), some of which act in preferred pairs with specific E3 enzymes to confer specificity for different target proteins.

E3 enzymes contain two separate activities: a ubiquitin ligase activity to conjugate ubiquitin to substrates and form polyubiquitin chains via isopeptide bonds, and a targeting activity to bring the ligase and substrate physically together. Substrate specificity of different E3 enzymes is the major determinant in the selectivity of the ubiquitin-dependent protein degradation process.

As the ubiquitination cascade provides important targets for therapeutics, it is crucial to have an effective in vitro ubiquitination assay. In particular, it is important that such an assay can be used for high-throughput screening of potential ubiquitination cascade modulators.

Ubiquitination assays are known in the art. In U.S. Pat. No. 6,413,725, the level of ubiquitination of a particular substrate is measured by monitoring changes to the molecular weight of the substrate as a marker of ubiquitination activity. The assay is specific for the Cdc53 and Cdc-53 related human cullin E3 ubiquitin ligases and their limited substrates, e.g. Sic1. As the assay relies on changes in molecular weight of the substrate, direct measurement of ubiquitination over the time course of the reaction is difficult and the ubiquitinated substrates are preferably analysed after completion of the reaction, i.e. via SDS PAGE separation. This limitation makes the assay inefficient for high-throughput screening.

The ubiquitination assay described in EP1268847 measures E3 ligase activity by monitoring the amount of polyubiquitin bound to the ligase itself. The ligase and ubiquitin are labelled with a FRET pair. As the ligase is labelled with one member of the FRET pair, it is directly involved in detection of ubiquitination. Furthermore, the ubiquitination measured is ubiquitination of the ligase itself. Therefore, the assay is limited to use in detection of auto-ubiquitination of a single E3 ligase.

Accordingly, although assays for ubiquitination already exist in the art, these assays have limited application. There is therefore a need in the art for improved ubiquitination assays which overcome the disadvantages associated with the assays known in the art and can be used for efficient high throughput screening of ubiquitination cascade modulators.

DISCLOSURE OF THE INVENTION

The inventors have developed an effective, reproducible ubiquitination assay which allows for the sensitive detection of ubiquitination.

Accordingly, the invention provides a method of assaying ubiquitination in a sample comprising:
  a. combining ubiquitin together with a substrate in a sample under conditions suitable for ubiquitination to take place, wherein the sample includes the following components: UBE1; UbcH3; Skp2-isoform 1; Skp1; Cul1; Rbx1; Cks1; CDK2; and Cyclin E1;
  b. exposing the sample to a labelled binding partner which is specific for the ubiquitin; and
  c. measuring the amount of ubiquitin bound to the substrate.

Preferably, any one of components of step (a) is immobilised on a solid surface. The solid surface may be an electrode.

Preferably, step (a) is a screening method for potential modulators of ubiquitination and so further includes a candidate modulator compound.

The invention also includes kits suitable for carrying out a method according to the invention. Accordingly, the invention provides a kit suitable for carrying out the methods of the invention. Preferably the kit comprises: ubiquitin; a substrate for E3 ligase; and a labelled binding partner which is specific for the ubiquitin. The kit should also include the following components: UBE1; UbcH3; Skp2-isoform 1; Skp1; Cul1; Rbx1; Cks1; CDK2; and Cyclin E1.

Providing an effective in vitro ubiquitination assay has until now been difficult due to E3 ligases forming such a large and varied group of proteins, each member of which may be modulated differently by a variety of different proteins. The inventors have overcome these difficulties and provided an optimised method for assaying ubiquitination as described in detail below.

Step (a)

The methods of the invention are for assaying ubiquitination in a sample. Step (a) involves combining all of the components required for a ubiquitination reaction to occur in a sample. Preferably the sample is in the form of a solution. The components of step (a) may be combined in any order. In a preferred embodiment, the ubiquitin is added to the sample last, in order to commence the ubiquitination reaction.

For the avoidance of doubt, a ubiquitination assay according to the invention includes both situations where ubiquitination is occurring and is suspected of occurring. Even if ubiquitination is not in fact occurring, the method is still one "for assaying ubiquitination". For example, the method may be performed on a negative control sample, for example, to confirm the fidelity of the assay. As a further example, if the assay is being used to select for a potential modulator of ubiquitination, the potential modulator may inhibit the process of ubiquitination.

Step (a) takes place in a first reaction container.

Suitable reaction containers for use in the invention can hold a volume of liquid and include, but are not limited to, test tubes, eppendorf tubes, wells in microtitre plates and mixing trays.

Step (a) of the methods of the invention is intended to be incubated for a finite period of time, for example, in the range of about 1 to 300 minutes, e.g. about 1, 2, 5, 10, 20, 40, 60, 120, 180, 240 or 300. An example of a preferred period is an incubation period between 10 and 60 minutes. Preferably the incubation period is 60 minutes.

Step (a) may be incubated at any temperature in the range of about 0-99° C., e.g. at around 5, 10, 15, 20, 25, 30, 35, 37, 40, 45, 50, or 60° C., or even higher. Conveniently, step (i) may be incubated at between about 20° C. and 40° C., for example, room temperature, 25, 30 or 37° C.

If the ubiquitination reaction is allowed to proceed for a finite period of time, then it may be stopped by, for example, the addition of EDTA, heating, freezing, acidification or alkination (i.e. pH shock), the addition of a known ubiquitination inhibitor, etc.

The sample may be any specimen in which the components of step (a) are combined together to allow a ubiquitination reaction to occur. The sample may contain other components in addition to the components described above. For example, the sample may comprise buffers, salts, metal ions, and other components required to facilitate ubiquitination. If the assay is being used to screen for potential modulators of ubiquitination, the sample will also include a candidate modulator.

Ubiquitination assays are well known in the art, and the skilled person will be aware of the conditions which are suitable for allowing a ubiquitination reaction to proceed. For example, a ubiquitination reaction mixture will usually comprise buffers, salts, metal ions, ATP, mono-ubiquitin and the enzymes described herein which are required to facilitate ubiquitination, i.e. one or more of E1, E2 and E3.

Step (b)

Step (b) of a method according to the invention involves exposing the sample to a labelled binding partner. This step can take place in the same reaction container or may involve the transfer of the sample to a second reaction container.

If step (b) takes place in the same reaction vessel, then the exposure of the sample to the labelled binding partner may be facilitated by the addition of a slide, rod or beads, coated with the labelled binding partner, to the first reaction vessel or may simply involve the addition of the labelled binding partner to the sample, e.g. as a solution.

Step (b) may occur after the sample has been incubated for a period of time, but may also occur at approximately the same time as the step (a). For example, the labelled binding partner may be in solution with the sample or may be added at a particular time point during the ubiquitination reaction. Therefore, the labelled binding partner may form part of the sample, or may be added to the sample at a later stage. Both of these embodiments are included when we refer to "exposing the sample".

If step (b) occurs after the ubiquitination reaction has been allowed to occur for a finite period of time, the reaction may have been stopped as described above and step (b) may occur minutes, hours, days, weeks or even months after the ubiquitination reaction has been stopped. The skilled reader will also appreciate that the components of step (a) may be mixed together and once the ubiquitination reaction has begun, samples may be taken continually throughout the reaction to produce a series of data over a certain time-course.

If step (b) of the methods of the invention involves the transfer of the sample to a second reaction container then this transfer can be achieved by any method known in the art including, but not limited to, pipetting, pouring or transfer along microchannels between wells in a microfluidic chip.

Also envisaged by the invention is a first reaction container, separated from the second reaction container by a removable partition. The partition prevents the sample of step (a) gaining access to the labelled binding partner until step (b). In such a case, transfer of the sample to the second reaction container involves the removal of the partition. For example, the mixing container may be an eppendorf tube containing a wax plug separating the reagents used in step (a) and step (b) of the reaction. Transfer of the first mixing product between the first and second reaction container in this example may be achieved by increasing the temperature of the tube sufficiently to melt the wax plug.

Ubiquitination Pathway

Ubiquitination of proteins in vivo is normally carried out by three enzymes: E1, E2 and a ubiquitin ligase, often referred to in the art as an E3 ligase. The process occurs in three stages. Firstly, activation of ubiquitin is undertaken by the ubiquitin activating enzyme E1. A ubiquitin-adenylate is produced from ubiquitin and ATP, and is transferred to the active site of E1, where AMP is released. The second step involves the transfer of ubiquitin from the active site of E1 to the active site of E2, a ubiquitin conjugating enzyme, via a trans(thio)esterification reaction. The final step of ubiquitination produces an isopeptide bond between a lysine residue of the target protein and the ubiquitin. This is achieved by an E3 ligase which recognises the target protein, forms interactions with both the ubiquitin bound E2 enzyme and the target protein, and finally forms the isopeptide bond between the lysine and the ubiquitin. Further ubiquitins are then added by the same mechanism to a lysine residue present on the ubiquitin attached to the target protein, and the process is repeated in order to form a chain of poly-Ub.

The methods of the invention are based on a specific combination of components for the ubiquitination assay which have proven to be particularly effective with a range of different substrates.

E1 Ubiquitin-like Modifier Activating Enzyme 1 (UBE1)

UBE1, also known as UBA1, is an enzyme which in humans is encoded by the UBA1 gene. UBE1 catalyzes the first step in ubiquitin conjugation to mark cellular proteins for degradation by first adenylating its C-terminal glycine residue with ATP, and thereafter linking this residue to the side chain of a cysteine residue in E1, yielding an ubiquitin-E1 thioester and free AMP.

Preferably the UBE1 used in the methods of the present invention is the human protein, which is a 1058 amino acid protein (Pubmed accession no.: NP_003325) having the sequence given in SEQ ID NO:1, or an active fragment or variant thereof.

Preferably the UBE1 is present in the sample at a final concentration of 3-7 nM, i.e. 3, 4, 5, 6 or 7 nM. It is especially preferred that the UBE1 is present in the sample at a final concentration of 5 nM.

E2 UbcH3

While the nomenclature for E2 (also known as ubiquitin-conjugating enzyme) is not standardized across species, investigators in the field have addressed this issue and the skilled person will readily be able to identify various E2 proteins, as well as species homologues (See Haas and Siepmann, FASEB J. 11: 1257-1268 (1997)). These enzymes oversee the second step in the ubiquitination reaction that targets a protein for degradation via the proteasome.

Once activated by E1, the activated ubiquitin is transferred to an E2 cysteine. Once conjugated to ubiquitin, the E2 molecule binds one of several ubiquitin ligases or E3s via a structurally-conserved binding region.

Preferably the E2 enzyme used in the methods of the present invention is UbcH3 or an active fragment or variant thereof, preferably human UbcH3, which is also known as CDC34. Human UbcH3 is a 236 amino acid protein (Pubmed accession no.: NP_004350.1) having the sequence given in SEQ ID NO:2.

Preferably the UbcH3 is present in the sample at a final concentration of 750-1250 nM, i.e. 750, 775, 800, 825, 850, 875, 900, 925, 950, 975, 1000, 1025, 1050, 1075, 1100, 1125, 1150, 1175, 1200, 1225 or 1250 nM. It is especially preferred that the UbcH3 is present in the sample at a final concentration of 1 µM.

E3

Some E3 ubiquitin ligases are known to have a single subunit responsible for the ligase activity. Such E3 ligases that have been characterized include the HECT (homologous to E6-AP carboxy terminus) domain proteins, represented by the mammalian E6AP-E6 complex which functions as a ubiquitin ligase for the tumor suppressor p53 and which is activated by papillomavirus in cervical cancer (Huang et al., Science 286: 1321-26 (1999)).

Single subunit ubiquitin ligases having a RING domain include Mdm2, which has also been shown to act as a ubiquitin ligase for p53, as well as Mdm2 itself. Other RING domain, single subunit E3 ligases include: TRAF6, involved in IKK activation; Cbl, which targets insulin and EGF; Sina/Siah, which targets DCC; Itchy, which is involved in haematopoiesis (B, T and mast cells); and IAP, involved with inhibitors of apoptosis.

The best characterized E3 ligase is the APC (anaphase promoting complex), which is a multi-subunit complex that is required for both entry into anaphase as well as exit from mitosis (King et al., Science 274: 1652-59 (1996) for review).

In eukaryotes, a family of complexes with E3 ligase activity play an important role in regulating G1 progression. These complexes, called SCFs, consist of at least three subunit: SKP 1, Cullins (having at least seven family members) and an F-box protein (of which hundreds of species are known) which bind directly to and recruit the substrate to the E3 complex.

Preferably the methods of the present invention utilise an E3 ligase comprising the following components:

S-phase Kinase-associated Protein 2 (Skp2)

Skp2 is an enzyme that in humans is encoded by the SKP2 gene. This gene encodes a member of the F-box protein family which is characterized by an approximately 40 amino acids motif, the F-box. The F-box proteins constitute one of the four subunits of a ubiquitin protein ligase complex called SCF, which functions in phosphorylation-dependent ubiquitination. The F-box proteins are divided into 3 classes: Fbws containing WD-40 domains, Fbls containing leucine-rich repeats, and Fbxs containing either different protein-protein interaction modules or no recognizable motifs (Kipreos ET, Pagano M. (2000). The F-box protein family. Genome Biol 1(5):Reviews 3002).

The protein encoded by the Skp2 gene belongs to the Fbls class; in addition to an F-box, this protein contains 10 tandem leucine-rich repeats. It specifically recognizes phosphorylated cyclin-dependent kinase inhibitor 1B (CDKN1B, also referred to as p27 or KIP1) predominantly in S phase and interacts with S-phase kinase-associated protein 1 (SKP1 or p19). Alternative splicing of this gene generates 2 transcript variants encoding different isoforms.

It is preferred that a method according to the present invention utilizes the human isoform-1 variant of Skp2 which is a 424 amino acid protein (Pubmed accession no.: AAK31593), or an active fragment or variant thereof. The wild type sequence is given in SEQ ID NO:3.

Preferably the Skp2 protein is present in the sample at a final concentration of between about 20-30 nM, i.e. about 20, 21, 22, 23, 24, 25, 26, 27, 28, 29, or about 30 nM. It is particularly preferred that the Skp2 is present in the sample at a final concentration of 25 nM.

Skp1

S-phase kinase-associated protein 1 (SKP1) is an enzyme that in humans is encoded by the Skp1 gene. SKP1 is a member of the SCF ubiquitin ligase protein complex. It binds to proteins containing an F-box motif, such as cyclin F, Skp2, and other regulatory proteins involved in ubiquitination. Alternative splicing of this gene results in two transcript variants: "isoform-a" and "isoform-b".

It is preferred that a method according to the invention utilizes the human isoform-a variant of Skp1 which is a 160 amino acid protein (Pubmed accession no.: NP_008861), or an active fragment or variant thereof. The wild type sequence is given in SEQ ID NO:4.

Preferably the Skp1 is present in the sample at a final concentration of 20-30 nM, i.e. about 21, 22, 23, 24, 25, 26, 27, 28, 29, or about 30 nM. It is particularly preferred that the Skp1 is present in the sample at a final concentration of 25 nM.

Cullin 1 (Cul1)

Cul1 is a human protein and gene from the cullin family. Cul1 plays an important role in protein degradation and protein ubiquitination and is an essential component of the SCF (SKP1-CUL1-F-box protein) E3 ubiquitin ligase complex. In the SCF complex, Cul1 serves as a rigid scaffold that organizes the SKP1-F-box protein and RBX1 subunits. The protein is usually neddylated, which enhances the ubiquitination activity of SCF.

Preferably the methods of the invention utilize human Cul1, which is a 776 amino acid protein (Pubmed accession no.: NP_003583), or a fragment or variant thereof. The wild type protein has the sequence given in SEQ ID NO:5.

Preferably the Cul1 is present in the sample at a final concentration of 20-30 nM, i.e. about 20, 21, 22, 23, 24, 25, 26, 27, 28, 29, or about 30 nM. It is particularly preferred that the Cul1 is present in the sample at a final concentration of about 25 nM.

RING-box Protein 1 (Rbx11

Rbx1 is a protein that in humans is encoded by the RBX1 gene. Rbx1 is an evolutionarily-conserved protein which interacts with cullins. The protein plays a unique role in the ubiquitination reaction by heterodimerizing with Cul1 to catalyze ubiquitin polymerization.

Preferably the methods of the invention utilize human Rbx1, which is a 108 amino acid protein (Pubmed accession no.: CAG30446), or an actice fragment or variant thereof. The wild type protein has the sequence given in SEQ ID NO:6.

Preferably the Rbx1 is present in the sample at a final concentration of 20-30 nM, i.e. about 20, 21, 22, 23, 24, 25, 26, 27, 28, 29, or about 30 nM. It is particularly preferred that the Rbx1 is present in the sample at a final concentration of 25 nM.

Cks1

Cks1 is a member of the highly conserved Suc1/Cks family of cell cycle regulatory proteins and is also known as CDC28. All proteins of this family have Cdk-binding and anion-binding sites, but only mammalian Cks1 binds to Skp2 and promotes the association of Skp2 with p27 phosphorylated on Thr-187.

Preferably the methods of the invention utilize human Cks1, which is a 79 amino acid protein (Pubmed accession no.: NP_001817) or a fragment or variant thereof. The wild type protein has the sequence given in SEQ ID NO:7.

Preferably the Cks1 is present in the sample at a final concentration of 20-30 nM, i.e. about 20, 21, 22, 23, 24, 25, 26, 27, 28, 29, or about 30 nM. It is particularly preferred that the Cks1 is present in the sample at a final concentration of 25 nM.

Cyclin-dependent Kinase 2 (CDK2)

CDK2 is a human gene which encodes a protein which is a member of the cyclin-dependent kinase family of Ser/Thr protein kinases. This protein kinase is highly similar to the gene products of *S. cerevisiae* cdc28, and *S. pombe* cdc2. Two alternatively spliced variants and multiple transcription initiation sites of this gene have been reported.

Preferably the methods of the invention utilize human CDK2, which is a 298 amino acid protein (Pubmed accession no.: CAA43985) or an active fragment or variant thereof. The wild type protein has the sequence given in SEQ ID NO:8.

Preferably the CDK2 is present in the sample at a final concentration of 20-30 nM, i.e. about 20, 21, 22, 23, 24, 25, 26, 27, 28, 29, or about 30 nM. It is particularly preferred that the CDK2 is present in the sample at a final concentration of 25 nM.

Cyclin E1

Cyclin-E1 is a protein that in humans is encoded by the CCNE1 gene. Cyclin E1 belongs to the highly conserved cyclin family, whose members are characterized by a dramatic periodicity in protein abundance through the cell cycle. Cyclins function as regulators of CDK kinases. Different cyclins exhibit distinct expression and degradation patterns which contribute to the temporal coordination of each mitotic event. This cyclin forms a complex with and functions as a regulatory subunit of CDK2, whose activity is required for cell cycle G1/S transition.

This protein accumulates at the G1-S phase boundary and is degraded as cells progress through S phase. Overexpression of this gene has been observed in many tumors, which results in chromosome instability, and thus may contribute to tumorigenesis. Two alternatively spliced transcript variants of this gene, which encode distinct isoforms, have been described.

Preferably the methods of the invention utilize human Cyclin E1, which is a 395 amino acid protein (Pubmed accession no.: AAM54043), or an active fragment or variant thereof. The wild type protein has the sequence given in SEQ ID NO:9.

Preferably the Cyclin E1 is present in the sample at a final concentration of 20-30 nM, i.e. about 20, 21, 22, 23, 24, 25, 26, 27, 28, 29, or about 30 nM. It is particularly preferred that the cyclin E1 is present in the sample at a final concentration of 25 nM.

Substrate

The methods of the invention provide a ubiquitination assay which is suitable for use with a number of different substrates. Examples of such substrates will be known to the skilled person and, in particular, are described in Deshaies & Joazeiro (Annu Rev Biochem. 2009; 78:399-434). Preferably the substrate is p27.

p27 p27, also known as cyclin-dependent kinase inhibitor 1B is an enzyme that in humans is encoded by the CDKN1B gene. p27 belongs to the Cip/Kip family of cyclin dependent kinase (Cdk) inhibitor proteins. The encoded protein binds to and prevents the activation of cyclin E-CDK2 or cyclin D-CDK4 complexes, and thus controls the cell cycle progression at G1. It is often referred to as a cell cycle inhibitor protein because its major function is to stop or slow down the cell division cycle.

The p27Kip 1 gene has a DNA sequence similar to other members of the "Cip/Kip" family which include the p21Cip1/Waf1 and p57Kip2 genes. In addition to this structural similarity the "Cip/Kip" proteins share the functional characteristic of being able to bind several different classes of Cyclin and Cdk molecules. For example, p27Kip1 binds to cyclin D either alone, or when complexed to its catalytic subunit CDK4. Likewise, p27Kip1 is able to bind other Cdk proteins when complexed to cyclin subunits such as Cyclin E/Cdk2 and Cyclin A/Cdk2.

Preferably the methods of the invention utilize human p27, which is a 199 amino acid protein (Pubmed accession no.: BAA25263) or an active fragment or variant thereof. The wild type protein has the sequence given in SEQ ID NO:10. Preferably the p27 is phosphorylated at position T187.

Preferably the p27 is present in the sample at a final concentration of 20-30 nM, i.e. about 20, 21, 22, 23, 24, 25, 26, 27, 28, 29, or about 30 nM. It is particularly preferred that the p27 is present in the sample at a final concentration of 25 nM.

Preferred Combinations of Components

Preferably the Skp2 isoform 1, Skp1, Cul1 and Rbx1 are combined with each other prior to combination with the other components of (a). In this embodiment these four components are thought to form a tetramer. Preferably the Skp2 isoform 1, Skp1, Cul1 and Rbx1 tetramer are present in the sample at a final concentration of 20-30 nM, i.e. about 20, 21, 22, 23, 24, 25, 26, 27, 28, 29, or about 30 nM. It is particularly preferred that the Skp2 isoform 1, Skp1, Cul1 and Rbx1 tetramer is present in the sample at a final concentration of 25 nM.

Preferably the p27, CDK2 and cyclin E1 are combined with each other prior to combination with the other components of (a). Preferably the p27, CDK2 and cyclin E1 are co-expressed in the same host cell and purified as a complex, which is then used in the methods of the invention. If the p27, CDK2 and cyclin E1 are combined together prior to the combination with the other components, or are co-expressed, then preferably the complex should be present in the sample at a final concentration of 20-30 nM, i.e. about 20, 21, 22, 23, 24, 25, 26, 27, 28, 29, or about 30 nM. Preferably the p27, CDK2 and cyclin E1 complex are present in the sample at a final concentration of 25 nM.

Variants

The preferred E1, E2, E3 components and substrate for use in the methods of the invention are described above.

However, the skilled person will appreciate that these components can be substituted with any known variant of these components, including active fragments, naturally-occurring alleles, modified variants or variants from species other than *Homo sapiens*. These variants are all suitable for use in the methods of the invention, provided that they retain activity. By "retain activity" is meant that the normal biological activity of the wild type protein, as a component of the ubiquitination machinery, is retained to such a degree to enable the assay to function at a level adequate for the researcher's requirements e.g. at a level 30%, 40%, 50%, 60%, 70%, 80%, 90% or more of wild type activity.

A variant of the various components may comprise substitutions, additions or deletions in its amino acid sequence compared to SEQ ID NOs: 1, 2, 3, 4, 5, 6, 7, 8, 9 or 10. In a preferred embodiment, the variant comprises an amino acid sequence with greater than 75% sequence identity, i.e. 80%, 85%, 90% or 95% or more to the amino acid sequence of one of SEQ ID NOs: 1, 2, 3, 4, 5, 6, 7, 8, 9 or 10.

A variant may also represent a fragment of the wild type full length protein, truncated, for example, at one or both the N and/or C termini. A truncation may be to a length 50% of the full length sequence, or 60%, 70%, 80%, or 90% or more of the full length sequence, provided that the biological activity of the wild type protein is retained to such a degree to enable the assay to function at a level adequate for the researcher's requirements e.g. at a level 30%, 40%, 50%, 60%, 70%, 80%, 90% or more of wild type activity.

A variant may also form part of a larger protein complex. For example, a variant may represent one domain of a multi-domain protein, or may further comprise additional features to facilitate purification, detection and stability of the expressed protein. For example, the variant may comprise a polyarginine tag (Arg-tag), polyhistidine tag (His-tag), FLAG-tag, Strep-tag, c-myc-tag, S-tag, calmodulin-binding peptide, cellulose-binding domain, SBP-tag chitin-binding domain, glutathione S-transferase-tag (GST), maltose-binding protein, transcription termination anti-termination factor (NusA), *E. coli* thioredoxin (TrxA) and protein disulfide isomerase I (DsbA).

Ubiquitin (Ub)

Ubiquitin is a highly conserved regulatory protein that is present in all eukaryotic cells.

The ubiquitin used in the methods of the invention may comprise any known variant of ubiquitin including naturally occurring alleles or modified variants. As ubiquitin is highly conserved, the ubiquitin used in the present invention may be ubiquitin from any species, for example, human ubiquitin which comprises the amino acid sequence given in SEQ ID NO: 11, mouse ubiquitin which comprises the amino acid sequence given in SEQ ID NO: 12, *Arabidopsis* ubiquitin which comprises the amino acid sequence given in SEQ ID NO: 13, yeast ubiquitin which comprises the amino acid sequence given in SEQ ID NO: 14, *Drosophila* ubiquitin which comprises the amino acid sequence given in SEQ ID NO: 15, *Dictyostelium* ubiquitin which comprises the amino acid sequence given in SEQ ID NO: 16 or bovine ubiquitin which comprises the amino acid sequence given in SEQ ID NO: 17. Preferably, the ubiquitin used in the present invention is human ubiquitin, which comprises the amino acid sequence given in SEQ ID NO: 11, or an active variant or fragment thereof.

A variant of ubiquitin may comprise substitutions, additions or deletions in its amino acid sequence compared to SEQ ID NOs: 11, 12, 13, 14, 15, 16 or 17. In a preferred embodiment, ubiquitin comprises an amino acid sequence with greater than 75% sequence identity, i.e. 80%, 85%, 90% or 95% or more to the amino acid sequence of one of SEQ ID NOs: 11, 12, 13, 14, 15, 16 or 17. The ubiquitin of the invention may comprise a tag. Where the ubiquitin comprises a tag it is referred to as "tagged ubiquitin" and the tag is referred to as "the ubiquitin tag".

Preferably the ubiquitin is present in the sample at a final concentration of between 1-3 μM, i.e. about 1, 1.25, 1.5, 1.75, 2, 2.25, 2.5, 2.75 or about 3 μM. It is particularly preferred that the ubiquitin is present in the sample at a final concentration of 2 μM.

Preferably the ubiquitin comprises a tag.

In one embodiment the ubiquitin or ubiquitin tag is recognized by the labelled binding partner. The skilled person will appreciate that, if present, the choice of tag is dependent on the choice of labelled binding partner. For example, if the labelled binding partner is an antibody then the tag may be a protein which is recognizable by the labelled binding partner antibody or vice versa. If the labelled binding partner is not an antibody, then the ubiquitin tag may be a protein with a high affinity for it. In a preferred embodiment, the ubiquitin tag is biotin or a derivative thereof and the labelled binding partner is streptavidin or a derivative thereof.

In another embodiment, the ubiquitin tag is capable of interacting with the labelled binding partner to produce a detectable signal. Preferably in this embodiment the ubiquitin tag and the labelled binding partner form a FRET (fluorescence resonance energy transfer) pair. In this case the ubiquitin tag will be either a donor or acceptor dye, whilst the labelled binding partner will be labelled with the other. Only when the two are brought into close proximity, through the respective binding of the ubiquitin and labelled binding partner, will photon emission be observable.

Labels used to form a FRET pair can be any molecule that may be detected via its inherent fluorescent properties. Examples of fluorescent labels include, but are not limited to fluorescein isothiocyanate, fluorescein/rhodamine, coumarin/fluorescein, Alexa fluors, IAEDANS, BODIPY FL, europium cryptate, Cy dyes, XL665 and Oregon green. In a preferred embodiment the two labels which constitute the FRET pair are europium cryptate and XL665. In addition to FRET partners, FRET/Quench methods may be used in the invention. These methods rely on a donor dye and another molecule which accepts energy but does not emit, effectively quenching the donor dye, for example iron quench.

Poly-ubiquitin (Poly-Ub)

It will be appreciated that poly-Ub comprises at least two ubiquitin monomers covalently attached to one another. Poly-Ub of the present invention is a polymer formed from ubiquitin as described above. Poly-Ub comprises two or more labelled ubiquitins covalently attached to one another e.g. 2, 3, 4, 5, 6, 7, 8, 9, 10, 11, 12, 13, 14 or 15 or more. Poly-Ub may be free poly-Ub chains, poly-Ub bound to a substrate protein, or poly-Ub bound to the ubiquitin ligase.

Adenosine-5'-triphosphate (ATP)

ATP is a multifunctional nucleotide used in cells as a coenzyme. ATP transports chemical energy within cells for metabolism. It is produced by photophosphorylation and cellular respiration and used by enzymes and structural proteins in many cellular processes, including biosynthetic reactions, motility, and cell division. One molecule of ATP contains three phosphate groups, and it is produced by ATP synthase from inorganic phosphate and adenosine diphosphate (ADP) or adenosine monophosphate (AMP). Guanidine-5'-triphosphate (GTP), Cytidine-5'-triphosphate (CTP), Uridine-5'-triphosphate (UTP) or Thymidine-5'-triphosphate (TTP) may also be used in the methods of the invention.

Preferably, the methods of the invention use ATP.

Preferably the ATP is present in the sample at a final concentration of 75-125 μM, i.e. about 75, 80, 85, 90, 95, 100, 105, 110, 115, 120 or about 125 μM. Preferably, the ATP is present in the sample at a final concentration of 100 μM.

Labelled Binding Partner

The labelled binding partner used in the methods of the invention interacts with the ubiquitin either directly or via the ubiquitin tag. The labelled binding partner is specific for the ubiquitin or the tagged ubiquitin. As such, the labelled binding partner may bind to the ubiquitin or to the ubiquitin tag and both possibilities are used interchangeably herein.

Preferably, the labelled binding partner has a higher affinity for ubiquitin than for any of the other components used in the methods of the invention, in the sense that it binds preferentially to ubiquitin.

Preferably the labelled binding partner has a binding affinity (Kd) of less than $10^{-6}$M, i.e. $10^{-7}$M, $10^{-8}$M, $10^{-9}$M, $10^{-10}$M, $10^{-11}$M, $10^{-12}$M or even $10^{-13}$M or less towards ubiquitin. Preferably, the labelled binding partner has a binding affinity (Kd) of less than $10^{-9}$M, i.e., $10^{-10}$M, $10^{-11}$M, $10^{-12}$M or $10^{-13}$M towards ubiquitin.

The labelled binding partner may comprise one or more molecules which have an affinity for ubiquitin.

The labelled binding partner may comprise an antibody. Antibodies may be of any isotype (e.g. IgA, IgG, IgM i.e. an α, γ or μ heavy chain). Antibodies may have a κ or a λ light chain. Within the IgG isotype, antibodies may be IgG1, IgG2, IgG3 or IgG4 subclass. The term "antibody" includes any suitable natural or artificial immunoglobulin or derivative thereof. In general, the antibody will comprise a Fv region which possesses specific antigen binding activity. This includes, but is not limited to: whole immunoglobulins, antigen binding immunoglobulin fragments (e.g. Fv, Fab, F(ab')2 etc.), single chain antibodies (e.g. scFv), oligobodies, chimeric antibodies, humanized antibodies, veneered antibodies, etc.

Antibodies used as the labelled binding partner of the invention may be polyclonal or monoclonal.

The labelled binding partner may in an alternative embodiment, comprise an aptamer. By 'aptamer' we mean a nucleic acid sequence which, owing to said nucleic acid sequence and the environment in which this sequence is located, forms a three-dimensional structure. The three-dimensional structure confers, in part, binding properties to aptamers which have specificity to a target molecule or molecules. In the present invention, the aptamer shows binding specificity towards ubiquitin molecule.

Aptamers are typically oligonucleotides which may be single stranded oligodeoxynucleotides, oligoribonucleotides, or modified oligodeoxyribonucleotides or modified oligoribonucleotides. A screening method to identify aptamers is described in U.S. Pat. No. 5,270,163. The term 'modified' in the context of aptamers refers to nucleotides with a covalently modified base and/or sugar or sugar derivative.

In another alternative embodiment the labelled binding partner may comprise a ubiquitin binding domain (UBD). UBDs are modular protein domains that are able to bind non-covalently to ubiquitin. The natural function of UBDs is to transmit information conferred by protein ubiquitination in order to control various cellular events. UBDs usually comprise 20-150 amino acids and can be found as part of ubiquitination enzymes, de-ubiquitination enzymes or ubiquitin receptors. Around 10 different motifs have so far been characterised as ubiquitin binding domains (Hicke et al., 2005), the structures of which are highly varied. All UBDs however contact the same face of ubiquitin, which comprises the amino acid residue isoleucine 44. The different motifs of UBDs have different affinities for mono-Ub and poly-Ub depending on their function in vivo, and some of the UBDs also distinguish between poly-Ub with linkage at lysine 63 and that with linkage at lysine 48.

UBDs are present in all proteins that are capable of binding ubiquitin and therefore all proteins that are involved in the ubiquitination reaction or the recognition of ubiquitinated proteins contain a UBD within them.

Within this embodiment the UBD may be a particular class of UBD which is able to bind to poly-Ub preferentially over mono-Ub. These are known as ubiquitin associated domains (UBAs). UBAs are able to distinguish between poly-Ub and mono-Ub because they have a higher binding affinity for poly-Ub compared to mono-Ub. Preferably, the UBAs form three-helix bundles, with two of these three helices packing against ubiquitin on binding.

The preferential binding affinity for poly-Ub over mono-Ub may be defined by the UBAs' respective dissociation constants (Kd) for the two species. Binding affinity of UBAs may typically be between 10 and 1000 times greater for poly-Ub compared to mono-Ub, i.e. 10, 20, 30, 40, 50, 100, 200, 300, 400, 500, 600, 700, 800, 900, 1000 times or more greater for poly-Ub than for mono-Ub. Preferably, binding affinity of a UBA used in the present invention is about 50 times greater for poly-Ub than for mono-Ub. UBAs will typically have a Kd of about 0.03-9 μM, i.e. about 0.03, 0.04, 0.05, 0.1, 0.2, 0.3, 0.4, 0.5, 0.6, 0.7, 0.8, 0.9, 1, 2, 3, 4, 5, 6, 7, 8 or 9 μM for poly-Ub, and a Kd of about 10-500 μM, i.e. about 10, 20, 30, 40, 50, 60, 70, 80, 90, 100, 150, 200, 250, 300, 350, 400, 450 or 500 μM for mono-Ub.

Preferred UBAs include, but are not limited to, Rad23-UBA1 (Accession No. AAB28441, amino acids 146-186), Rad23-UBA2 (Accession No. AAB28441, amino acids 355-395), Dsk2-UBA (Accession No. NP_014003, amino acids 327-371), Ubp14-UBA2 (Accession No. CAA85001, amino acids 649-689), Ubc1-UBA (Accession no. CAA39812) and Rpn10-UIM (Accession no. EEU06553, amino acids 223-242). In one preferred embodiment the UBA is derived from the Rad23 protein. In a further preferred embodiment, the UBA comprises protein domain UBA2 of the Rad23 protein and comprises or consists of the amino acid sequence of SEQ ID NO: 18. The UBA used in the methods of the invention may comprise a variant of SEQ ID NO: 18. A variant of the UBA may comprise substitutions, additions or deletions in its amino acid sequence compared to SEQ ID NO: 18. The UBA may comprise an amino acid sequence with a sequence identity greater than 75%, i.e. 80%, 85%, 90% or 95% or more, to the amino acid sequence of SEQ ID NO:18. Variants of the UBA are included for use in the method of the invention provided that they maintain their ability to be able to bind to ubiquitin and preferably to differentiate between poly-Ub and mono-Ub, according to the definitions provided above.

UBAs may also form part of a larger protein complex. For example, they may represent one domain of a multi-domain protein, or may further comprise additional features to facilitate purification, detection and stability of the expressed protein, for example, a polyarginine tag (Arg-tag), polyhistidine tag (His-tag), FLAG-tag, Strep-tag, c-myc-tag, S-tag, calmodulin-binding peptide, cellulose-binding domain, SBP-tag chitin-binding domain, glutathione S-transferase-tag (GST), maltose-binding protein, transcription termination anti-termination factor (NusA), *E. coli* thioredoxin (TrxA) and protein disulfide isomerase I (DsbA).

UBAs may be provided in the form of multimeric complexes comprising two or more UBAs or in the form of individual entities. The multimeric complex may be dimeric, trimeric, tetrameric, pentameric or hexameric. The UBAs present within the multimeric complex may be the same or different. The multimeric complex may be Tandem Ubiquitin Binding Entities (TUBES; tetrameric) or Tandem Dimeric UBAs (dimeric). A tandem dimeric UBA may comprise one or more of Dsk2 and Rad23, and in one embodiment may comprise or consist of Dsk2 and Rad23.

The methods of the invention may also use one or more fragments of UBAs provided that the fragment maintains the functional ability to be able to bind to ubiquitin and preferably to distinguish between poly-Ub and mono Ub according to the definitions provided above.

In one embodiment one or more UBAs may be used to measure the level of polyubiquitin bound to any one of the components of the assay in step (c) as described in the PCT application entitled "Ubiquitination Assay" which claims priority from GB 1006604.1 and has the same Applicant as the present application.

In one embodiment, where the labelled binding partner recognises the ubiquitin or the ubiquitin tag the label present on the labelled binding partner may be measured directly or indirectly. Preferred labels include, but are not limited to, fluorescent labels, labelled enzymes and radioisotopes.

In a more preferred embodiment, the labelled binding partner is capable of emitting radiation when electrochemically stimulated. Preferably the radiation is in the visible spectrum. Preferably the label is selected from the group consisting of 3-aminophthalhydrazide; a ruthenium chelate and an acridan ester. Preferably the label is tris(2,2'-bipyridyl) ruthenium (II).

As discussed above in relation to the ubiquitin tag, the labelled binding partner is capable of interacting with the ubiquitin tag to produce a detectable signal. Preferably in this embodiment the ubiquitin tag and the labelled binding partner form a FRET (fluorescence resonance energy transfer) pair. In this case the labelled binding partner tag will be with either a donor or acceptor dye, whilst the ubiquitin tag will be labelled with the other. Only when the two are brought into close proximity, through the respective binding of the ubiquitin and labelled binding partner, will photon emission be observable.

Step (c)

In one embodiment, step (c) may be performed two or more times in order to measure the amount of labelled ubiquitin bound to two or more of the components in the sample. For example, step (c) may be performed twice in order to measure the amount of labelled ubiquitin bound to two of the components in the sample, three times in order to measure the amount of labelled ubiquitin bound to three of the components in the sample, four times in order to measure the amount of labelled ubiquitin bound to four of the components in the sample, five times in order to measure the amount of labelled ubiquitin bound to five of the components in the sample, six times in order to measure the amount of labelled ubiquitin bound to six of the components in the sample, seven times in order to measure the amount of labelled ubiquitin bound to seven of the components in the sample, eight times in order to measure the amount of labelled ubiquitin bound to eight of the components in the sample or nine times in order to measure the amount of labelled ubiquitin bound to all of the components in the sample.

Where step (c) is performed less than nine times, the amount of labelled ubiquitin bound to any combination of components may be measured. In all embodiments the amount of labelled ubiquitin bound to the components may be measured simultaneously or sequentially in any order.

Preferably the component(s) which is to be measured comprises an immobilisation tag. If the amount of labelled ubiquitin bound to each relevant component is to be measured simultaneously, each immobilisation tag should be different to allow each of the relevant components to be separated and the level of ubiquitination measured.

In one embodiment, the composition of the assay is not altered between measurements of the ubiquitination of individual components.

The repetition of step (c) allows a single assay to be used to directly measure different stages of the ubiquitination cascade or to sequentially determine activity at each stage of the cascade without changing the assay composition.

Assay Formats

The methods of the invention are suitable for use in a number of different assay formats. For example, the method may be performed in a format wherein all components are present in a homogeneous phase, or alternatively the method may be performed in a format where one or more of the components is immobilised.

Homogeneous Phase Assay

As described above, step (a) involves combining all of the components required for a ubiquitination reaction to occur in a sample. In a preferred embodiment, the samples are in a homogeneous phase, that is, one where at least two reactants or even all reaction components are in the fluid (solution) phase. This assay format lends itself to application in high throughput screening of ubiquitination reactions.

This embodiment of the invention preferably exploits a labelled binding partner and ubiquitin tag which are capable of interacting to produce a detectable signal, e.g. a FRET pair. As discussed above, only upon binding of these two components will a detectable signal be emitted.

Immobilised Assay

In another embodiment of the invention, the assay may be performed in a format wherein one of the components of the sample is immobilised on a solid surface.

In one embodiment any one of the components of the sample may be immobilised on a solid surface.

In another embodiment two or more of the components of the sample may be immobilised on a solid surface.

In another embodiment three or more of the components of the sample may be immobilised on a solid surface.

In another embodiment four or more of the components of the sample may be immobilised on a solid surface.

In another embodiment five or more of the components of the sample may be immobilised on a solid surface.

In another embodiment six or more of the components of the sample may be immobilised on a solid surface.

In another embodiment seven or more of the components of the sample may be immobilised on a solid surface.

In another embodiment eight or more of the components of the sample may be immobilised on a solid surface.

In another embodiment all of the components of the sample may be immobilised on a solid surface.

Preferably the component to be immobilised comprises an immobilisation tag which facilitates its immobilisation onto the surface. Preferably the solid surface comprises a binding member which is specific for the immobilisation tag.

Preferably, it is the substrate which comprises an immobilisation tag.

This embodiment of the invention preferably comprises an additional wash step, (b'), which occurs between steps (b) and (c) and removes unbound components from the solid surface.

The immobilisation of a component to the solid surface allows for the direct detection of the labelled binding partner. For example, immobilising the substrate will also immobilise any ubiquitin bound to the substrate and in turn any labelled binding partner bound to the ubiquitin. The amount of labelled binding partner present is proportional to the amount of ubiquitin bound to the substrate. If the label present on the labelled binding partner is, for example, a dye, this will be visible.

In a preferred embodiment, the solid surface is an electrode. The labelled binding partner comprising a label which is capable of emitting radiation, preferably in the visible spectrum, upon stimulation is particularly suitable for use with this embodiment of the invention. If ubiquitination of the substrate has occurred, its immobilisation onto the electrode will bring bound ubiquitin, and in turn labelled binding partner into close proximity with the electrode. Passing a current through the electrode will cause stimulation of the labelled binding partner, in turn causing a signal to be emitted (See FIG. 39). The skilled person will appreciate that this embodiment of the invention is based on the principals of electrochemiluminescence.

Electrochemiluminescence

Electrochemiluminescence, or electrogenerated chemiluminescence (ECL) is a kind of luminescence produced during electrochemical reactions in solutions. In electrogenerated chemiluminescence, electrochemically generated intermediates undergo a highly exergonic reaction to produce an electronically excited state that then emits light. ECL excitation is caused by energetic electron transfer (redox) reactions of electrogenerated species. Such luminescence excitation is a form of chemiluminescence where one/all reactants are produced electrochemically on the electrodes.

ECL is usually observed during application of potential (several volts) to electrodes of electrochemical cell that contains solution of luminescent species (polycyclic aromatic hydrocarbons, metal complexes) in aprotic organic solvent (ECL composition).

ECL combines analytical advantages of chemiluminescent analysis (absence of background optical signal) with ease of reaction control by applying electrode potential. Enhanced selectivity of ECL analysis is reached by variation of electrode potential thus controlling species that are oxidized/reduced at the electrode and take part in the ECL reaction.

ECL generally uses ruthenium complexes, especially [Ru (Bpy)3]$^{2+}$ (which releases a photon at ~620 nm) regenerating with TPA (Tripropylamine) in a liquid phase or at a liquid-solid interface. It can be used as monolayer immobilized on an electrode surface (made for example of nafion, or special thin films made by the Langmuir-Blogett technique or the self-assembly technique) or as a co-reactant or more commonly as a tag and used in HPLC, Ru tagged antibody based immunoassays, Ru Tagged DNA probes for PCR etc, NADH or $H_2O_2$ generation-based biosensors, oxalate and organic amine detection and many other applications and can be detected from picomolar sensitivity to a dynamic range of more than six orders of magnitude. Photon detection is done with PMT or silicon photodiode or gold coated fibre-optic sensors. These modifications are included within the scope of the invention.

Solid Surface

Where the methods of the invention require immobilisation onto a solid surface, the surface may be any surface or support upon which it is possible to immobilise one of the components of step (a) or the labelled binding partner, including one or more of a solid support (e.g., glass such as a glass slide or a coated plate, silica, plastic or derivatized plastic, paramagnetic or non-magnetic metal), a semi-solid support (e.g., a polymeric material, a gel, agarose, or other matrix), and/or a porous support (e.g., a filter, a nylon or nitrocellulose membrane or other membrane). In some embodiments, synthetic polymers can provide a solid surface, including, e.g., polystyrene, polypropylene, polyglycidylmethacrylate, aminated or carboxylated polystyrenes, polyacrylamides, polyamides, polyvinylchlorides, and the like. In preferred embodiments, the solid surface comprises a microtitre immunoassay plate or other surface suitable for use in an ELISA.

The surface of the substrate or support may be planar, curved, spherical, rod-like, pointed, wafer or wafer-like, or any suitable two-dimensional or three-dimensional shape on which the second binding partner may be immobilised, including, e.g., films, beads or microbeads, tubes or microtubes, wells or microtitre plate wells, microfibers, capillaries, a tissue culture dish, magnetic particles, pegs, pins, pin heads, strips, chips prepared by photolithography, etc. In some embodiments, the surface is UV-analyzable, e.g., UV-transparent.

Immobilisation Tag/Binding Member

The immobilisation tag is intended to be bound by the binding member. As such, the interaction between the two is a specific binding mechanism.

Immobilisation may be achieved in any number of ways, known in the art, described herein, and/or as can be developed. For example, immobilisation may involve any technique resulting in direct and/or indirect association of the immobilisation tag with the binding member, including any means that at least temporarily prevents or hinders release of the immobilisation tag (and the attached component) into a surrounding solution or other medium. The means can be by covalent bonding, non-covalent bonding, ionic bonding, electrostatic interactions, Hydrogen bonding, van der Waals forces, hydrophobic bonding, or a combination thereof. For example, immobilisation can be mediated by chemical reaction where the immobilisation tag contains an active chemical group that forms a covalent bond with the binding member. For example, an aldehyde-modified support surface can react with amino groups in protein receptors; or amino-based support surface can react with oxidization-activated carbohydrate moieties in glycoprotein receptors; a support surface containing hydroxyl groups can react with bifunctional chemical reagents, such as N,N disuccinimidyl carbonate (DSC), or N-hydroxysuccinimidyl chloroformate, to activate the hydroxyl groups and react with amino-containing receptors. In some embodiments, support surface of the substrate may comprise animated or carboxylated polystyrenes; polyacrylamides; polyamines; polyvinylchlorides, and the like. In still some embodiments, immobilization may utilize one or more binding-pairs to bind or otherwise attach the immobilisation tag to the binding member, including, but not limited to, an antigen-antibody binding pair, hapten/anti-hapten systems; a avidin-biotin binding pair; a streptavidin-biotin binding pair, a folic acid/folate binding pair; photoactivated coupling molecules, and/or double stranded oligonucleotides that selectively bind to proteins, e.g., transcriptional factors.

The skilled person will appreciate that a number of the immobilisation options described above are also suitable for immobilising any one of the components of step (a) without the need for an immobilisation tag.

The binding member may be immobilised on the surface of a reaction container or to beads which are added to the first reaction container (e.g. superparamagnetic polystyrene beads—Dynabeads M-450). Once binding of the immobilisation tag to the binding member is achieved, unbound reactants can be washed from the immobilised component. Detection of the component is then possible via the labelled binding partner.

Preferably, the binding member has a higher affinity for the immobilisation tag than for any of the other components used in the methods of the invention, in the sense that it binds preferentially to the immobilisation tag. The skilled person will appreciate that the same is true vice versa, i.e. the immobilisation tag preferentially binds to the binding member.

Preferably the binding member has a binding affinity (Kd) of less than $10^{-6}$M, i.e. $10^{-7}$M, $10^{-8}$M, $10^{-9}$M, $10^{-10}$M, $10^{-11}$M, $10^{-12}$M or even $10^{-13}$M or less towards the immobilisation tag. Preferably, the binding member has a binding affinity (Kd) of less than $10^{-9}$M, i.e., $10^{-10}$M, $10^{-11}$M, $10^{-12}$M or $10^{-13}$M towards the immobilisation tag.

Preferably the immobilisation tag is selected from the group consisting of a polyarginine tag (Arg-tag), polyhistidine tag (His-tag), FLAG-tag, Strep-tag, c-myc-tag, S-tag, calmodulin-binding peptide, cellulose-binding domain, SBP-tag chitin-binding domain, glutathione S-transferase-tag (GST), maltose-binding protein, transcription termination anti-termination factor (NusA), *E. coli* thioredoxin (TrxA) and protein disulfide isomerase I (DsbA).

Order of Contact with Solid Surface

Where the embodiments of the invention require immobilising any one of the components of step (a) onto a solid surface, the immobilisation may occur either before the components of step (a) are combined; after the components have been combined; after the components have been combined and the sample has been incubated for a finite period of time; or after the sample has been exposed to the labelled binding partner.

For example, step (a) may be carried out first and the ubiquitination reaction allowed to proceed for a finite period of time. The sample may then be exposed to the solid surface or to the labelled binding partner. If it is exposed to the solid surface first, it will then be exposed to the labelled binding partner. If it is exposed to the labelled binding partner first, it will then be exposed to the solid surface. Exposure to the solid surface in either case allows for the immobilisation of any one of the components of step (a).

Alternatively any one of the components of step (a) may be immobilised to the solid surface first, then the remainder of the components of step (a) combined in a sample which is in contact with the solid surface. The ubiquitination reaction is allowed to proceed and then exposed to the labelled binding partner.

In one preferred embodiment, the methods of the invention involve completing step (a), allowing the reaction to proceed for a finite period of time, completing step (b), and then exposing the sample to a solid surface.

Screening for Modulators of Ubiquitination

One of the components of the sample may be a potential modulator of ubiquitination. By measuring levels of ubiquitination both in the presence and absence of a candidate modulator, it is possible to assess the effect that any compound has on ubiquitination. The modulator may affect one or more of the components involved in ubiquitination. For example, the modulator may affect one or more of E1, E2 or E3 directly or may affect the binding of these components to other components of the ubiquitination pathway. The possibility of using different substrates allows for modulators of ubiquitin ligase activity to be screened for their differing effects on different substrates.

Modulator

A modulator may be a compound which can increase or decrease the level of ubiquitination. By potential modulator it is meant that the compound either acts or is suspected to act as a modulator.

As E3 ligases comprise multiple protein components, all of which form interactions with neighbouring components as well as with other members of the ubiquitination pathway, the ubiquitin ligase provides many targets for potential modulators of activity. Potential areas of the ubiquitination pathway which may be targeted by modulators of ubiquitination may include but are not limited to E3 ligase interaction with the substrate, interaction between ubiquitin and the substrate, interactions between two protein subunits of the ubiquitin ligase, interactions between E1 enzyme and E2 enzyme, interaction between E2 enzyme and ubiquitin ligase, or a combination of these.

The ability of the methods of the present invention to provide an accurate and reliable ubiquitination assay allows for a large number of potential modulators to be screened effectively.

Controls

To detect ubiquitination using the methods of the invention a reference point is typically needed i.e. a control. Analysis of a control sample gives a standard level of ubiquitination and against which the sample can be compared.

A negative control sample may contain all components of the sample with a non-functional protein component that is essential for the reaction to take place. The negative control may also contain all but one of the components required for ubiquitination, e.g. ATP may be omitted from the reaction. Positive controls may also be used as a reference point to which a sample can be compared. For example, a positive control sample may contain components which give a known amount of ubiquitination over a set period of time.

Potential modulators may up-regulate or down-regulate the level of ubiquitination. To detect such up- or down-regulation, a reference point is typically needed i.e. a control. Analysis of a control sample gives a standard level of ubiquitination and therefore a standard level of ubiquitination against which the modulated sample can be compared.

A positive control sample may contain all components of the sample but lack the potential modulator. This can then provide a basal level of ubiquitination in the absence of the potential modulator. Negative controls may also be used as a reference point to which a sample containing a modulator can be compared. A negative control sample may contain a modulator which has a known effect on the level of ubiquitination.

High Throughput Screening

Optionally the methods of assaying provided by the invention may be used in the high throughput screening of potential modulators of ubiquitination. High throughput screening is a method of screening which allows high numbers of similar tests to be performed in parallel quickly and efficiently. High throughput screening may be achieved using a multi-well plate, which are well known in the art and include but are not limited to plates which comprise a grid of, for example, 96, 384, 1536, or 3456 small, open wells. These wells can each contain different samples to be tested, and the test can be conducted on all of the samples contemporaneously.

Kits

The invention also includes kits which are suitable for carrying out the methods of the invention. Preferably the kits will comprise the components required for step (a) of the methods of the invention as described above in addition to a labelled binding partner. The variations and preferred embodiments described in relation to these components are also intended to be reflected in preferred embodiments of the kits. That is, if a particular component is preferred for the methods of the invention, it is also preferred for the kits.

General

The term "comprising" encompasses "including" as well as "consisting" e.g. a composition "comprising" X may consist exclusively of X or may include something additional e.g. X+Y.

The term "about" in relation to a numerical value x means, for example, x+10%.

The word "substantially" does not exclude "completely" e.g. a composition which is "substantially free" from Y may be completely free from Y. Where necessary, the word "substantially" may be omitted from the definition of the invention.

Various aspects and embodiments of the present invention will now be described in more detail by way of example.

BRIEF DESCRIPTION OF THE DRAWINGS

FIG. 1: List of complexes, proteins, manufacturing names, expression systems and accession numbers used throughout this study.

FIG. 12 (b): 'Live UbcH3—ECL. Used Anti-HA capture for E2 (Millipore, 05-904(HA), 1/500); 12.5 to 200 nM E1; 6.25 to 200 mM E2; 2 μM Ub; 500 μM ATP; streptavidin sulfo tag (MSD, R32AD-1, 1 μg/ml). Initial 'live' assays (60 minute incubation) for UbcH3 show good signal (>1500000) at high E1 concentrations. Max signal appears to be dependent on the amount of E1 in the assay. HA and c-Myc UbcH3's perform better than the FLAG version.

tested using ECL platform. Used anti-FLAG capture for p27 (Millipore, MAB3118 (FLAG), 1/500 to 1/4000); E1:E2:E3 based on Xu publication (40 nM E1:5 µM E2:40 nM E3; biotinylated Ub (10 µm), 500 µM ATP; streptavidin sulfo tag (MSD, R32AD-1, 1 µg/ml). Signal indicative of the presence of Ubiquitinated p27 has been observed.

Figure 14:
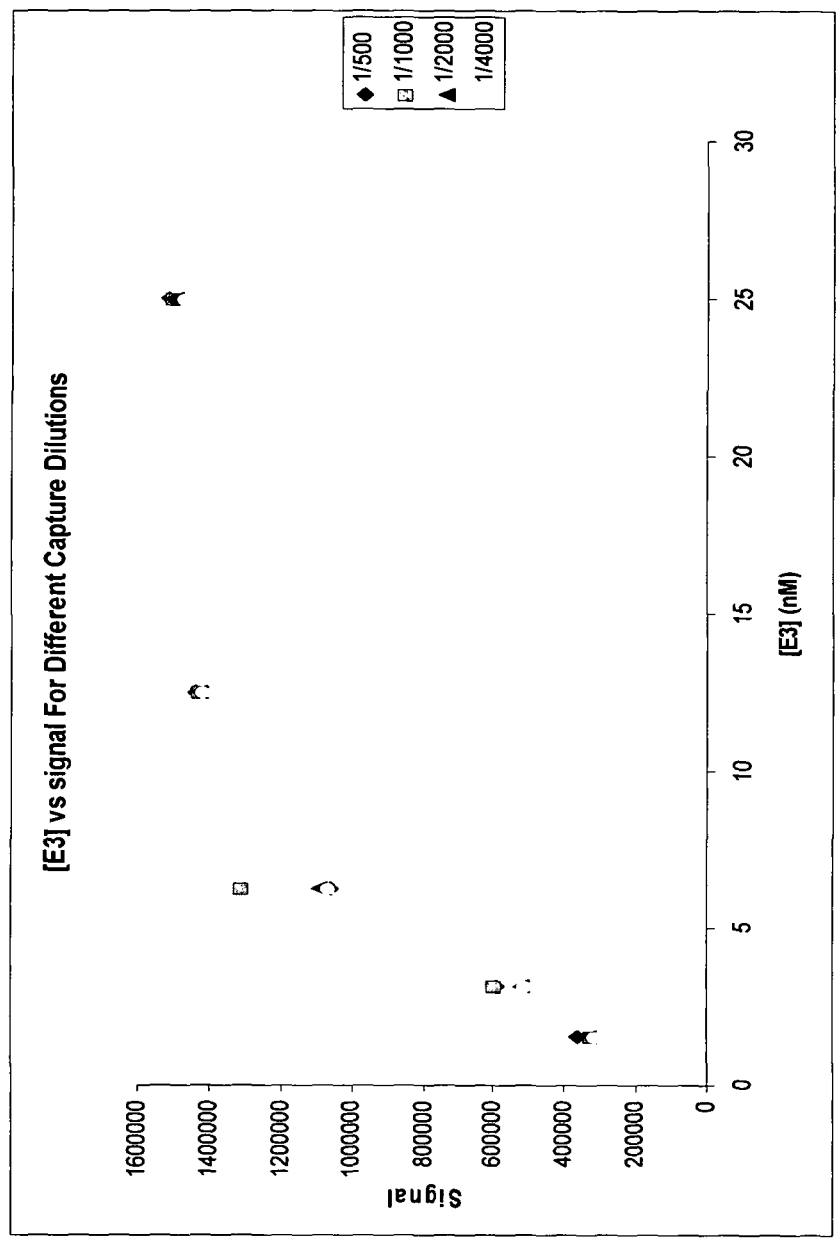
FIG. 14 (a) Pre-incubated $SCF^{skp2}$—ECL. Used pre-incubated E1/E2/E3/p27/Ub/ATP (24 hour incubation)

FIG. 14 (b) 'Live' SCF$^{skp2}$—ECL (b). Used 'live' E1/E21E3/p27/Ub/ATP (60 minute incubation) tested using ECL platform. Used c-Myc and HA capture for p27 (05274 (c-Myc), 05-904 (HA), 1/500); 5 nM E1; 4 to 1000 nM E2 (HA or c-Myc); 50 nM E3; 3.125 to 100 nM p27; 2 µM Ub; 500 µM ATP; streptavidin sulfo tag (MSD, R32AD-1, 1 µg/ml). Signal indicative of the presence of ubiquitinated p27 has been observed.

Figure 15:
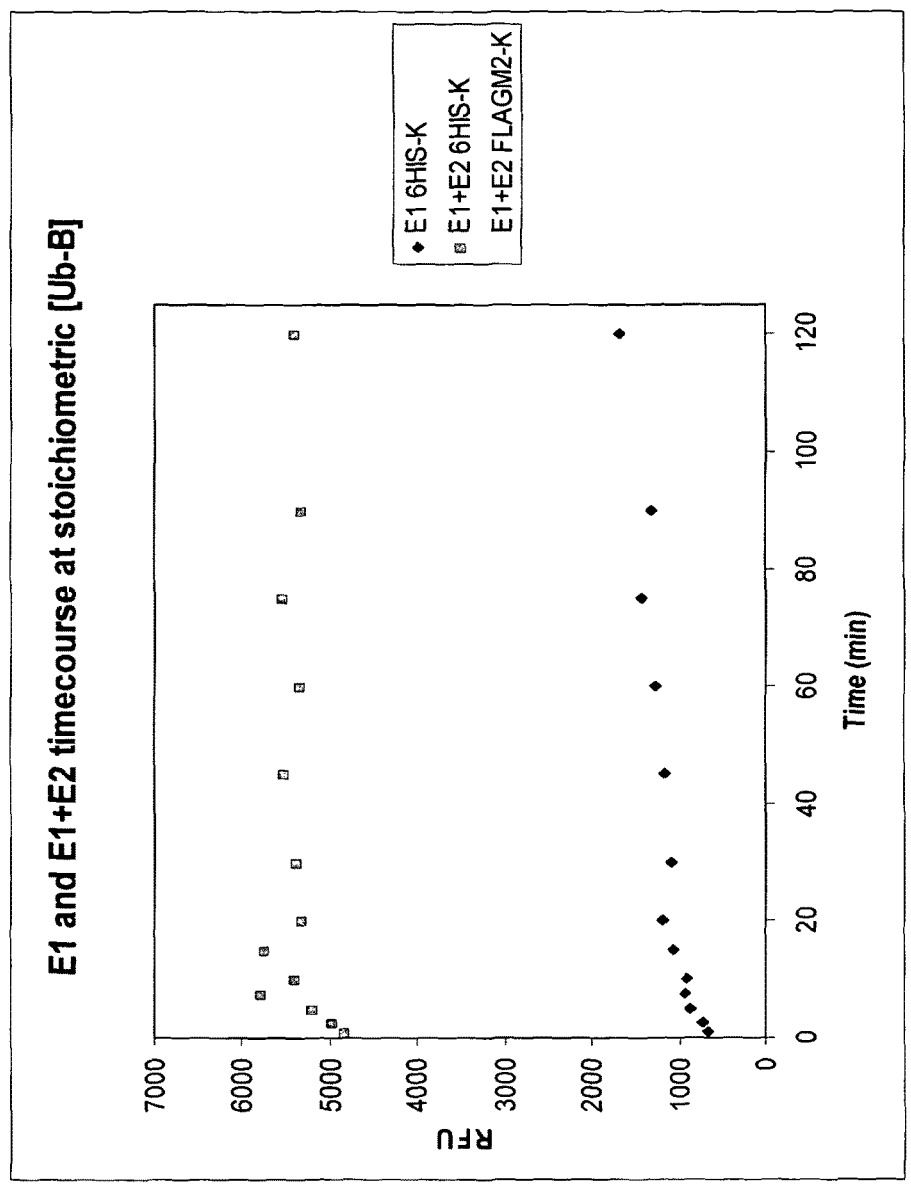

FIG. 15: Ube1 and Ube1+UbcH3 assay timecourse—HTRF. E1 assay: 1 µM NiNTA Ube1+1 µM Ub+2 mM ATP. E1+E2 assay: 1 µM NiNTA Ube1+1 µM Flag UbcH3+1 µM Ub+2 mM ATP. Both the E1 and E1+E2 assays appear to reach completion after a very short time period, which is in line with the ECL data. Used Anti-6HisK for E1+E2 detection; Anti-FLAG-K for E2; biotinylated Ub; streptavidin XLent! for biotin. Impossible to monitor in current format. Samples were diluted to 10 nM E1 in ×1 reaction buffer (RB).

FIG. 16: E2 and ubiquitin titration (Ube1+UbcH3 assay)—HTRF. 'Live' Ube1+UbcH3 assay—100 nM E1/varying [E2]/200 nM Ub/2 mM ATP. 60 minute room temperature incubation. 'Live' Ube1+UbcH3 assay 100 nM E1/1 µM E2/varying [Ub]/2 mM ATP, 60 min room temperature incubation. Samples diluted to 10 nM E1 in ×1 reaction buffer. Used Anti-6His-K for E1+E2 detection; anti FLAG K for E2 detection; biotinylated Ub; streptavidin XLent! for biotin. Optimal E1, E2 and Ubiquitin conditions are 100 nM Ube1/1 µM UbcH3/400 nM Ub.

Figure 17:
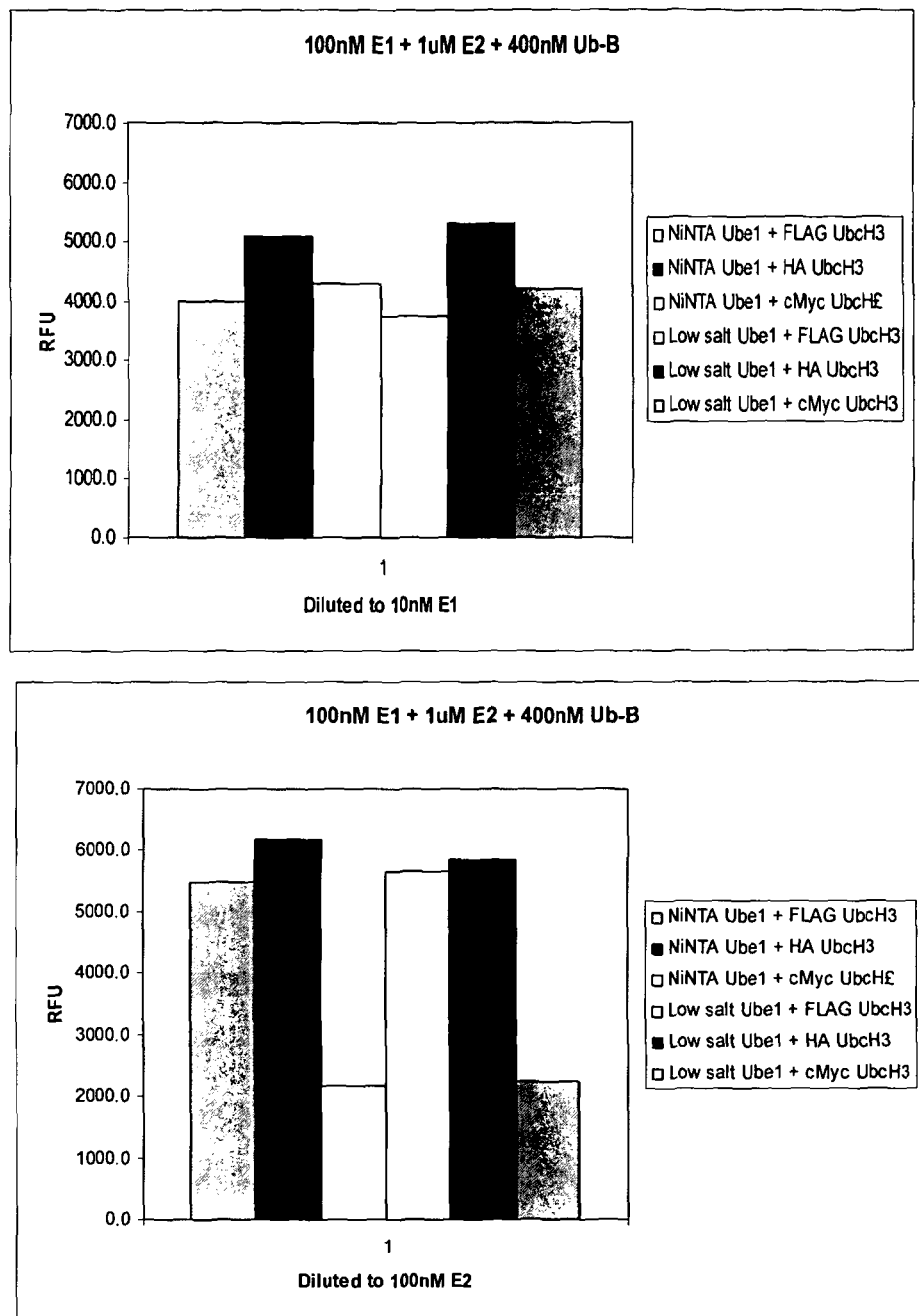

FIG. 17: Ube1 and UbcH3 construct comparison (E1+E2 assay)—HTRF. 'Live Ube1 and UbcH3 assay: E1/E2/Ub/2 mM ATP, varying E1 and E2 constructs at: 100 nM E1+1 µM E2+400 nM Ub. Used anti-6His-K for E1+E2 detection; anti FLAG-K, anti HA-K or anti cMyc-K for E2 detection; biotinylated Ub; streptavidin XLent! for biotin. NiNTA-Ube1 and HA-UbcH3 in a ratio of 100 nM E1+1 µM E2+400 nM Ub assayed at 2 mM ATP; and diluted 10-fold gives the best FRET-signal.

Figure 18:
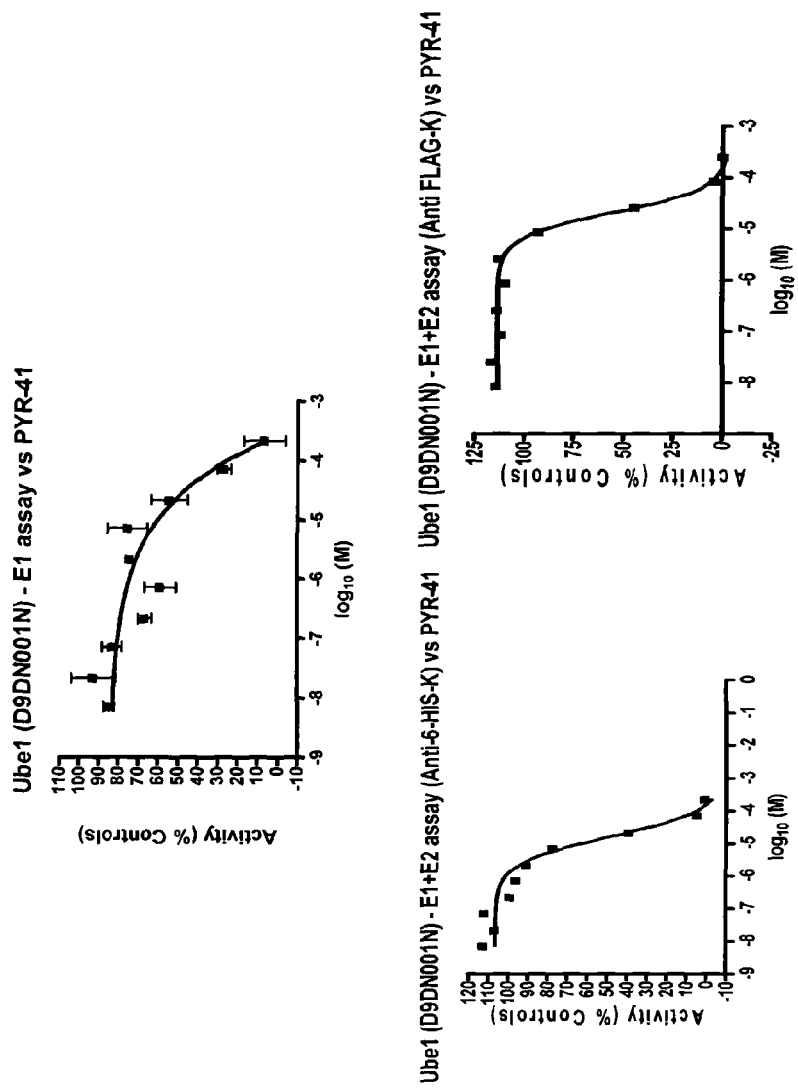

FIG. 18: Ube1 Inhibitor study PYR41 in E1 and E1+E2 assay HTRF. Inhibitor study: 30 minutes pre-incubation with PYR-41. Assays were immediately diluted followed by addition of 2 mM ATP. Titration of PYR-41 (Calbiochem 662105) from 300 µM to 0.01 µM, IC$_{50}$=43 µM—E1 (1 µM E1, 2 µM Ub (Anti-6His-K). IC$_{50}$=16 µM E1/E2 (100 nM E1, 1 µM E2, 400 nM Ub (Anti-6-HIS-K)) IC$_{50}$=20 µM E1/E2 (as above Anti-FLAG-K). BiogenNova quote IC$_{50}$ value as ~5 µM.

FIG. 19: Western blot—Anti phospho p27—E3 assay. Incubated E1/E2/E3/p27Ub/ATP, Anti-phospho-p27 antibody (Millipore 06-996 1/1000). Anti species HRP (Cell Signalling #7074 1/1000). Definite shift in the position of the phospho-p27 band consistent with the poly-ubiquitination of p27.

Figure 20:
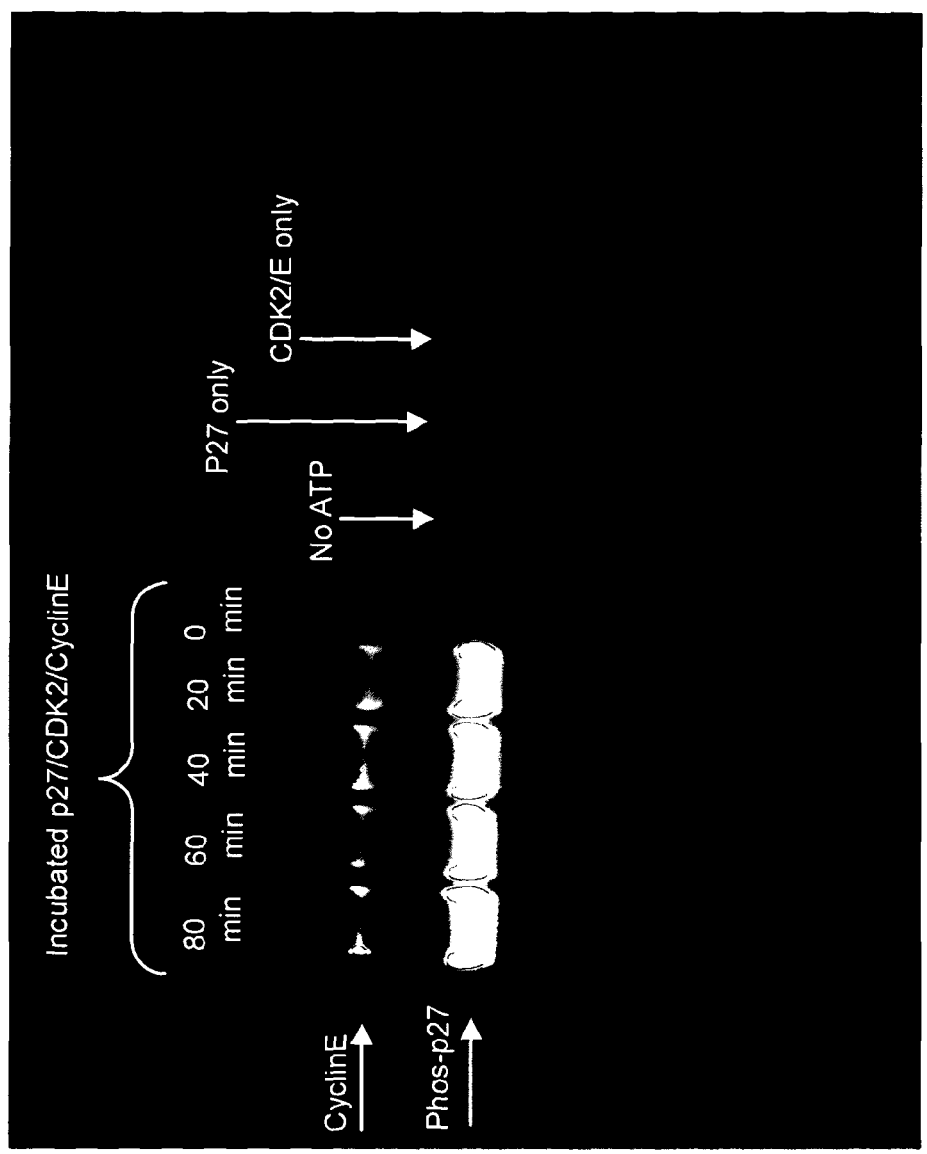

FIG. 20: Western blot—Anti Phospho p27. Incubated FLAG-p27/CDK2/cyclinE with CDK2/cyclinE (0.1:0.1 mg/ml) and Mg-ATP (2 µM), anti phospho-p27 antibody (Millipore 06-996 1/1000). Anti species HRP (Cell signalling #7074 1/1000). Incubation of p27/CDK2/CyclinE with CDK2/cyclinE and ATP leads to a significant increase in the amount of phospho p27 as detected by Western blot. Max. signal is seen even after 20 minutes.

Figure 21:
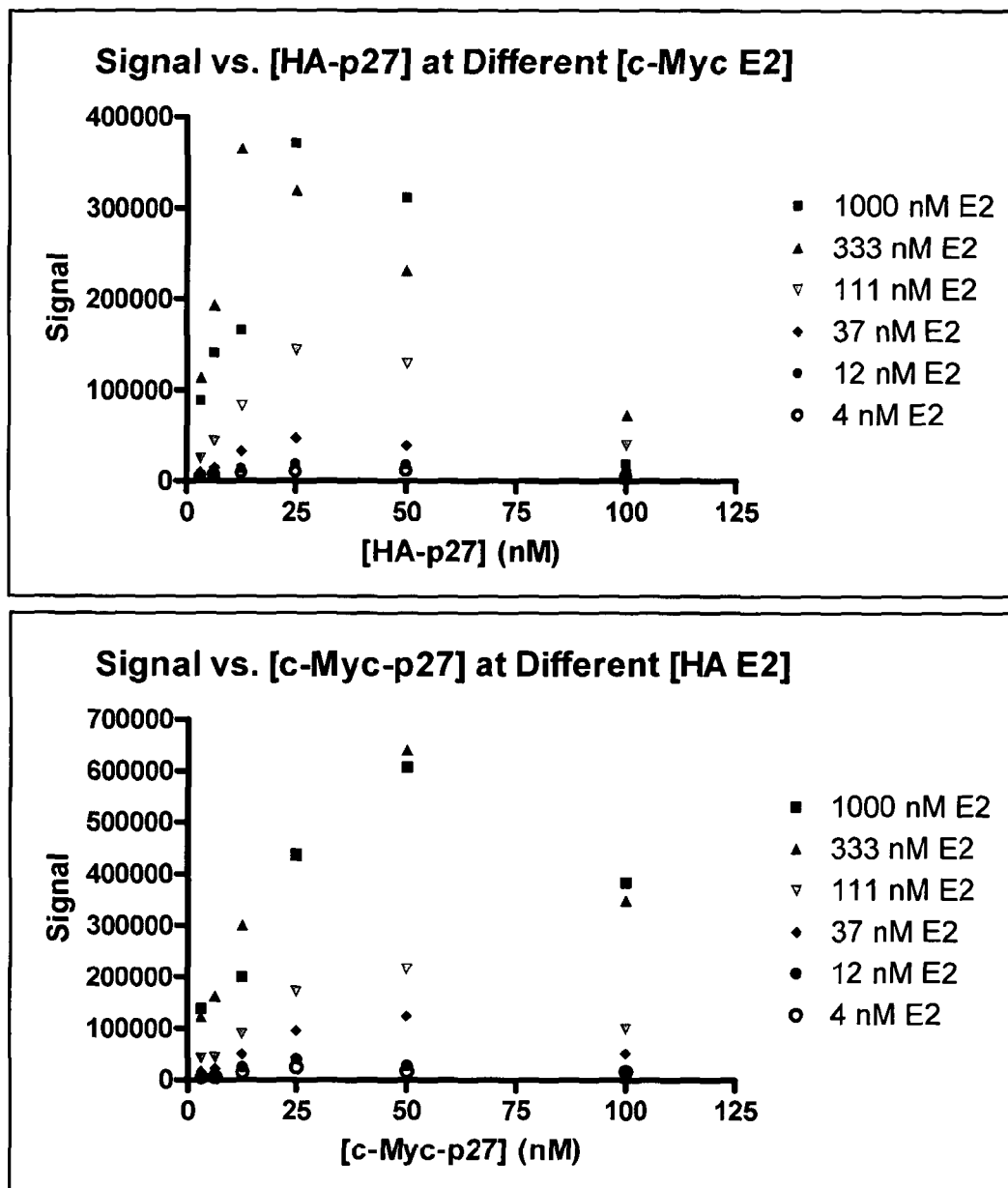

FIG. 21: 'Live' SCF$^{Skp2/Cks1}$ Assay—ECL. 'Live' E1/E2/E3/p27/Ub/ATP (60 minute incubation) tested using ECL platform. No FLAG tagged E2/p27 due to problems encountered in E2 assay. Used c-Myc and HA capture for p27 (Millipore 05-274 (c-Myc), 05-904(HA), 1.500); 5 nM E1; 4 to 1000 nM E2 (HA or c-Myc); 50 nM E3/Cks1; 3.125 to 100 nM p27 (1-IA of c-Myc); 2 µM Ub; 500 µM ATP; streptavidin sulfo tag (MSD, R32AD-1 1 µg/ml). Signal indicative of the presence of Ubiquitinated p27 has been observed. c-Myc tagged p27 gives significantly higher signal. Optimum signal at 50 nM p27, 1 µM E2.

Figure 22:
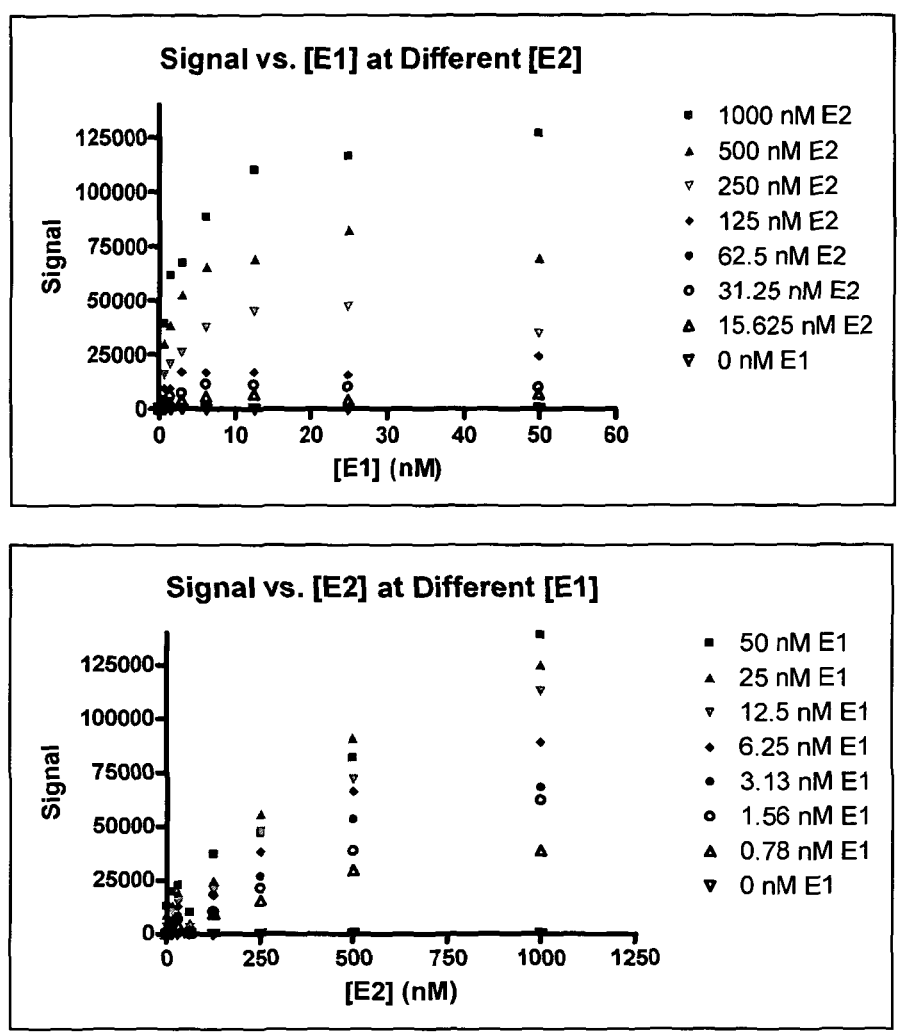
Figure 22:
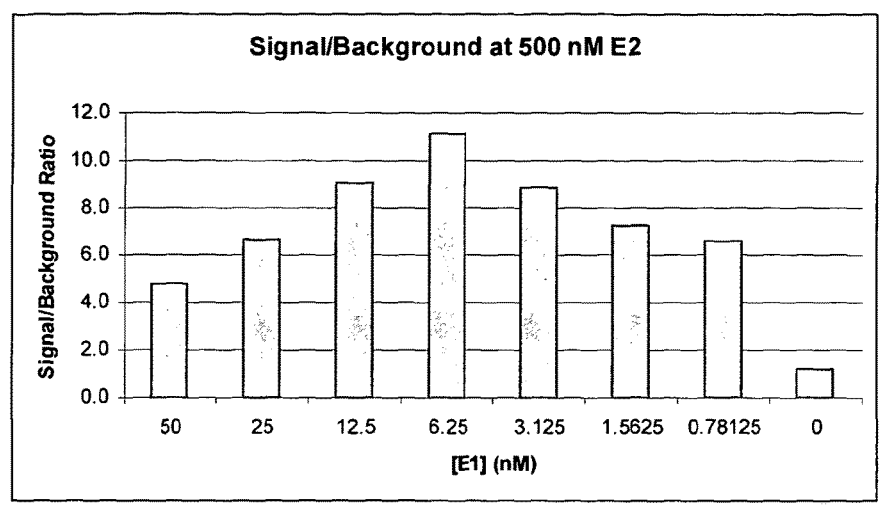

FIG. 22: 'Live' SCF$^{Skp2/Cks1}$ Assay—ECL E1 vs. E2 titration. Used 60 minute incubation; 25 nM c-Myc p27; anti c-Myc capture for p27 (Millipore 05-274, 1/500); 0.78 to 50 nM E1; 15 to 1000 nM E2 (HA); 25 nM E3/Cks1; 2 µM Ub; 500 µM ATP; streptavidin sulfo tag (MSD, R32AD-1, 1 µg/ml). E1—hyperbolic increase in signal with [E1]. Optimum signal after 25 nM. However, optimum signal/background at 6.25 nM E1. E2—linear increase in signal with [E2]. Final assay concentration set at 1 µM.

Figure 23:
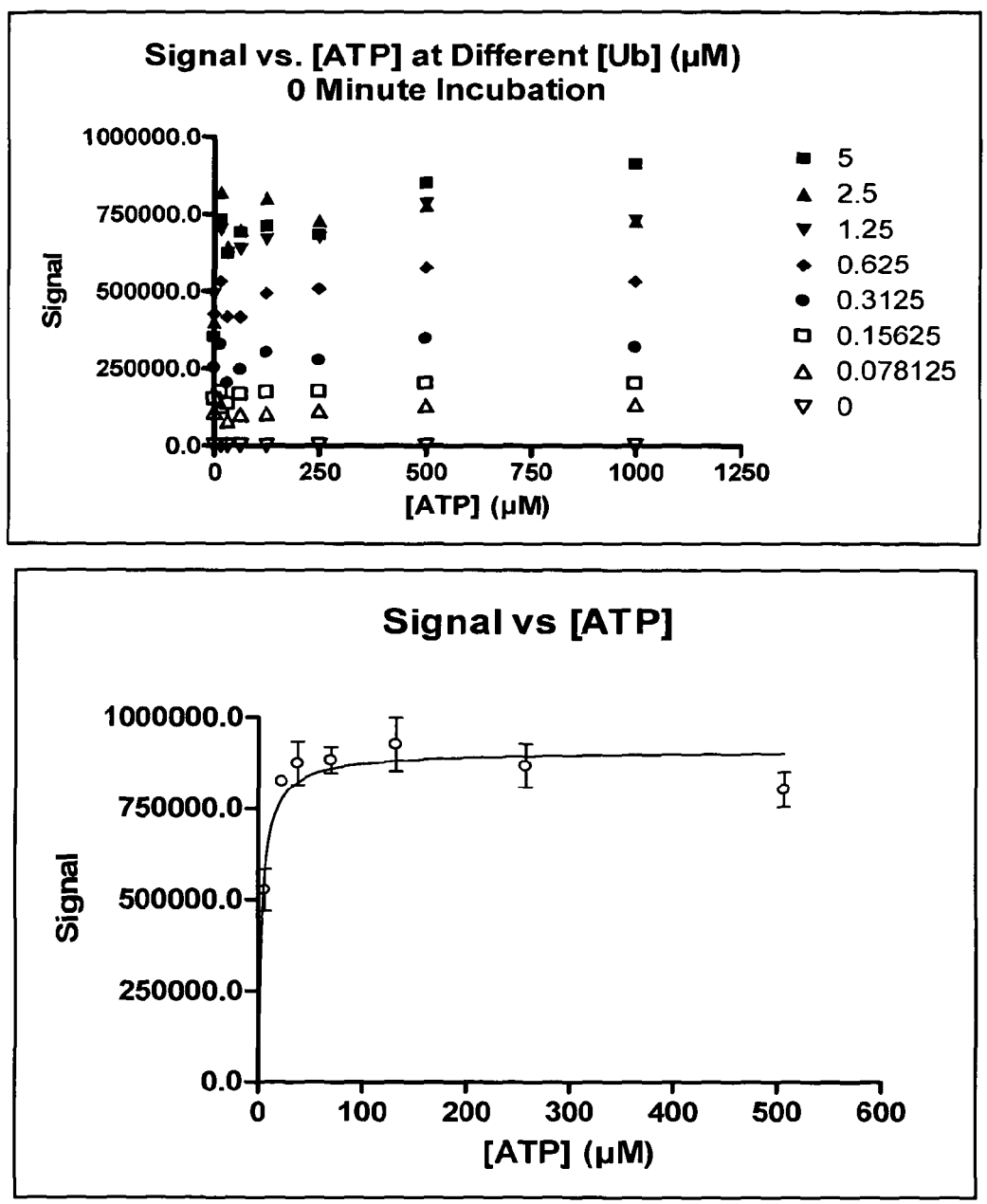

FIG. 23 (a): 'Live' SCF$^{Skp2/Cks1}$ Assay—ECL ubiquitin titration. Used 60 minute incubation; 25 nM c-Myc p27; anti c-Myc capture for p27 (Millipore 05-274, 1/500); 5 nM E1; 1 µM E2 (HA); 25 nM E3/Cks1; 5 to 0.08 µM Ub; 1000 to 15 µM ATP; streptavidin sulfo tag (MSD, R32AD-1, 1 µg/ml). Hyperbolic increase in signal with [Ub]. Optimum signal after 2 µM ubiquitin. Largely dependent of ATP concentration. K$_m$ values between 0.46 and 0.58 µM. Final assay concentration is set at 2 µM.

FIG. 23 (b): 'Live' SCF$^{Skp2/Cks1}$ Assay—ECL ATP titration. Used 60 minute incubation; 25 nM c-Myc p27; anti c-Myc capture for p27 (Millipore 05-274, 1/500); 5 nM E1; 1 µM E2 (HA); 25 nM E3/Cks1; 2 µM Ub; 1000 to 7 µM ATP; streptavidin sulfo tag (MSD, R32AD-1, 1 µg/ml). Initial experiments indicated a high signal which was independent of ATP concentration (lowest [ATP] of 21 µM) indicative of tight binding. Repeat experiment showed similar profile with only a moderate decrease at 7 µM ATP. K$_m$ estimated at 4 µM. Final assay concentration set at 100 µM.

Figure 24:
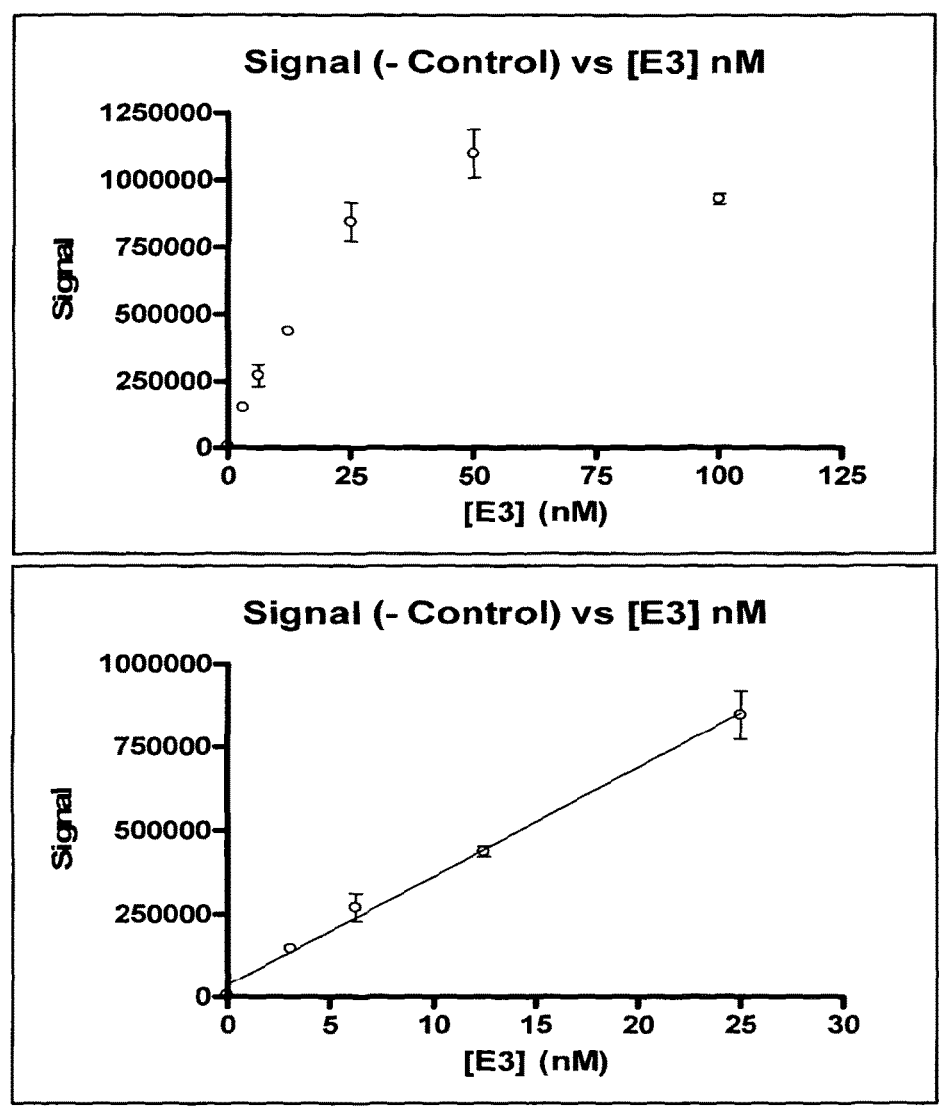

FIG. 24: 'Live' SCF$^{Skp2/Cks1}$ Assay—ECL E3 tetramer/Cks1 titration. Used 60 minute incubation; 25 nM c-Myc p27; anti c-Myc capture for p27 (Millipore 05-274, 1/500); 5 nM E1; 1 µM E2 (HA); 3 to 100 nM E3/Cks1; 2 µM Ub; 100 µM ATP; streptavidin sulfo tag (MSD, R32AD-1, 1 µg/ml). Hyperbolic increase in signal with [E3/Cks1]. Optimum signal at 50 nM E3/Cks1. Re-plotting the data between 0 and 25 nM E3/Cks1 indicates a linear relationship. Final assay concentration set at 25 nM.

Figure 25:
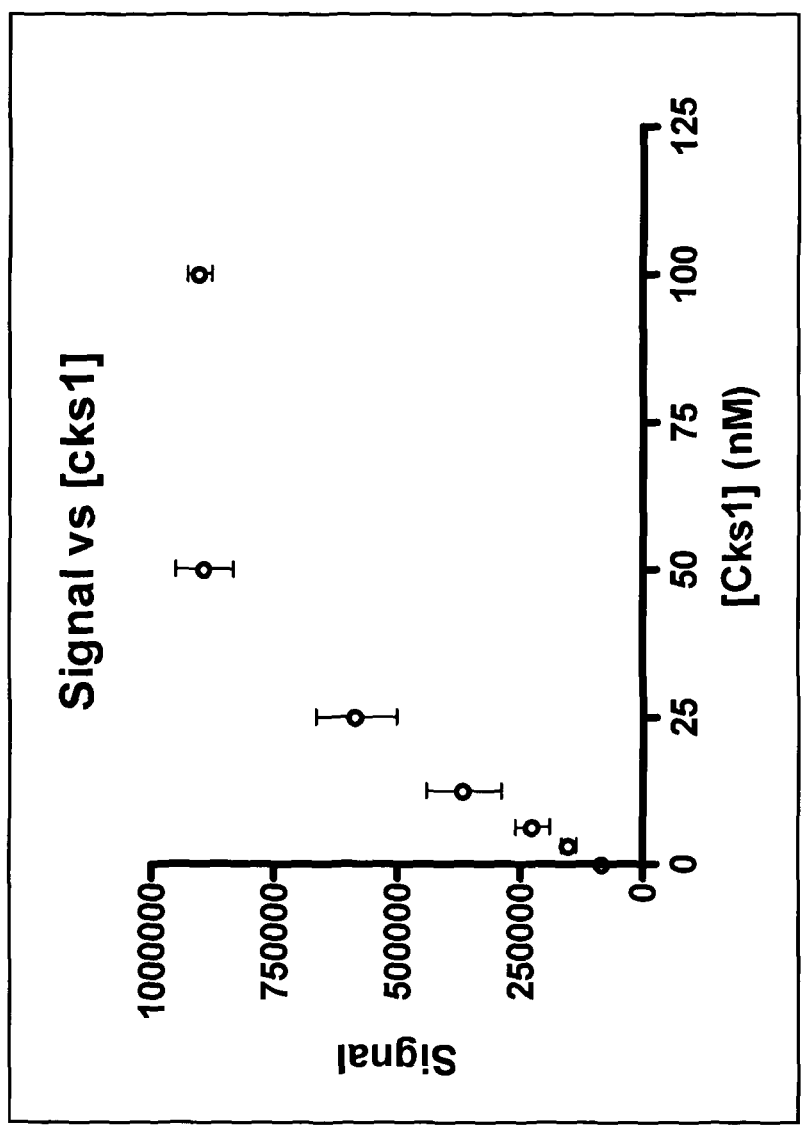

FIG. 25: 'Live' SCF$^{Skp2/Cks1}$ Assay—ECL Cks1 titration—FIXED E3 tetramer. Used 60 minute incubation; 25 nM c-Myc p27; anti c-Myc capture for p27 (Millipore 05-274, 1/500); 5 nM E1; 1 µM E2 (HA); 25 nM E3 tetramer; 3 to 100 nM Cks1; 2 µM Ub; 100 µM ATP; streptavidin sulfo tag (MSD, R32AD-1, 1 µg/ml). Linear increase in signal with [Cks1] up to 50 nM followed by plateau. Optimum signal at 50 nM Cks1. Final assay concentration set at 25 nM.

Figure 26:
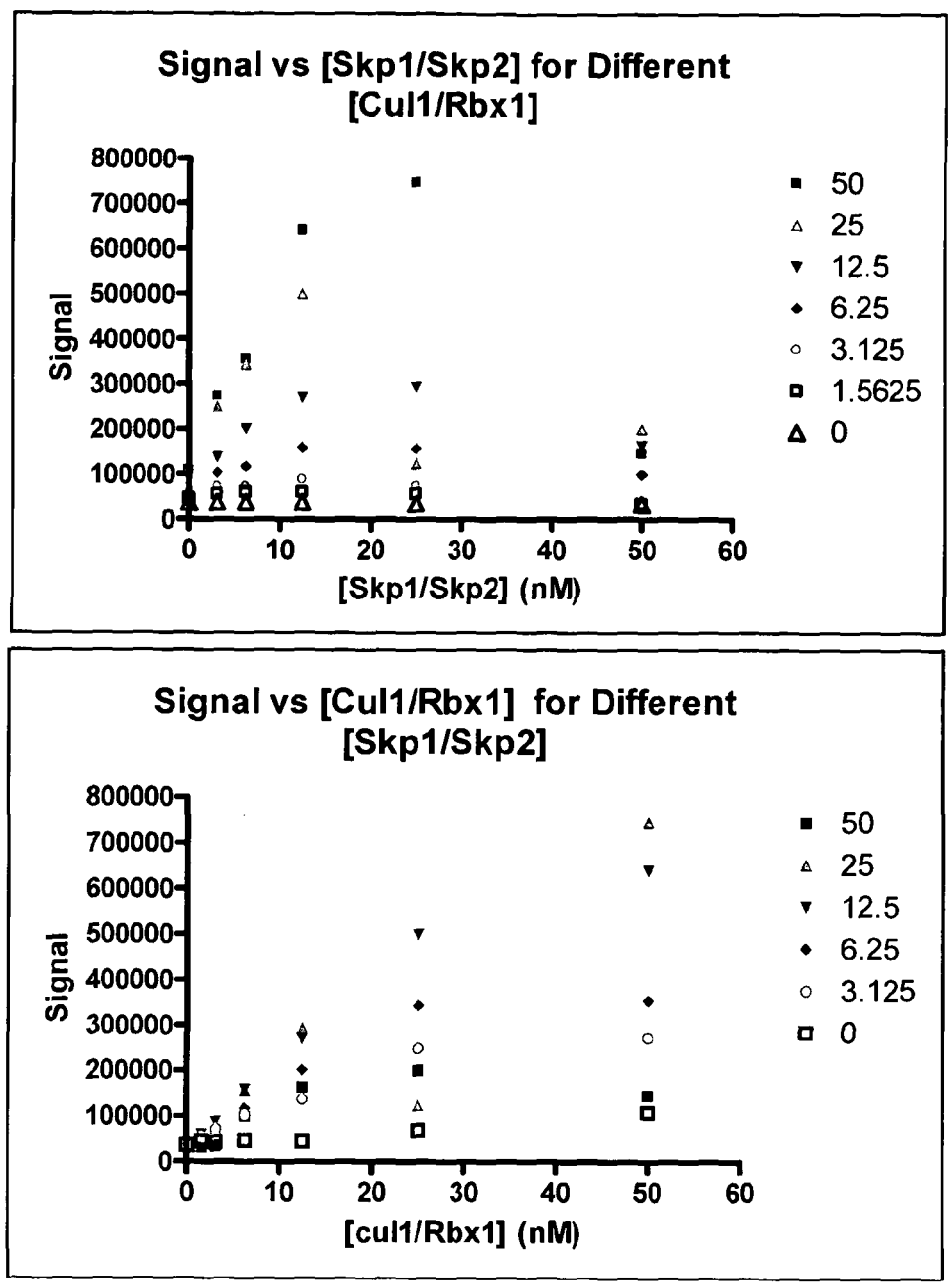

FIG. 26: 'Live' SCF$^{Skp2/Cks1}$ Assay—ECL Skp1/Skp2 vs Cul1/Rbx1 titration. 'Live' E1/E2/E3/p27/Ub/ATP (60 minute incubation) tested using ECL platform. Co-expressions of Skp1/Skp2 and Cul1/Rbx1 instead of tetramer. Used c-Myc and HA capture for p27 (Millipore 05-274 (c-Myc), 05-904 (HA), 1/500); 5 nM E1; 1 µM E2 (HA or c-Myc), 25 mM Cks1; 25 nM p27; 2 µM Ub; 100 µM ATP; 50 to 1.5 nM Skp1/Skp2; 50 to 3.1 nM Cul1/Rbx1; streptavidin sulfo tag (MSD, R32AD-1, 1 µg/ml). Optimum signal at 50 nM Cul1/Rbx1 and 25 nM Skp1/Skp2.

FIG. 27: Comparison of the Skp1/Skp2 and Cul1/Rbx1 co-expressions with the Skp1/Skp2/Cul1/Rbx1 tetramer. Indicates very little difference in max signal strength.

Figure 28:
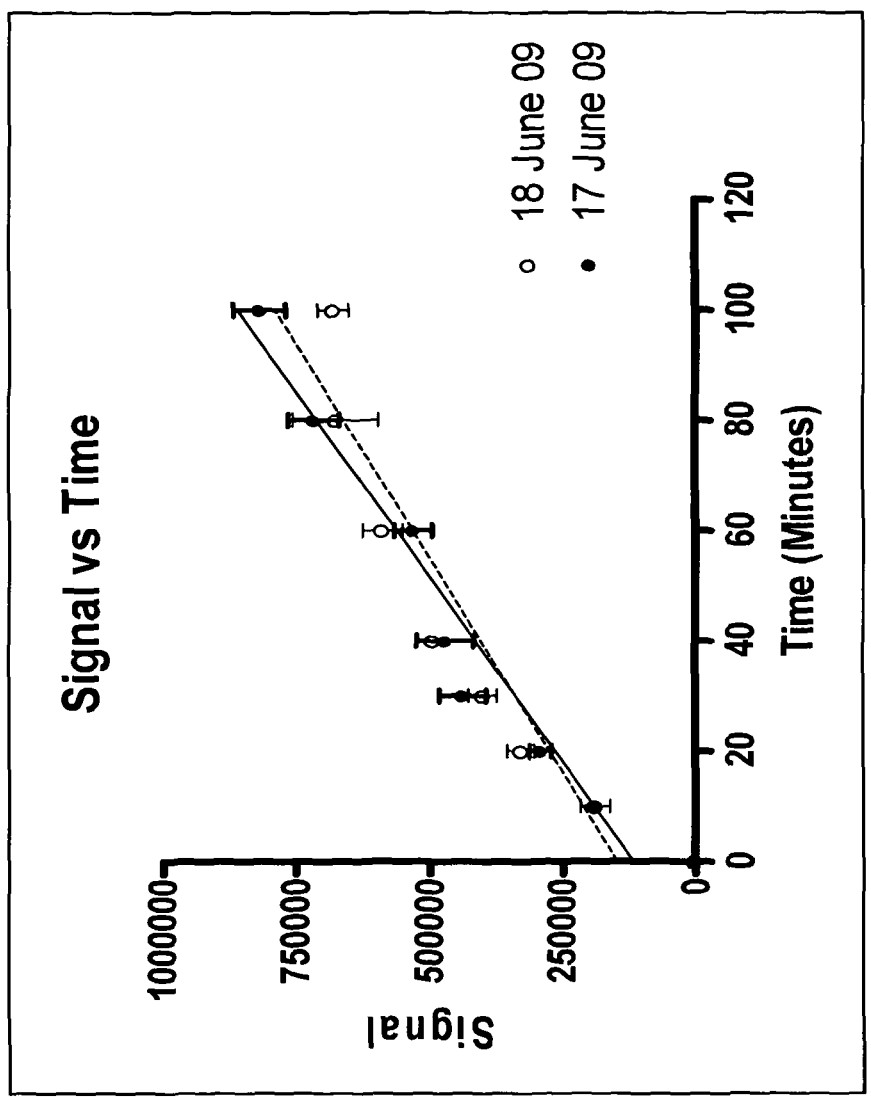

FIG. 28: 'Live' SCF$^{Skp2/Cks1}$ Assay—ECL time course. Used 10 to 100 minute incubation. 25 nM c-Myc p27; anti c-Myc capture for p27 (Millipore 05-274, 1/500); 5 nM E1; 1 μM E2 (HA); 25 nM E3 tetramer; 25 nM Cks1; 2 μM Ub; 100 μM ATP; streptavidin sulfo tag (MSD, R32AD-1, 1 μg/ml). Linear increase in signal with time up to 100 minutes. Experiment repeated to check reproducibility. Comparable signal strength/profile seen for both experiments. High y-intercept may be due to 'stop' method. Final reaction time set at 60 minutes.

FIG. 29: 'Live' SCF$^{Skp2/Cks1}$ Assay—ECL Z'. Used 60 minute incubation; 25 nM cMyc p27; anti c-Myc capture for p27 (Millipore 05-274, 1/500); 5 nM E1; 1 μM E2 (HA); 25 nM E3 tetramer; 25 nM Cks 1; 2 μM Ub; 100 μM ATP; Streptavidin sulfo tag (MSD, R32AD-1, 1 μg/ml). 1 sector of positive controls with one sector of negative (no Ubiquitin) controls. Total of 3 independent experiments. Signal strength, signal/background ratio, positive control % CV and Z' all within acceptable limits. Some variation in signal strength.

Figure 30:
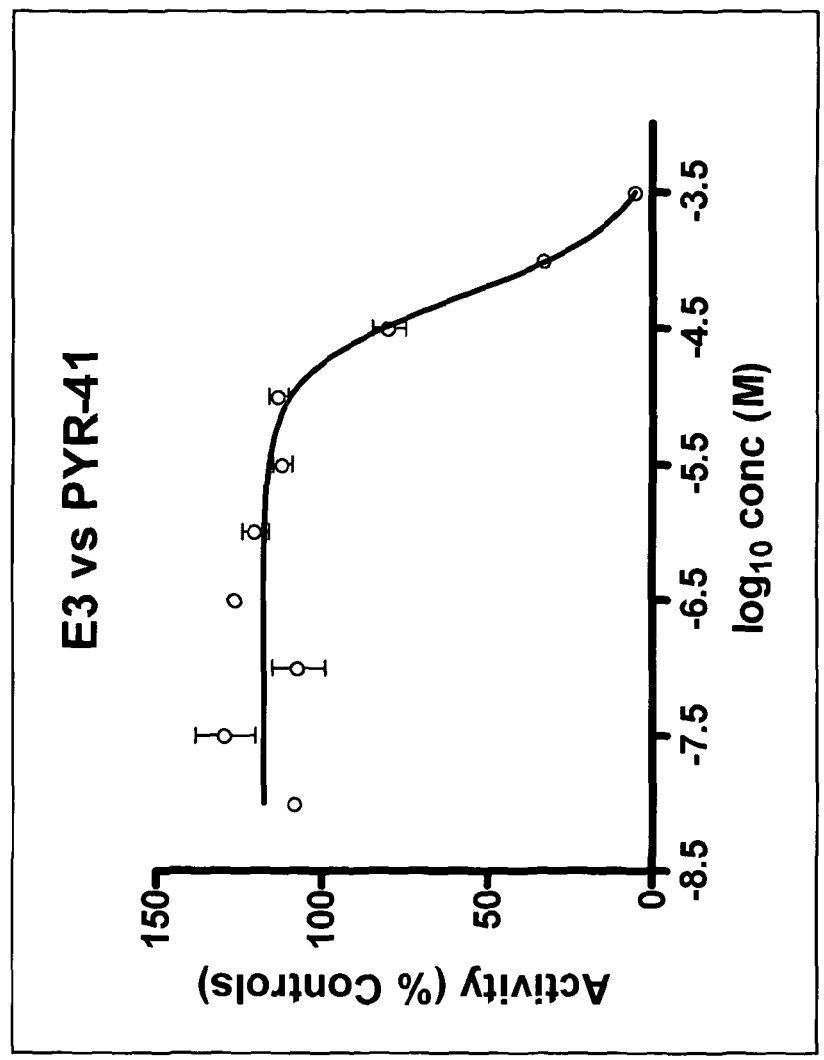
Figure 30:
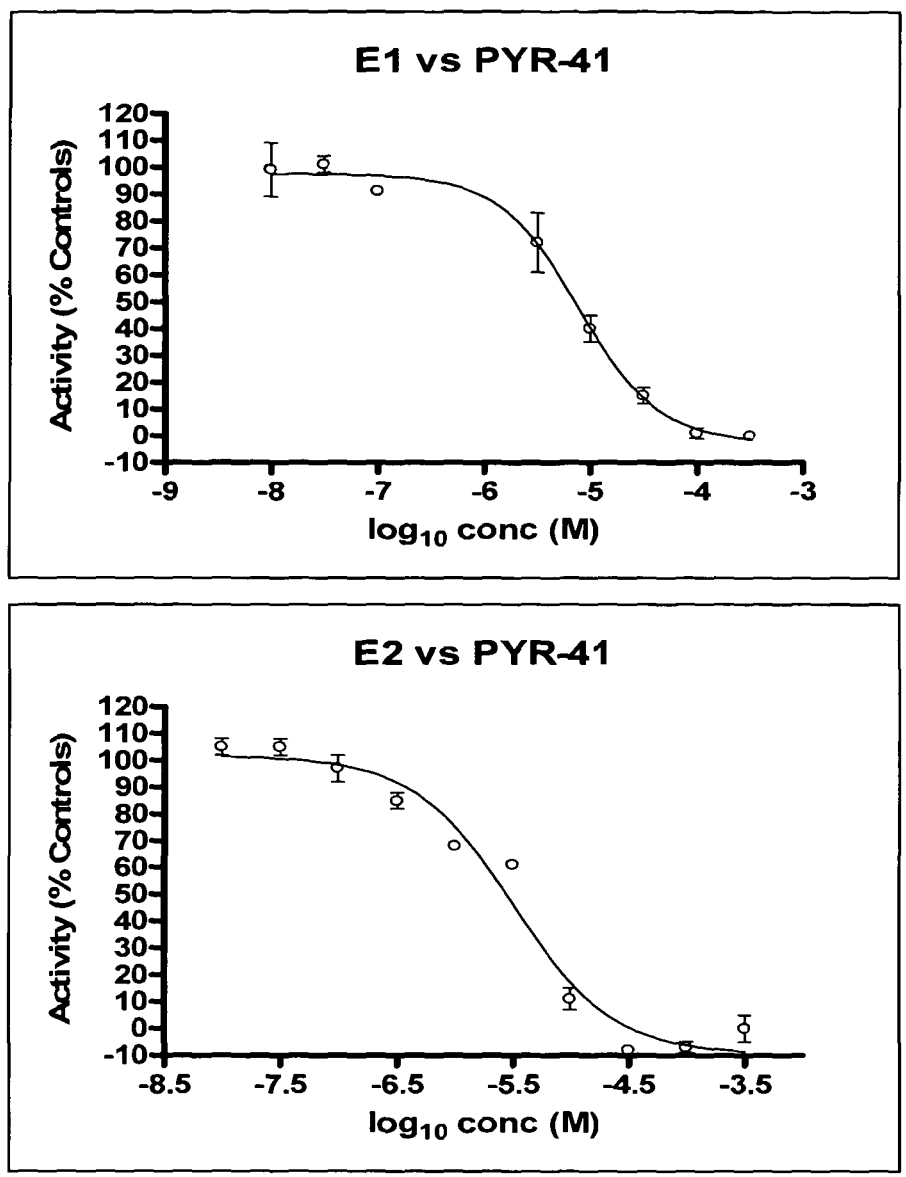

FIG. 30 (a): 'Live' SCF$^{Skp2/Cks1}$ Assay—ECL Inhibitor study—PYR-41 (E1 inhibitor). Used 60 minute incubation; 25 nM c-Myc p27 (phosphorylated in the absence of inhibitor); anti c-Myc capture for p27 (Millipore 05-274, 1/500); 5 nM E1; 1 μM E2 (HA); 25 nM E3 tetramer; 25 nM Cks1; 2 μM Ub; 100 μM ATP; streptavidin sulfo tag (MSD, R32AD-1, 1 μg/ml; titration of PYR41 (Calbiochem 662105) from 300 μM to 10 nM. IC$_{50}$ of 55 μM—significantly less potent than quoted IC$_{50}$ against the E1 assay only. BiogenNova quote IC$_{50}$ value as ~5 μM vs. E1.

FIG. 30 (b): E1/E2 Assay—ECL Inhibitor study—PYR-41. Used 60 minute incubation; 2 μM Ub; 100 μM ATP. For E1 assay (Anti-His capture) 50 nM E1. For E2 assay (Anti HA-capture) 5 nM E1; 50 nM E2. Used streptavidin sulfo tag (MSD R32AD-1, 1 μg/ml); titration of PYR41 (Calbiochem 662105) from 300 μM to 10 nM. IC$_{50}$ values of 7.8 and 3.2 μM for the E1 and E2 assays respectively. Significantly more potent than IC$_{50}$ against the E3 assay.

FIG. 31: 'Live' SCF$^{Skp2/Cks1}$ Assay—ECL R140 Kinase inhibitor panel (+PYR-41)

Figure 32:
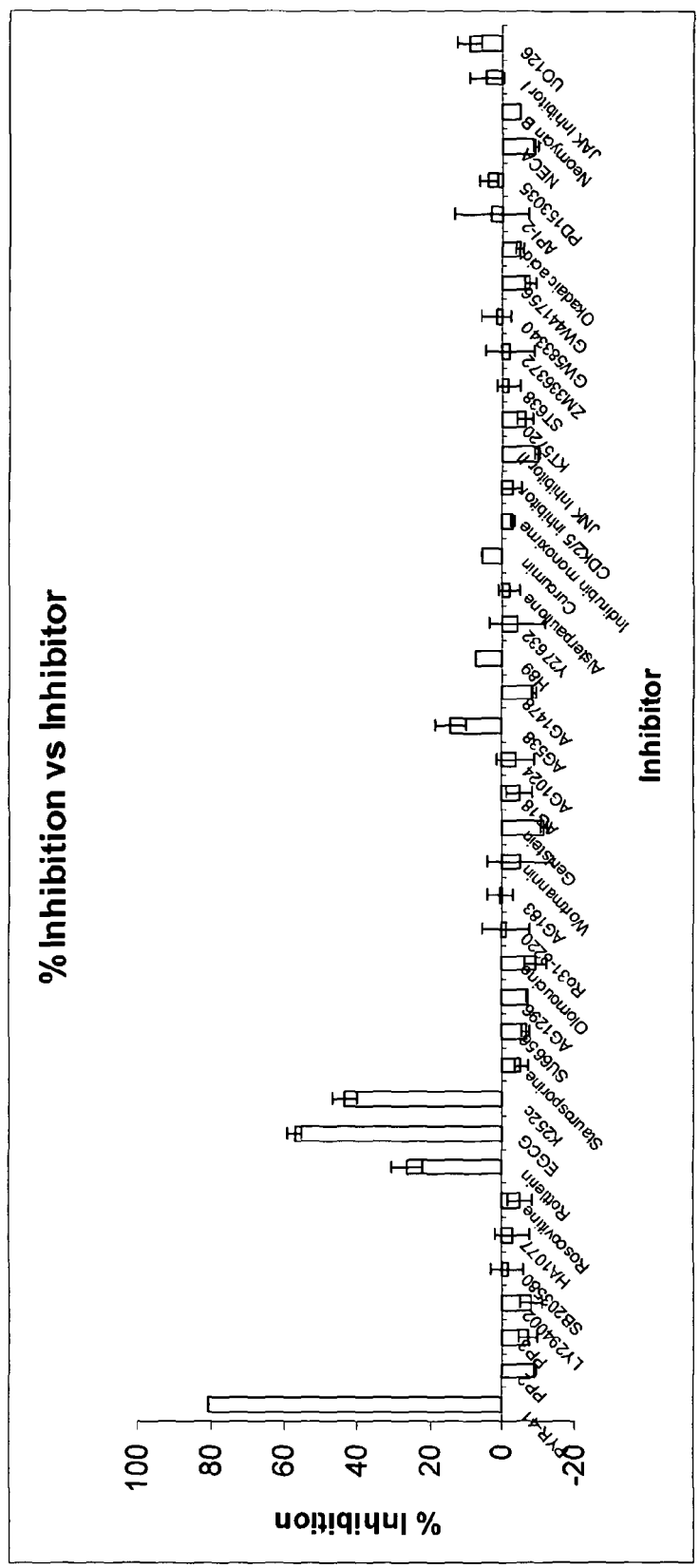

FIG. 32: 'Live' SCF$^{Skp2/Cks1}$ Assay—ECL R140 Kinase inhibit or panel. Used 60 minute incubation; 25 nM c-Myc p27; anti-c-Myc capture for p27 (Millipore 05-274, 1/500); 5 nM E1; 1 μM E2 (HA); 25 nM E3 tetramer; 25 nM Cks1; 2 μM Ub; 100 μM ATP; streptavidin sulfo tag (MSD, R32AD-1, 1 μg/ml). Several compounds show up as inhibitors—Rottlerin, EGCG, K252c and AG538.

Figure 33:
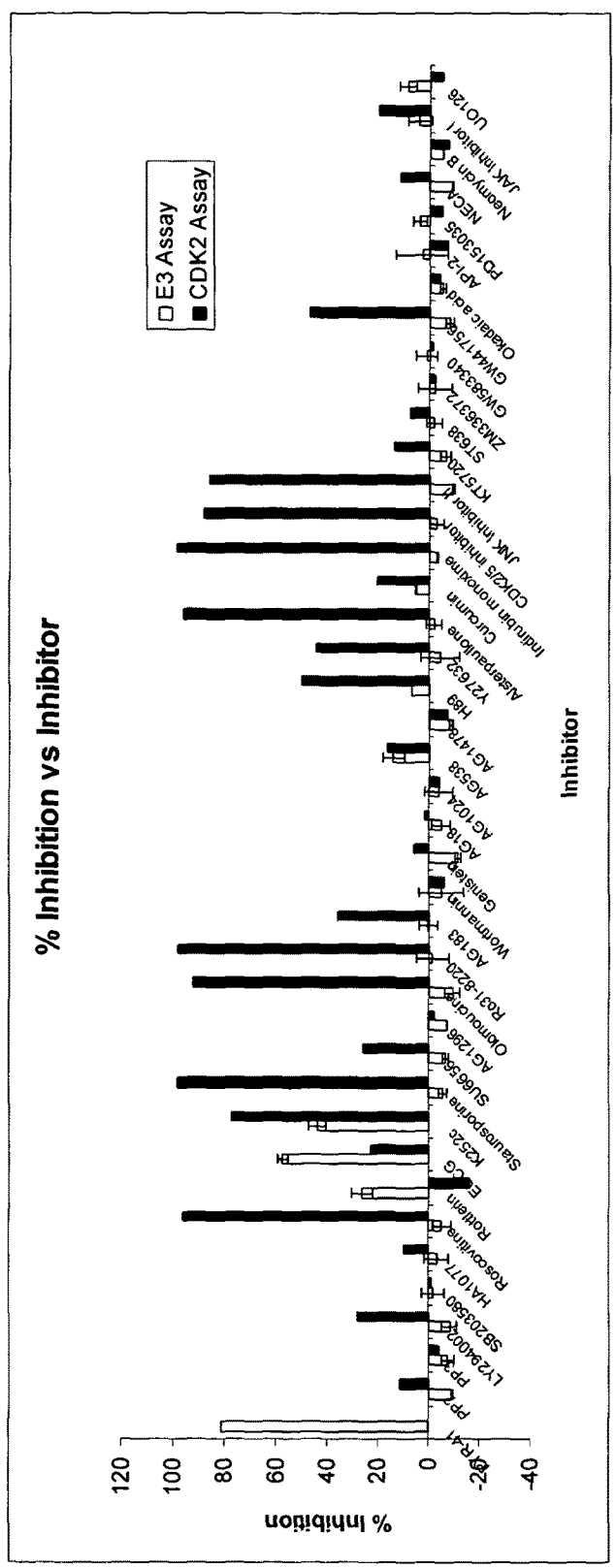

FIG. 33: 'Live' SCF$^{Skp2/Cks1}$ Assay—ECL R140 Kinase inhibitor panel. Comparison of the SCF$^{Skp2/Cks1}$ inhibition profile against the CDK2/CyclinE inhibition profile highlights very few similarities.

Figure 34:
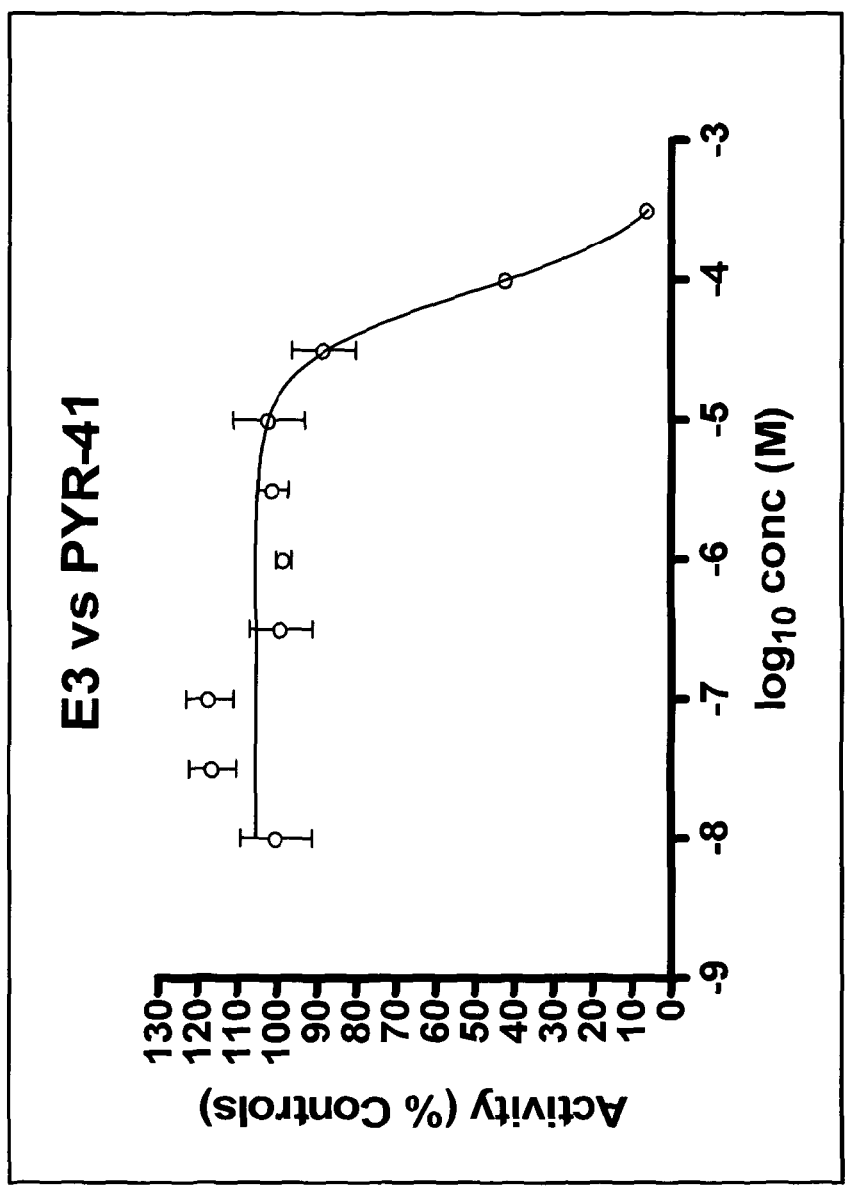
Figure 34:
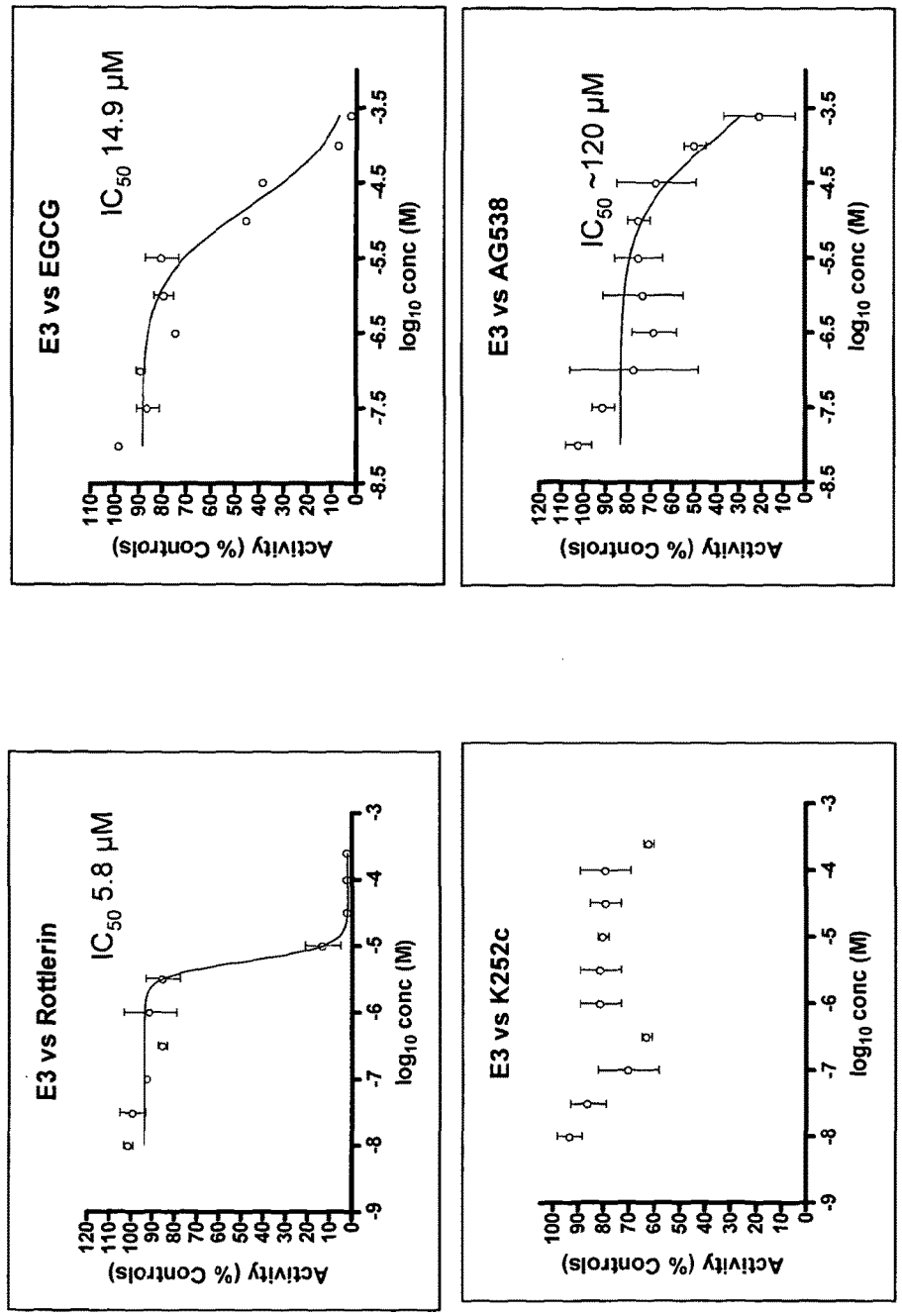

FIG. 34: 'Live' SCF$^{Skp2/Cks1}$ Assay—ECL follow up IC$_{50}$s. Used 60 minute incubation; 25 nM c-Myc p27; anti c-Myc capture for p27 (Millipore 05-274, 1/500); 5 nM E1; 1 μM E2 (HA); 25 nM E3 tetramer; 25 nM Cks1; 2 μM Ub; 100 μM ATP; streptavidin sulfo tag (MSD, R32AD-1, 1 μg/ml). Titration of PYR41 (Calbiochem 662105) from 300 μM to 10 nM (control). Titration of Rottlerin, EGCG, AG538 and K252c from 300 μM to 10 nM. PYR-41 IC$_{50}$ of 84 μM—Comparable to previous IC$_{50}$ data.

Figure 35:
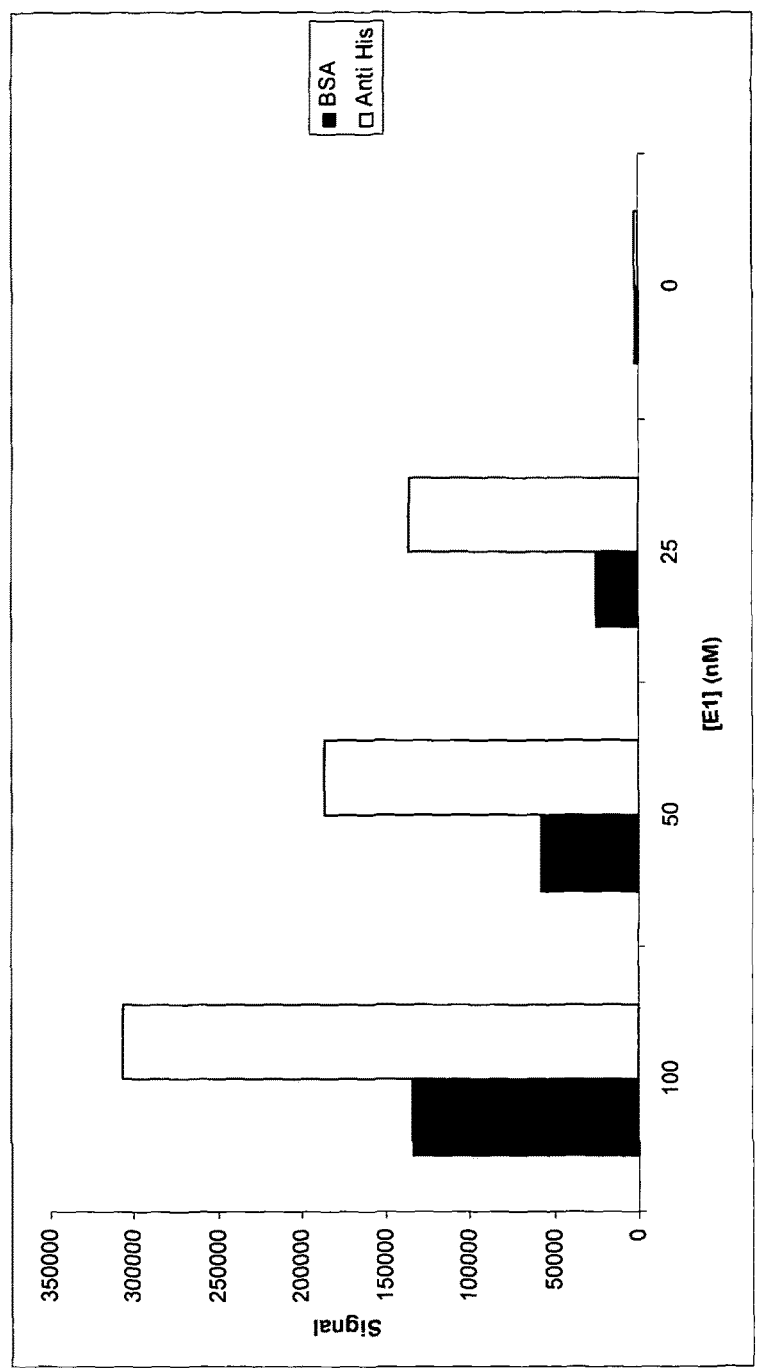

FIG. 35: E1, E2 and E3 assay non-specific binding. E1 assay—anti His capture for specific binding and BSA block only for NSB. Clearly some NSB, however the relative portion of NSB drops as the concentration of E1 is reduced. NSB signal in the E3 assay is unlikely to be particularly high due to the low concentration of E1 present (5 nM).

Figure 36:
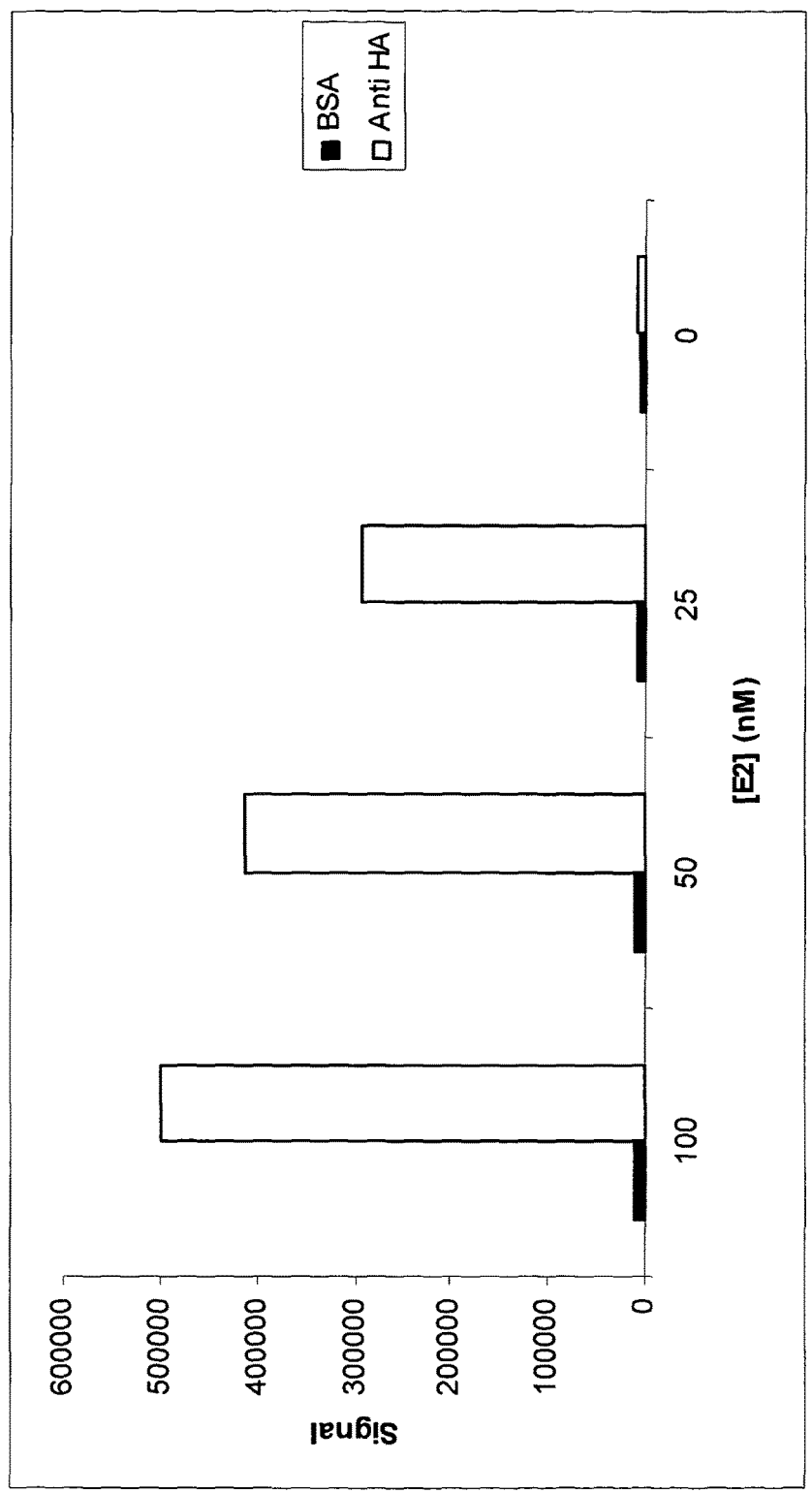

FIG. 36: E1, E2 and E3 assay non-specific binding. E2 assay—Anti HA capture for specific binding and BSA block only for NSB. No indication of non-specific binding in the E2 assay.

Figure 37:
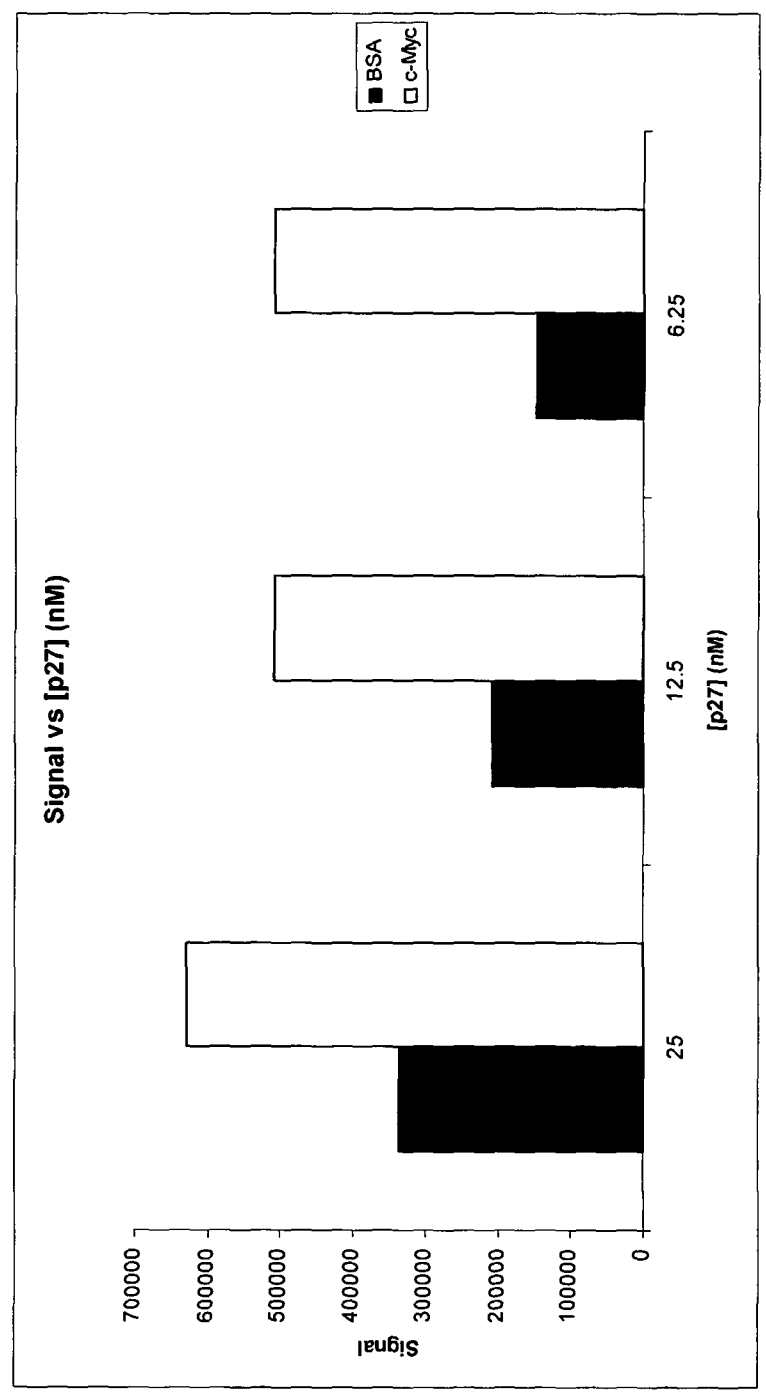

FIG. 37: E1, E2 and E3 assay non-specific binding. E3 assay—anti c-Myc capture for specific binding and BSA block only for NSB. Clearly some NSB, however the relative portion of NSB drops as the concentration of p27 is reduced. Although there is some non-specific binding, it is unlikely to be NSB from the desired captured species.

Figure 38:
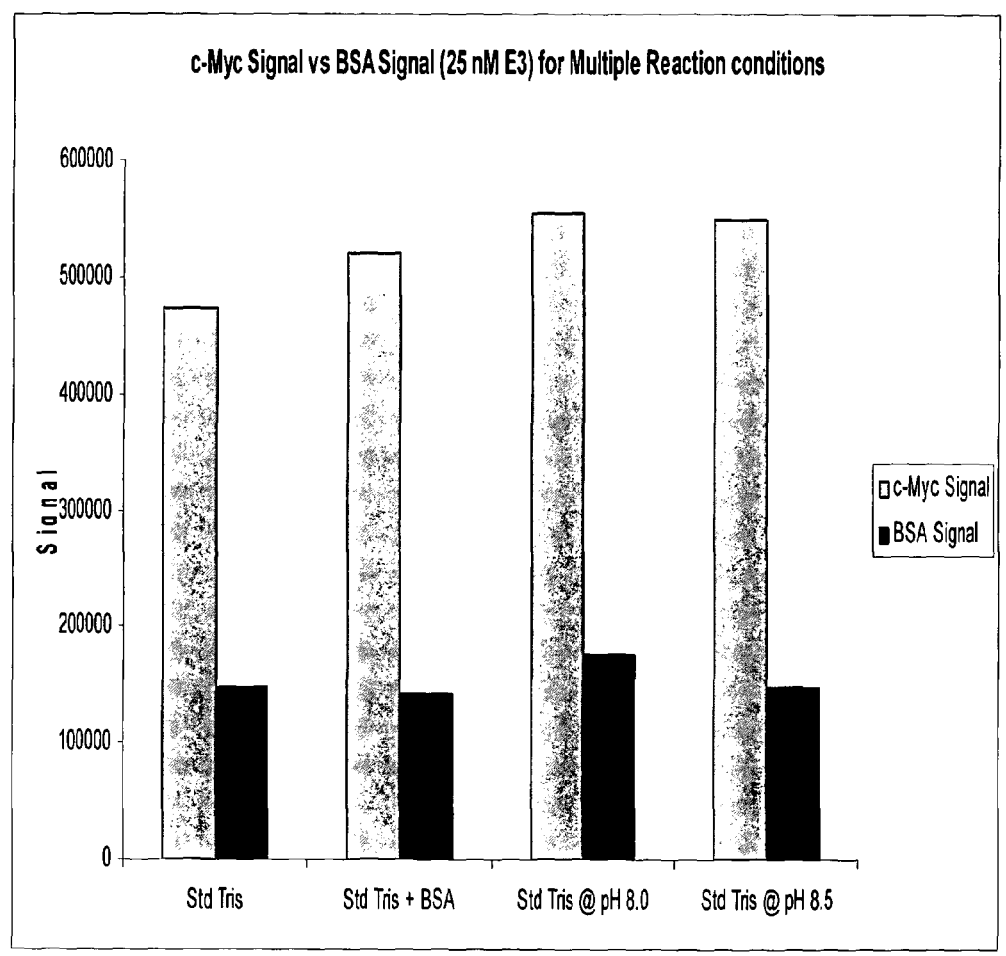

FIG. 38: E1, E2 and E3 assay non-specific binding. Multiple approaches were employed in order to minimise the E3 assay NSB signal including: Buffer pH; BSA; Salt; detergents; buffers; p27/E3 concentrations; blocking solutions. None were successful.

Figure 39:
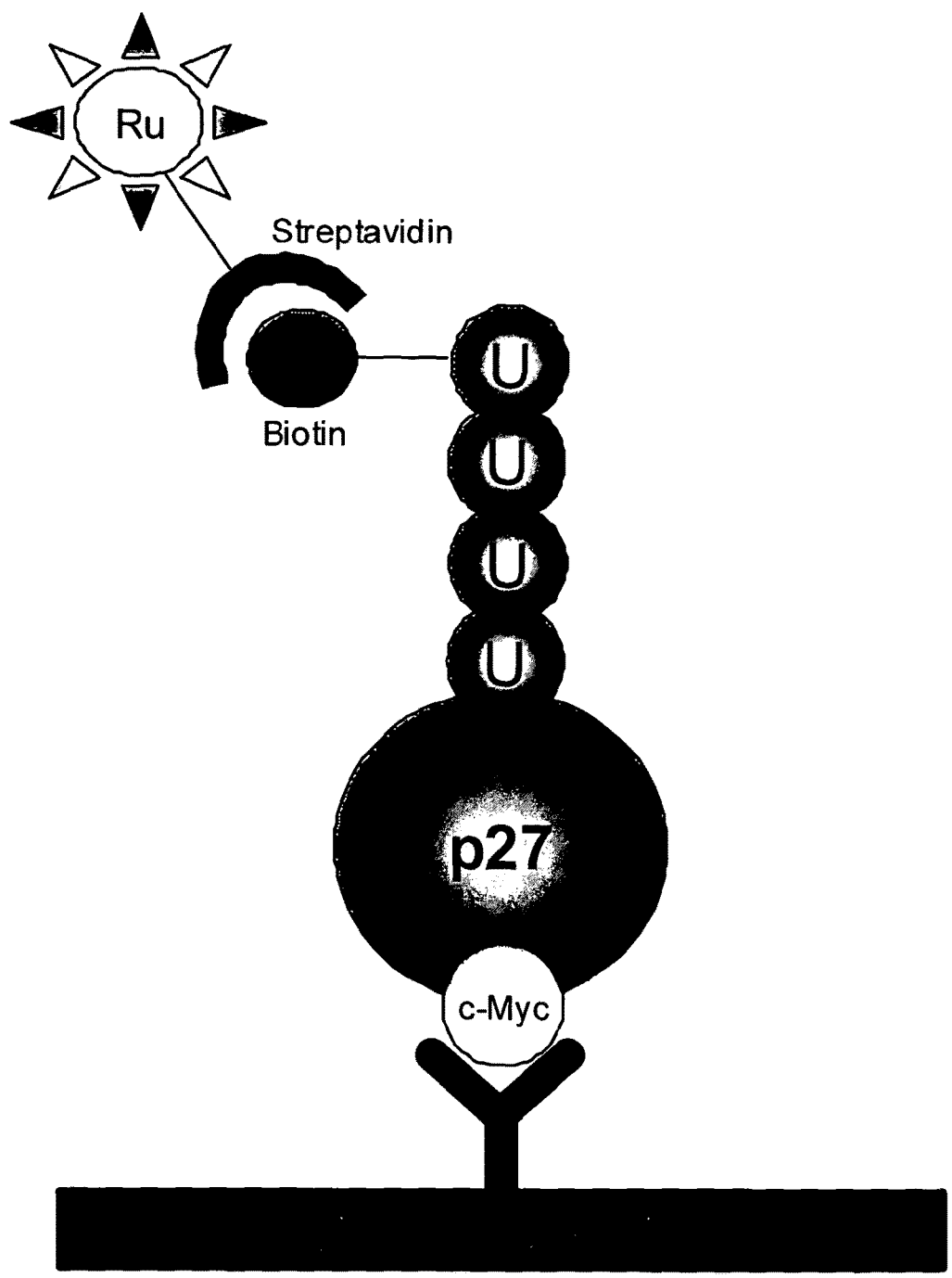

FIG. 39: Schematic showing a current being passed through an electrode, which in turn causes stimulation of the labelled binding partner, in turn causing a signal to be emitted.

MODES FOR CARRYING OUT THE INVENTION

Coding sequences used throughout this study were cloned and validated against appropriate GenBank entries (FIG. 1).

Molecular weights of purified proteins were confirmed by SDS PAGE followed by Western blot analysis.

Assay Development Pilot: Components Upstream of E3

Initial experiments in the pilot phase focussed on establishing that the components upstream of the E3 are active, and then optimising the levels of each component required so that we limit the variables for the E3 assay.

Figure 2:
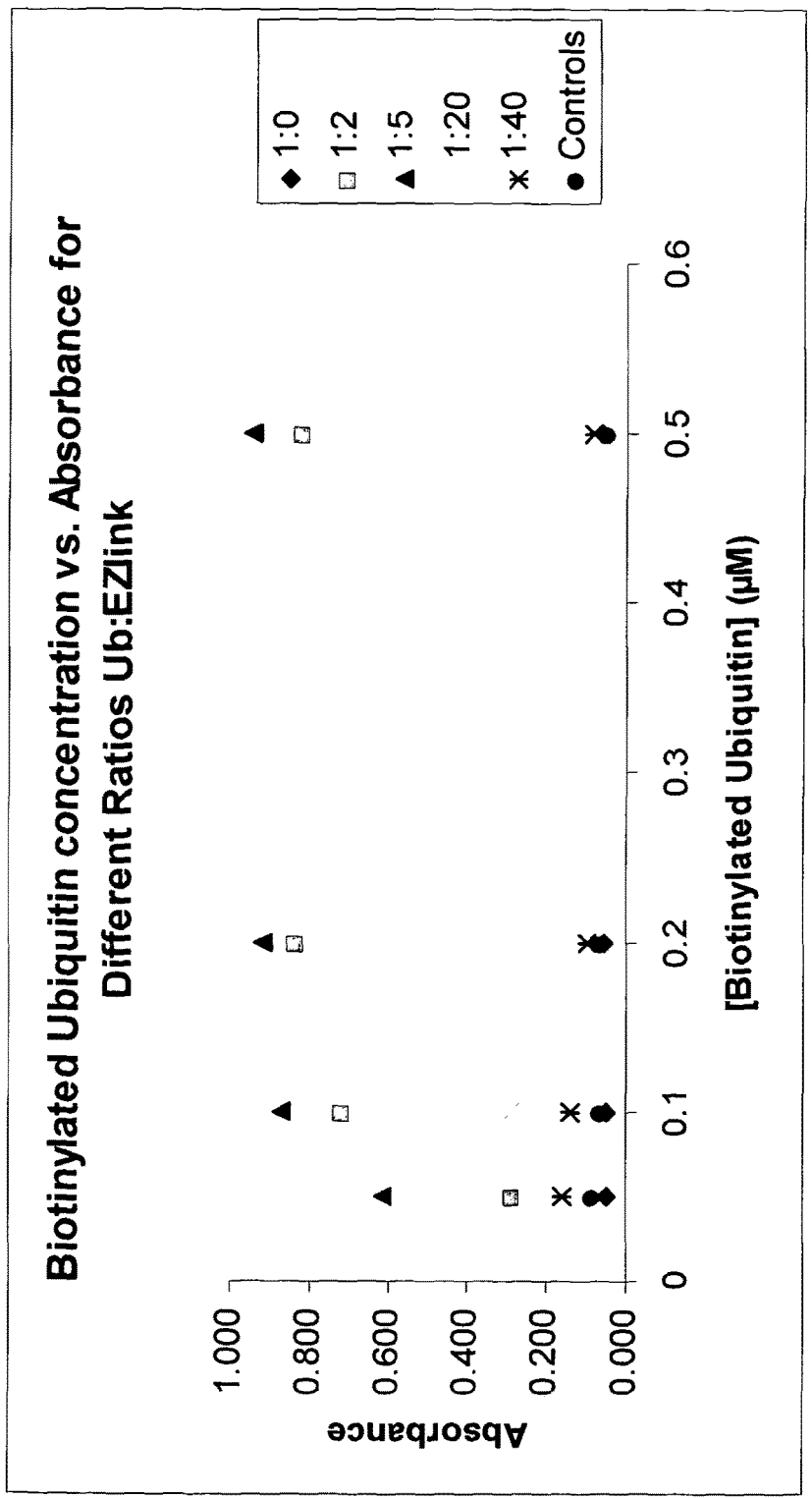
FIG. 2: Ubiquitin biotinylation. Success of biotinylation and optimal conditions determined by ELISA (Streptavidin plate, anti-Ub primary antibody (R+D Systems, MAB701, 0.1-2 μg/ml), anti species-HRP secondary (Sigma, A5278, 1 μg/ml)

The majority of assays require the use of biotinylated ubiquitin in order to recruit streptavidin linked reporter molecules. Biotinylation reactions were carried out and assessed by ELISA to determine optimal biotin:ubiquitin ratios (FIG. 2).

Results showed that using a labelling ratio of either 2:1 or 5:1 biotin:ubiquitin provided the best signal by ELISA. Higher ratios were detrimental, and lower ratios look to be inefficient.

Positive Controls of Ubiquitinated E1 and/or E2

Figure 3:
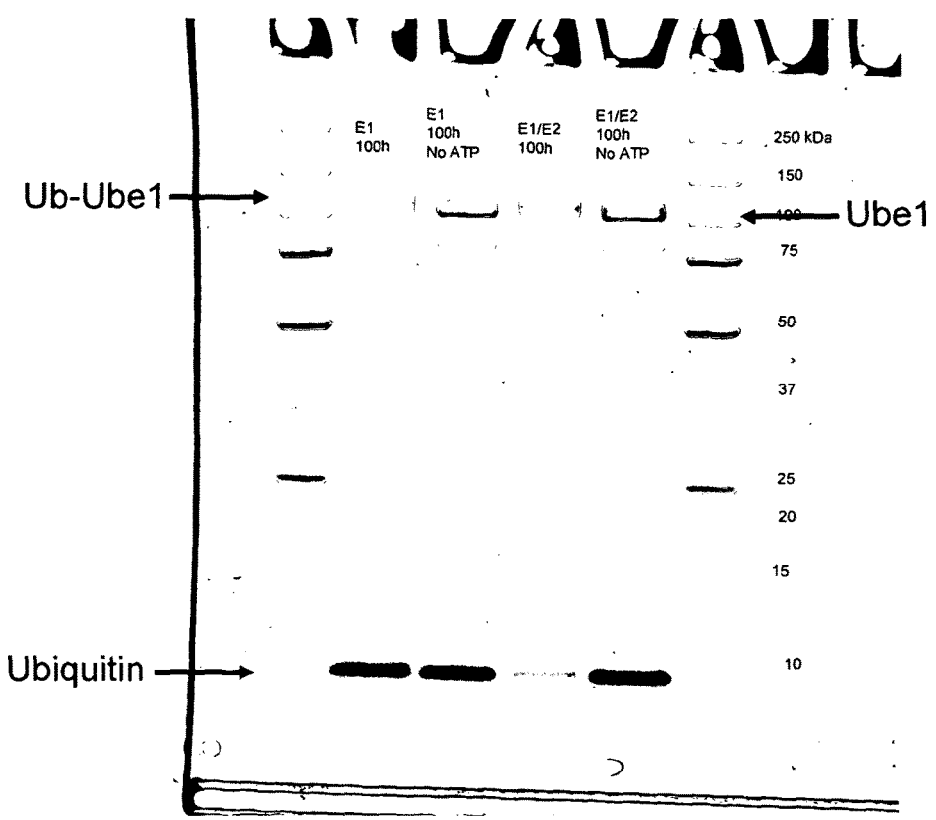
FIG. 3: Ube1 and Ube1/UbcH3-Gel based. Incubated E1/Ub/ATP and E1/E2/Ub/ATP (100 hr incubation) tested using SDS PAGE gels. A band shift indicative of the presence of Ubiquitinated Ube1 has been observed in both E1 and E1/E2 assays. No band associated with Ubiquitinated UbcH3 is visible. This band shift is ATP dependent. Antibody used: Mono- and poly-Ubiquitinated conjugates, mouse mAb horseradish peroxidise conjugate (FK2H) Enzo Life Sciences, Cat no. PW0150, Batch no. X08036, supplied at 1 mg/ml, used at 1/1000 dilution.

Prolonged incubation of Ube1 (E1), UbcH3 (E2) and ubiquitin at ratios of 1:1:20 micromolar were set up to generate a positive control of ubiquitinated E1 and/or E2 which could then be used in establishing detection conditions for the HTRF and ECL platforms. Initial SDS polyacrylamide gel-based examination of ubiquitinated Eland E1/E2 showed that there was a ubiquitination event occurring, with an apparent shift in the molecular weight of E1 (FIG. 3). A decrease in the intensity of the ubiquitin band could also be seen in some samples. The assays were set up with stoichiometric amounts of E1 and E2 and a 20-fold excess of biotinylated ubiquitin. The band shifts were shown to be ATP dependent.

The gels were also probed with an antibody against ubiquitinated species. The antibody does not recognise free ubiquitin. The Western blots for this experiment showed a clear band representing ubiquitinated E1. It was noted at this stage that the intensity of the band for E1 was markedly increased when E2 was present.

Western blot analysis (Anti-mono and polyubiquitinated protein-HRP conjugate) revealed a positive response for Ube1 only in the presence of ATP. This indicates ubiquitination of Ube1. No positive response for UbcH3 was observed in the absence of Ube1. When Ube1 and UbcH3 were added together, we detected a positive response Ube1, which was time dependent.

Developing the Detection Methodology—HTRF

Samples were pre-incubated with equimolar amounts of the E1 and E2, and bio-ubiquitin and a dilution step was adopted to reduce the amount of E1 in the detect step to 10 nM. This resulted in encouraging ratios, indicating that the format was detecting the presence of ubiquitinated E1 and E2

Figure 4:
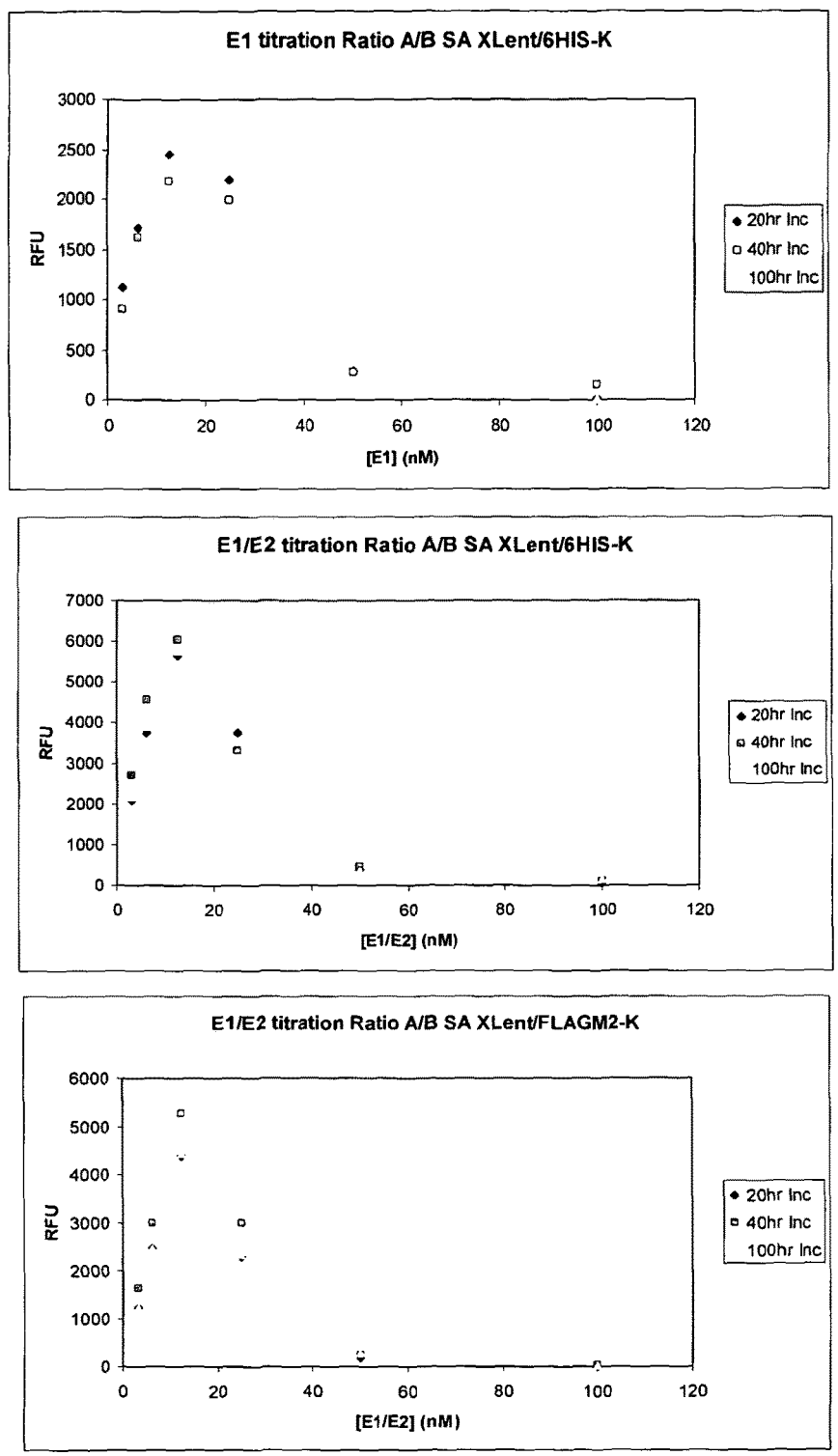
FIG. 4: Pre-incubated Ube1/UbcH3 HTRF. Pre-incubated E1/Ub/ATP and E1/E2/Ub/ATP (20, 40 and 100 hour incubation) tested using HTRF platform. Anti-6His-K was employed for E1 and E2 detection; Anti-FLAG-K for E2; Biotinylated Ub; and Streptavidin XLent! for biotin. FRET signal indicative of the presence of Ubiquitinated Ube1 and UbcH3 has been observed. This signal is enzyme and ATP dependent for the E1/E2 assays, as well as time dependent for the E1 assay.

FIG. 4 shows the bell-shaped curve typical of a titration in this format of assay.

The initial experiments were all carried out using prolonged incubation times to try to ensure that the reaction had progressed as far as it was likely to go in order to try to maximise the population of ubiquitinated E1 or E2 (FIG. 4).

Figure 5:
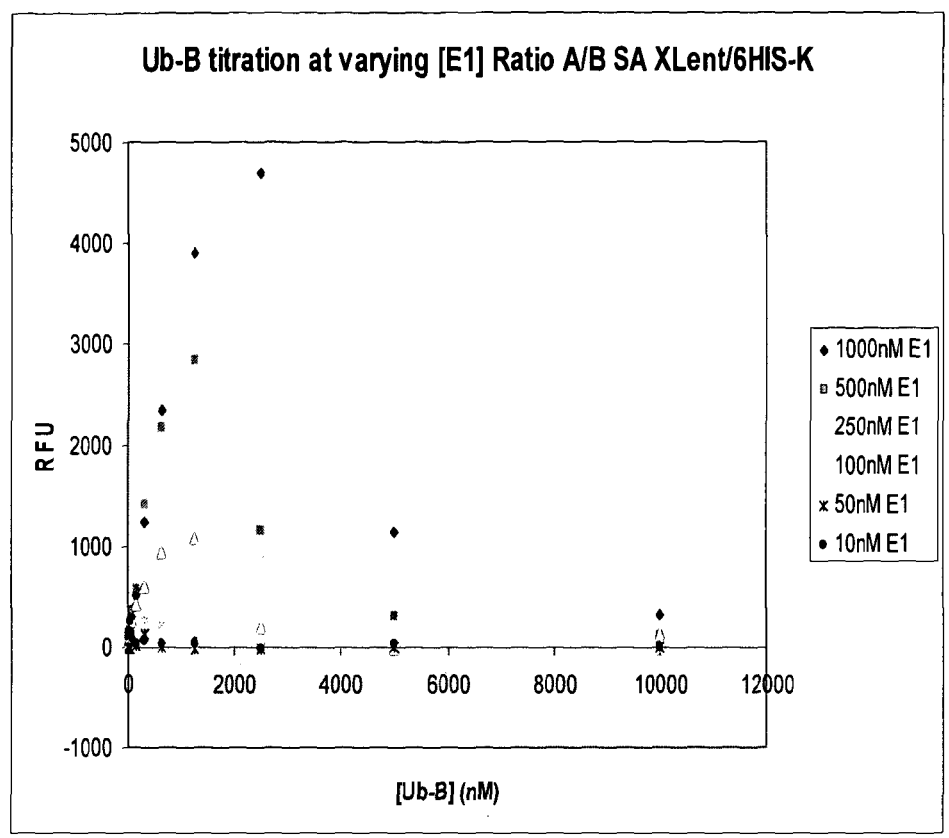
FIG. 5: 'Live' Ube1 assay (60 minutes incubation)—HTRF. 'Live' assays (60 minute incubation) for Ube1 at higher concentrations (>250 nM) show a good signal which is dependent on the Ub-biotin concentration. Anti-6His-K was employed for E1 detection; biotinylated Ub; and Streptavidin XLent! for Biotin. At lower E1 concentrations, the excess of Ub-biotin inhibits the detection of a signal.

Subsequent assays brought the incubation times to a more realistic period. The 60 minute live assay (i.e. not pre-incubating) using a 2-way checkerboard for E1 and bio-ubiquitin showed that the HTRF ratio will form in this time-frame. Samples were again diluted to 10 nM E1 detection concentrations (FIG. 5).

The amount of bio-ubiquitin excess over the E1 concentration is critical, else the signal gets lost in the background.

All HTRF specific reagents were from Cisbio, including: Streptavidin-Xlent (611 SAXLB), Anti-6His-K (61 HISKLA), Anti-FLAG-K (61FG2KLA), and were used at concentrations specified by the manufacturer.

Developing the Methodology—ECL

Figure 6:
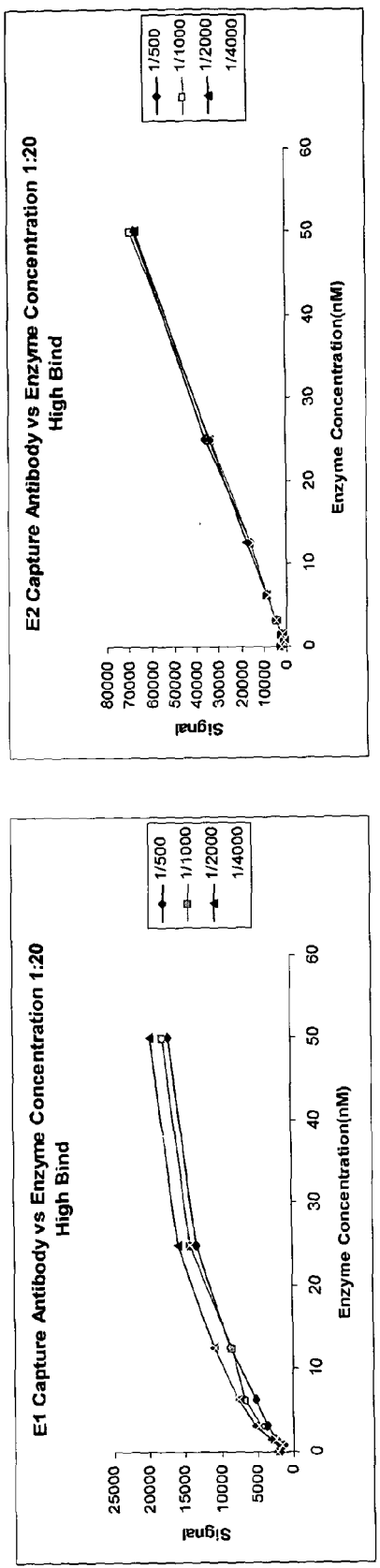
FIG. 6: Pre-incubated Ube1/UbcH3-ECL. Pre-incubated E1/Ub/ATP and E1/E2/Ub/ATP (100 hour incubation) tested using ECL platform. Used Anti-His capture for E1 (Millipore, 16-255, 1/500-1/4000 dil); anti-FLAG capture for E2 (Millipore, MAB3118, 1/500-1/4000); biotinylated Ub; and streptavidin sulfo tag (MSD, R32AD-1, 1 μg/ml). Signal of the presence of ubiquitinated Ube1 and HbcH3 has been observed.
Figure 7:
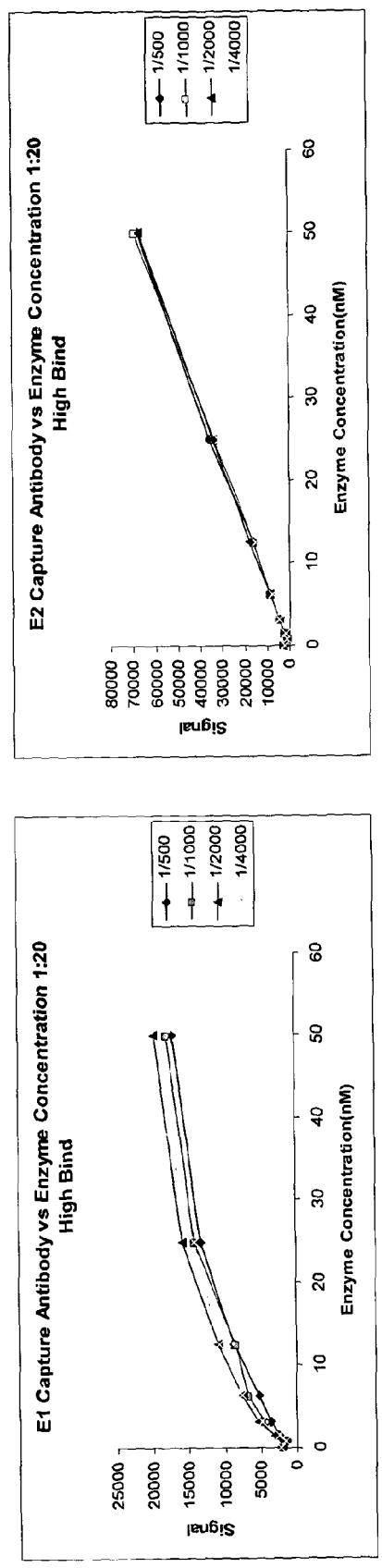
FIG. 7: Live Ube1 assay (60 minutes inc.)—ECL. Initial 'live' assays (60 minute incubation) for Ube1 show good signal (>1000000) but very high background level (>250000) (Max signal/background 4-5 fold). Subsequent Ubiquitin only controls indicates that at elevated concentrations of ubiquitin, there is non-specific ubiquitin binding and consequently high background.

Unlike the HTRF format, the ECL assay is a wash format assay. The initial experiments using the pre-incubated material of 1:1:20 E1:E2:Bio-Ub at 2 mM ATP showed a signal response dependent on the amount of E1 or E2 present. The experiment enabled the selection of the type of plate (high bind vs low bind) and the selection of capture antibody concentrations for subsequent experiments (FIG. 6). It also indicated that the E2 was becoming ubiquitinated (FIG. 7).

Figure 8:
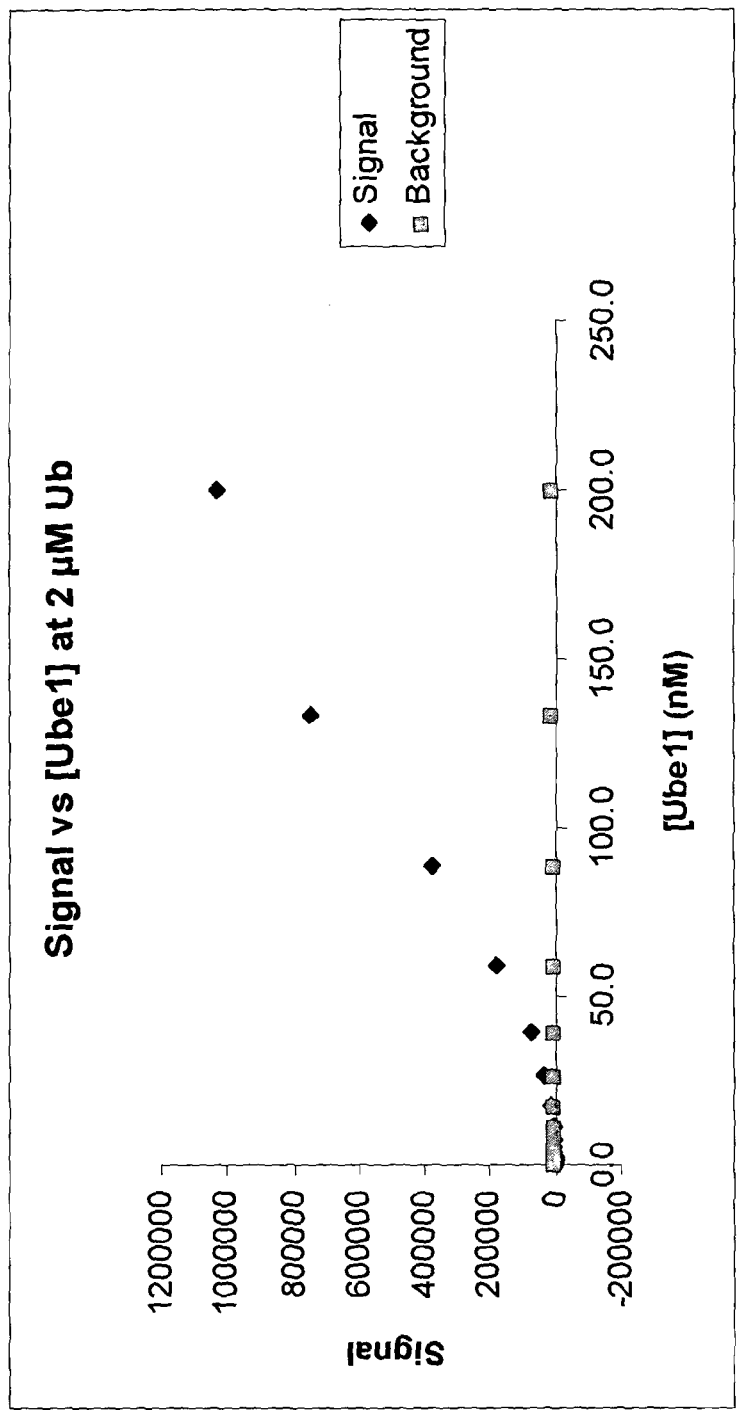
FIG. 8: Live Ube1 assay (60 minutes inc.)—ECL. 'Live' assays (60 minute incubation) for Ube1 at lower concentrations of Ub (2 μM) still show good signal (>1000000) and lower background (<10000) (Max signal/background ~100 fold). Observed 'lag' in signal increase with increasing Ube1 concentration. Signal is low at low concentrations of Ube1 (<25 mM). Approximately linear increase in signal after 25 nM.

While the assay format is wash based, it has been shown that the concentration of bio-ubiquitin that can be used is not limitless, and will contribute to a significant background. Reducing the amount of bio-ubiquitin in the assay restores the S/B accordingly. An E1 titration gives a good response, and there are hints of sigmoidal behaviour (FIG. 8).

The next steps for this format are the bio-ubiquitin and ATP titrations to establish the concentrations that will be considered non-rate limiting in downstream ubiquitination assays. The E2 also needs to be titrated into the system. There are 3 E2 molecules available, and the best performing one will be selected for the final stage of the pilot study.

Continued Optimisation Using the ECL Assay

Figure 9:
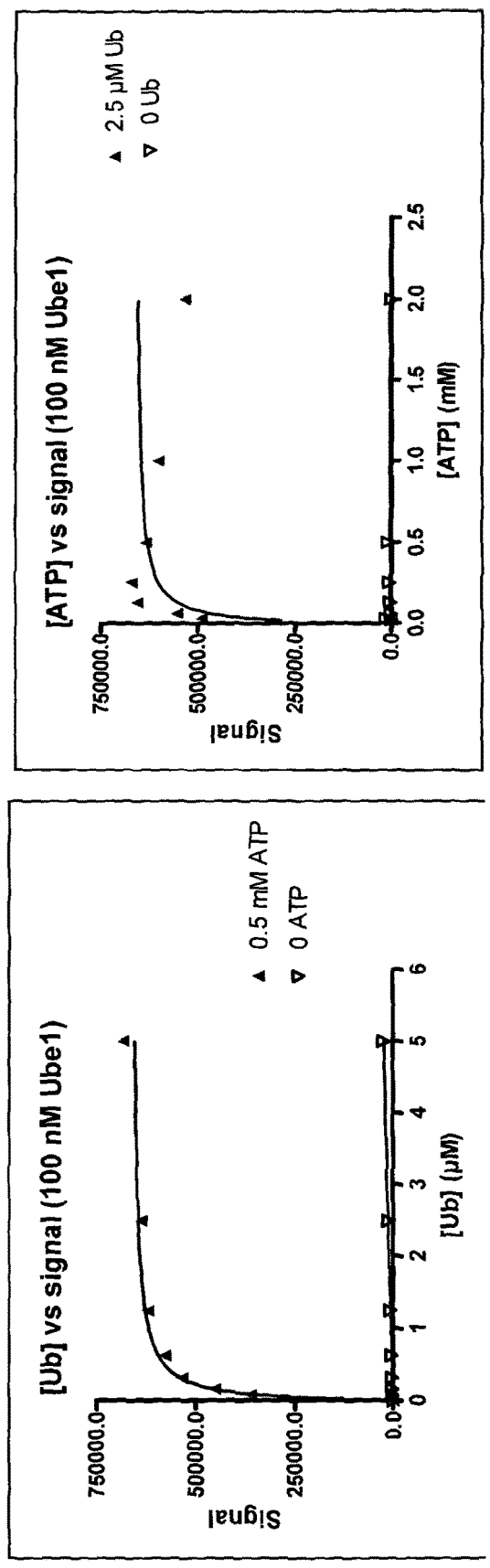
FIG. 9: ATP and Ubiquitin titration (Ube1 Assay)—ECL. 'Live' Ube1 assay E1/Ub/ATP, varying ATP and Ubiquitin concentrations. Uses Anti-His capture for E1 (Millipore, 16-255, 1/1000 dil); 100 nM Ube1; biotinylated Ub; streptavidin Sulfo tag (MSD, R32AD-1, 1 μg/ml). Saturating ubiquitin and ATP conditions—2 μM Ub/500 μM ATP.

Continuing with the E1 protein optimisation, ATP and ubiquitin titrations were performed to identify the conditions which are saturating, or non-rate limiting, for the E1 section of the cascade (FIG. 9).

The results suggest that after 2 micromolar Ubiquitin and at 500 micromolar ATP, there is no additional signal generation. These concentrations have therefore been taken as the saturating conditions for the E1 protein.

Figure 10:
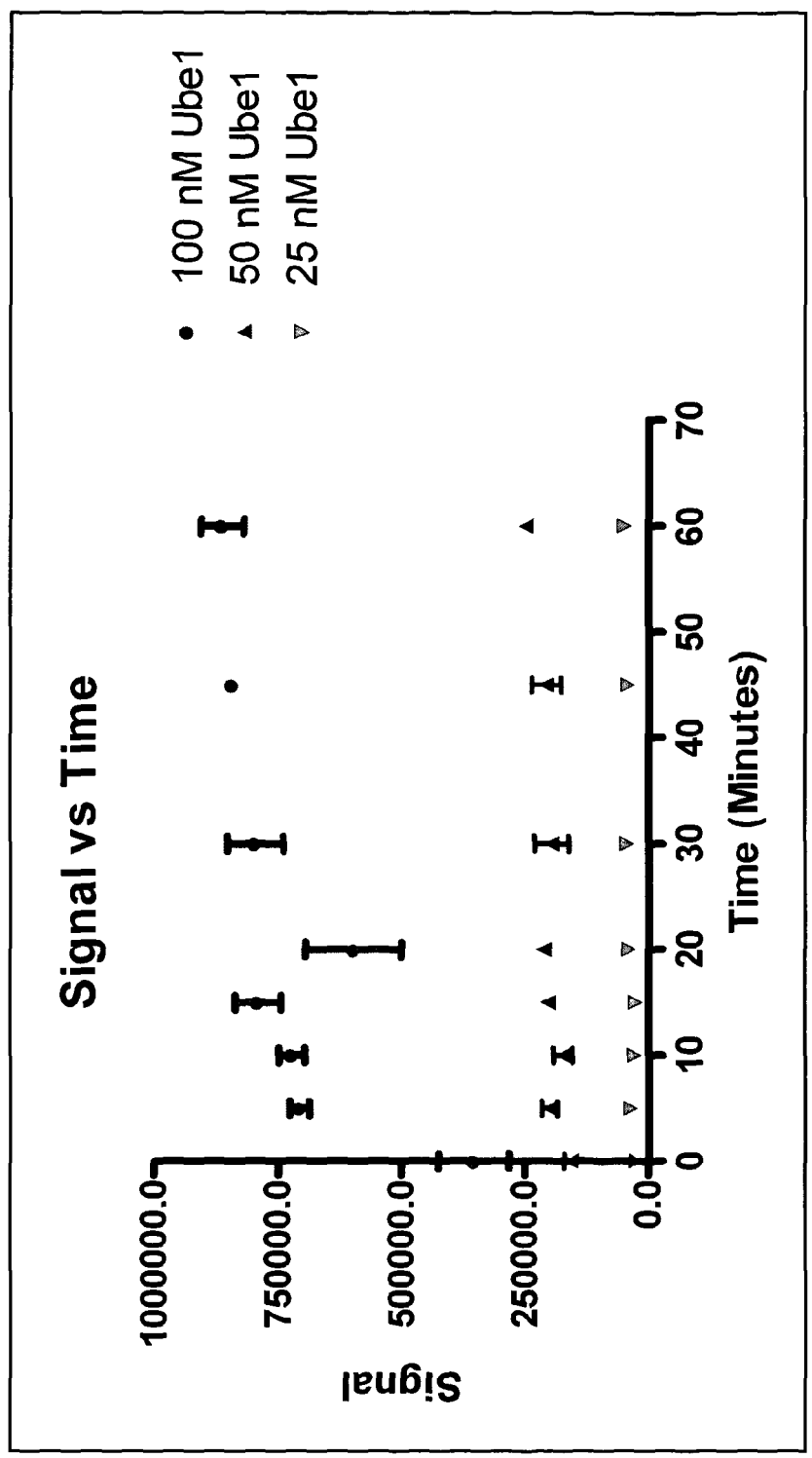
FIG. 10: Ube1 timecourse—ECL. E1 assay appears to reach completion after a very short time period. Impossible to monitor in current format. Could reduce the amounts of ATP/Ub or decrease reaction temperature to see reaction progress.

Following the identification of the ATP and ubiquitin concentrations to use, a time-course of signal generation was followed, to determine a linear part of the reaction velocity curve to use for subsequent inhibitor experiments (FIG. 10).

What was found was that the reaction appears to happen very quickly, in fact within the dead time of setting up the assay. The fast nature will be an advantage in downstream events with the E2 and E3 assays.

For the $IC_{50}$ determination of Pyr-41, the data shown is that from a 30 minute pre-incubation and a 30 minute assay. The assay was performed in a separate plate and then transferred. For information purposes, another set of assays were performed within the capture/detect plate and stopped immediately by washing off the assay solution, or washed after 60 min. It was interesting to note that even with the wash at time 0 an $IC_{50}$ for the compound that was in line with the data shown could still be determined.

Figure 11:
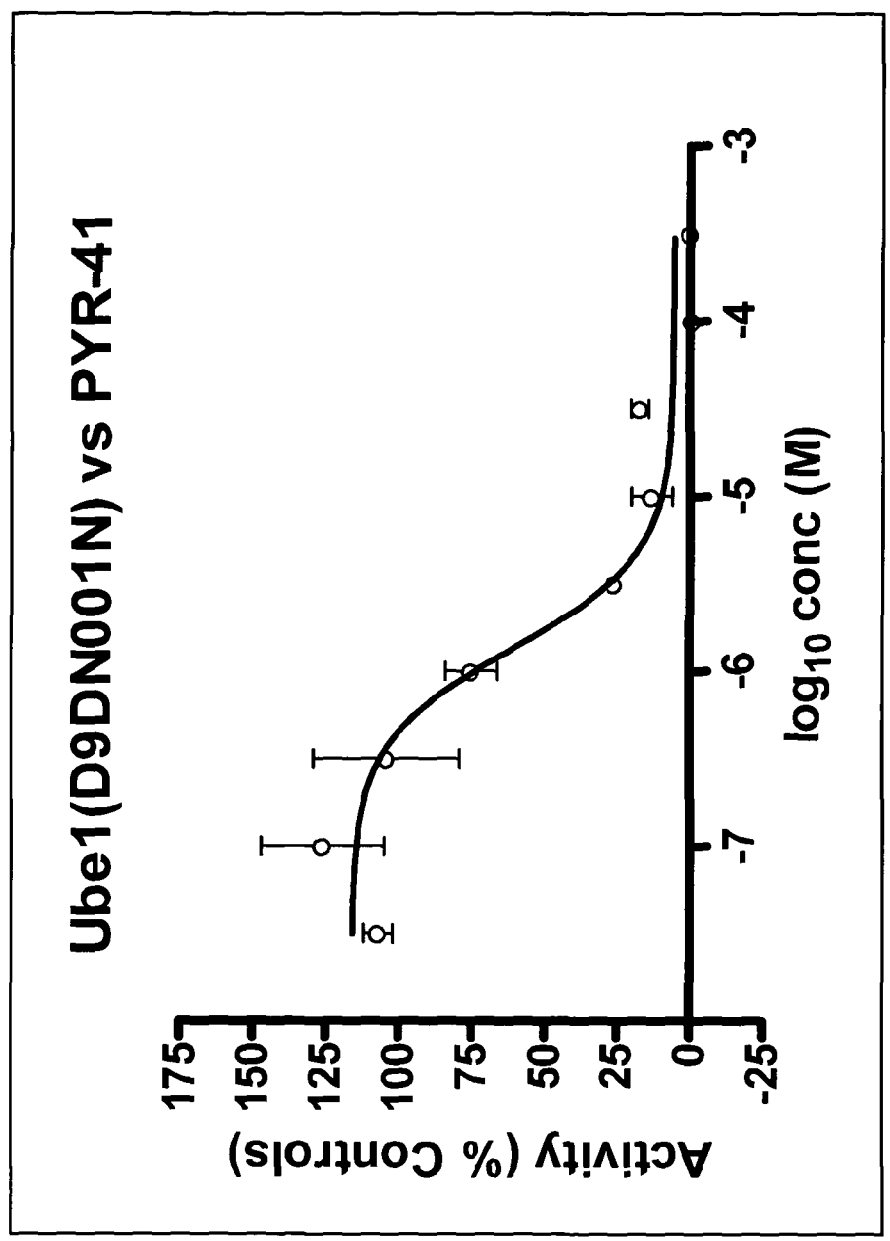
FIG. 11: Ube1 inhibitor study PYR41—ECL. Inhibitor study. Titration of PYR41 (Calbiochem 662105) from 30004 to 10 nM. Used anti-His capture for E1 (Millipore, 16-255, 1/1000 dil); 50 nM E1; 2 μM Ub; 500 μM ATP; 30-minute pre-incubation with cpd.; 30 minute reaction time. $IC_{50}$ of 1.3 μM—Similar to literature $IC_{50}$ value: BiogenNova quote $IC_{50}$ value as ~5 μM.

Reported values for the inhibitor are in the low micromolar range (FIG. 11).

The detection of ubiquitinated E2 was explored, initially using material that had been pre-incubated for 24 hrs. Equimolar E1, E2 and ubiquitin were used for this preliminary experiment, and the concentration of capture antibody determined. The results below are representative, and all 3 E2 constructs were tested.

Figure 12:
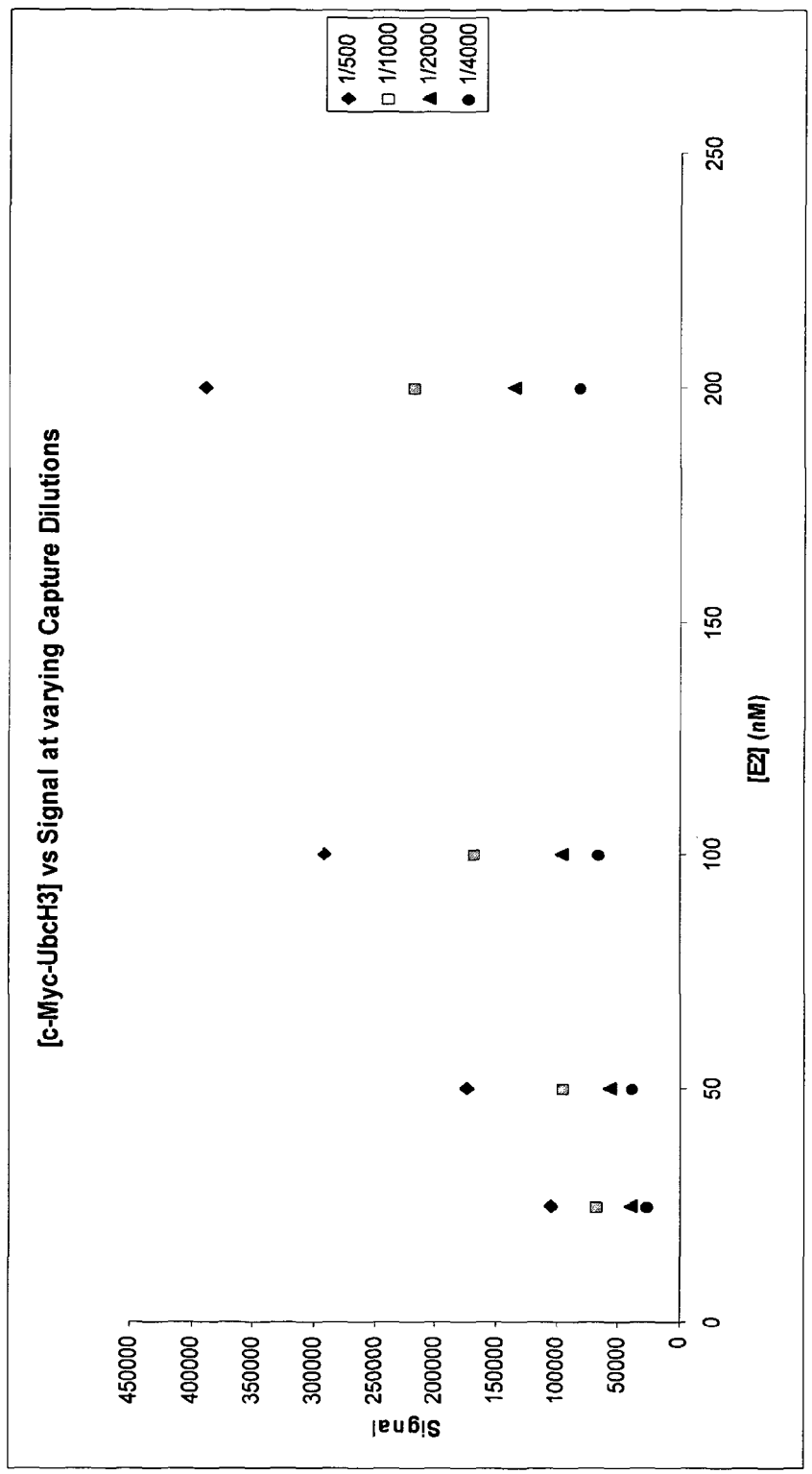
FIG. 12 (a): Pre-incubated UbH3-ECL. Used pre-incubated His-E1/FLAG, c-Myc, HA-E2/Ub/ATP (24 hour incubation) and was tested using ECL platform. Used Anti-FLAG, c-Myc and HA capture for E2 (Millipore, MAB3118 (FLAG), 05274 (c-Myc), 05-904 (HA), all 1/500-1/4000); biotinylated Ub (1 μM); ATP 500 μM; E1:E2 pre inc. 1 μM:1 μM; streptavidin sulfo tag (MSD, R32AD-1, 1 μg/ml). Signal indicative of the presence of Ubiquitinated UbcH3 has been observed.
Figure 12:
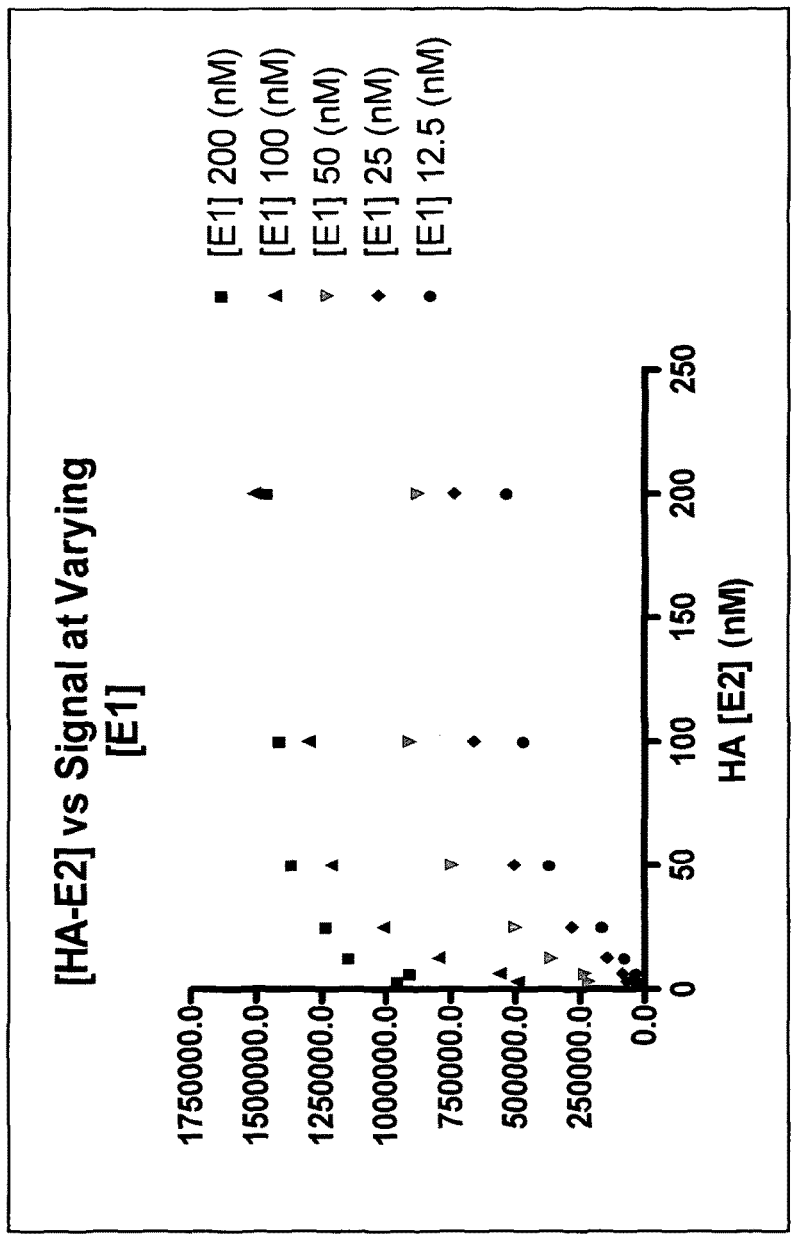

This experiment was followed up with an E1 vs E2 checkerboard using 2 micromolar ubiquitin and 500 micromolar ATP, concentrations determined to be optimal for the E1 ubiquitination previously. The assay was this time set up in a live format rather than use material from a prolonged incubation (FIG. 12).

Figure 13:
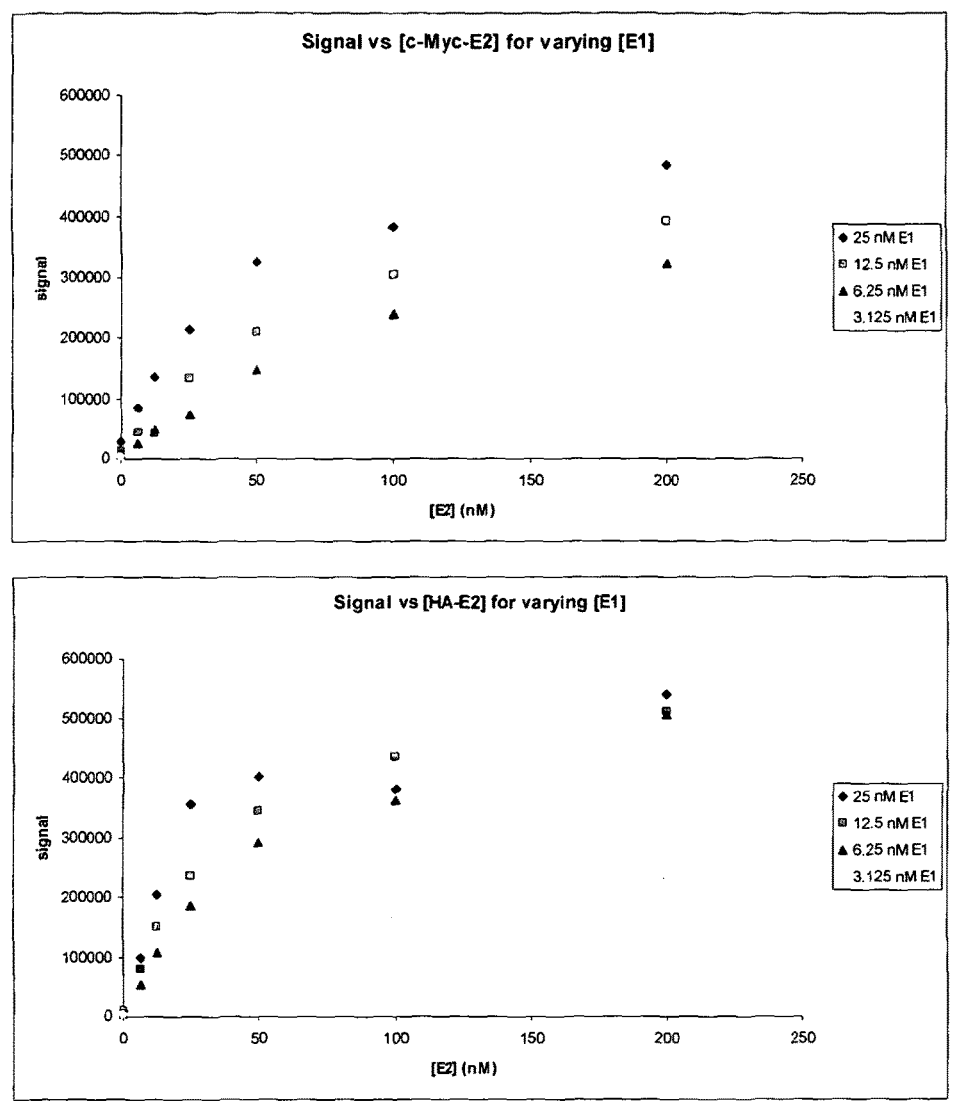
FIG. 13: 'Live' UbcH3 Assay—ECL. Used Anti-HA or Anti-c-Myc capture for E2 (Millipore, 05-904(HA), 1/500) (Millipore, 05-274 (c-Myc), 1/500); 3.125 to 25 nM E1; 6.25 to 200 mM E2; 2 μM Ub; 500 μM ATP; streptavidin sulfo tag (MSD, R32AD-1, 1 μg/ml). Some indication that non-specific binding of Ube1 leads to high signal. 'Live' UbcH3 assay repeated using low concentrations of Ube1.

Lower concentrations of E1 were tried in an attempt to bring down any background (FIG. 13). The lower range of E1 seemed to retain a decent E2 specific signal and also reduced non-specifics.

The assay for the E3 ubiquitination of p27 was trialled, initially using conditions described in the Xu paper (Xu et al, 2007, JBC, 282 15462-470), and then using conditions identified in-house. The former also included a capture antibody titration for the FLAG-tagged p27 (FIG. 14).

Both experiments demonstrate a signal for the ubiquitinated p27. The latter also indicates that the higher concentrations of p27 may be detrimental.

Continued Optimisation Using the HTRF Format

The progress with the E1 assay was continued by optimising the conditions for generation of signal.

A time course for the assay was examined initially using equimolar concentrations of the E1, E2 and ubiquitin.

Similar to the ECL format, the time-course in the HTRF assay indicates a very fast reaction (FIG. 15).

E2 was titrated against fixed concentrations of Ub and E1. The detection of ubiquitination was configured in two ways, using Anti-6His-K and Anti-FLAG-K. The former should detect the combination of ubiquitinated E1 and E2 as both carry a 6His tag, while the latter will detect the E2 ubiquitination only.

From the titration of E1 vs E2, concentrations of E1 and E2 were chosen for the ubiquitin titration, again detected with two configurations to arrive at conditions shown below for E1, E2, and Ub (100 nM E1, 1000 nM E2, 400 nM Ub) (FIG. 16).

The samples require dilution to a lower concentration than used in the assay, and by using the dilution methodology, workable ratios have been obtained. The diluent itself has also proven to be important, as diluting in the Stop solution, which contains EDTA (120 mM), does reduce the signal window compared to stopping the assay and then diluting in reaction buffer.

The various constructs of E2 and the two different E1 purifications were tested under the conditions derived above to see if some of the variables could be reduced.

The bar chart on the next slide shows the different ratios observed for the E1/E2 and the specific E2 signals. A common dilution for detecting for both the E1 and E2 was identified (1/10 which gives 10 nM E1 in the detection), and it is this shown in FIG. 17.

Using conditions identified previously, an $IC_{50}$ determination for Pyr-41 using the E1 and E1/E2 assays was performed. The results show a marked difference in inhibitor potency compared to literature values and that determined in the ECL format. This may be a reflection of the higher enzyme concentrations used in the HTRF assay step (FIG. 18).

Continued Optimisation Using Western Blots

As well as the ECL and HTRF assay formats, material has been examined by using SDS-PAGE and Western blotting to verify the presence (or absence) of ubiquitinated or phosphorylated material (FIG. 19).

The blots above show results from probing the membranes with an anti-phospho-p27 antibody. There is a clear indication that the p27 band has shifted, which could be interpreted as ubiquitination. The different loadings are 10, 20, 30 & 40 microliters of sample from right to left. It should be noted that there was not sufficient sample for the 40 microliter loading (estimated at 20 μL), so the signal is reduced from what would be expected.

On the right hand panel, a smear also appears in the No E1 lane. While this could mean that the E1 is not obligate, we have not seen this effect in either of the other assay formats, and so could also be a small contamination during the setup of this assay. Distinct banding can be seen in the lane with all components at 2 micromolar ubiquitin.

FIG. 20 also shows anti-phospho-p27, this time from experiments designed to identify conditions to ensure a good level of phosphorylation which is required for the p27 to be ubiquitinated. It would appear that incubating the p27 with additional CDK2/Cyclin E and ATP for 20 minutes would suffice to ensure good phosphorylation.

ECL Format—E3 Ubiquitin Ligase Assay

Continuing with the E3 assay optimisation, p27 and E2 titrations were carried out using multiple tagging options on the E2 and p27 proteins.

The results indicate that the optimum signal was achieved when pairing the HA-E2 with the c-Myc-p27. This combination was used for all further E3 assay optimisation experiments.

Titrating the p27 against the E2 enzymes indicates an optimal signal strength at 1 μM E2 and 50 nM p27 (FIG. 21).

Following the identification of the optimum 'tag' pairing, an E1 vs. E2 checkerboard titration was performed in order to identify the optimum conditions for these assay components (FIG. 22).

E1—Hyperbolic increase in signal with increasing E1 concentration with a signal plateau after 25 nM. However, due to the relatively high non-specific signal which originates from the E1 enzyme (LB1805p12-15) the signal to background (No E2 background) ratio was taken into consideration when identifying a final assay concentration for the E1 enzyme in the E3 assay. The maximum signal to background is seen between 3.125 and 12.5 nM E1. Final assay concentration of E1 set at 5 nM.

E2—Approximately linear increase in signal with increasing E2 concentration. Unlike the E1 enzyme, non-specific binding is not a problem (LB1805p35-37). Although it appears that the signal will continue to increase with increasing E2 concentration, in the interests of minimising the total amount of protein and the assay costs, the E2 concentration was set at 1 μM.

Continuing with the E3 assay component optimization, ubiquitin and ATP titrations were performed to identify saturating, or at least non-rate limiting, conditions (FIGS. 23 (a) and (b)).

For each concentration of ATP tested, a hyperbolic increase in signal with increasing ubiquitin concentration was observed, with a signal plateau after approximately 2 μM. Fitting the data to a hyperbolic function generated apparent $K_M$ values for ubiquitin binding at multiple ATP concentrations. All of the apparent $K_M$ values were between 0.46 and 0.58 μM ubiquitin.

The initial titration of ATP at multiple concentrations of ubiquitin demonstrated a high signal which was independent of ATP concentration (LB1805p80-83). A repeat of this experiment using lower concentrations of ATP(LB1805p87-89) again showed a signal largely independent of ATP concentration with only a moderate decrease at 7 μM ATP. The apparent $K_M$ value was estimated at 4 μM.

Final assay concentrations were set at 2 μM ubiquitin and 100 μM ATP.

Next, the E3 components Skp1/Skp2/Cul1/Rbx1 and Cks1 were titrated together (FIG. 24). The concentration of the E3 tetramer (Skp1/Skp2/Cul1/Rbx1) was set according to the concentration of the component which was least prevalent in the co-expression (Skp2). The Cks1 concentration was set as equimolar to the concentration of the component which was least prevalent in the co-expression (Skp2).

A hyperbolic increase in signal with increasing E3/Cks1 concentration was observed, with a signal plateau after 50 nM. Re-plotting the data from 0 to 25 nM E3/Cks1 indicates a linear relationship between the signal and the E3/Cks1 concentration. Although the maximum signal is observed at 50 nM E3/Cks 1, a final assay concentration of 25 nM was chosen to ensure that the assay was within the linear region.

Finally, the Cks1 component was titrated against a fixed concentration of the E3 tetramer (25 nM). A hyperbolic increase in signal with increasing Cks1 concentration was observed, with a signal plateau after 50 nM. Although the maximum signal is observed at 50 nM Cks1, a final assay concentration of 25 nM was chosen to ensure the assay is within the linear range (FIG. 25).

Table 1 shows the final 'live' $SCF^{Skp2/Cks1}$ ECL assay concentrations.

TABLE 1

Final 'live' $SCF^{Skp2/Cks1}$ ECL assay concentrations

| Component | Final Assay Concentration | Reference |
|---|---|---|
| 6His-UBE1-(hu,FL) (E1) | 5 nM | LB1805p71-73 |
| HA,6His-UbcH3-(hu,FL) (E2) | 1 μM | LB1805p71-73 |
| c-Myc Phospho-p27-(hu,FL) co-expressed with UT-CDK2-(hu,FL), 6His-Cyclin E1-(hu,FL), | 25 nM | LB1805p53-57 |
| 6His-Skp2-(isoform 1, hu,FL), GST-Skp1-(hu,FL), 6His-Cul1-(hu,FL), UT-Rbx1-(hu,FL) (E3 tetramer) | 25 nM | LB1805p84-86 |
| 6His-Cks1-(hu,FL) | 25 nM | LB1805p112-113 |
| ATP | 100 μM | LB1805p87-89 |
| Biotinylated Ubiquitin | 2 μM | LB1805p80-83 |

Trialling Different E3 Co-expressions

The preceding E3 experiments were all carried out using an E3 comprised of a Skp1/Skp2/Cul1/Rbx1 tetramer alongside Cks1. Several other co-expressions were also available. Both a Skp1/Skp2 and a Cul1/Rbx1 co-expression were available with sufficient purity/yield to be used in an assay. A titration of these 2 components against each other was carried out in comparison to the tetramer co-expression. The concentration of the Skp1/Skp2 or Cul1/Rbx1 was set according to the concentration of the component which was least prevalent. The optimum conditions were seen at 25 nM Skp1/Skp2, 50 nM Cul1/Rbx1 in the presence of 25 nM Cks1. The comparison of the Skp1/Skp2 with Cul1/Rbx1 co-expressions against the Skp1/Skp2/Cul1/Rbx1 tetramer showed a largely similar max signal strength (FIG. 26). As all the previous experiments were carried out using the tetramer it was decided that all remaining assay development should be completed using the tetramer. Depending on the expression levels, yields and purities of the different co-expressions, this approach offers an alternative approach.

Comparison of the Skp1/Skp2 and Cul1/Rbx1 co-expressions with the Skp1/Skp2/Cul1/Rbx1 tetramer indicates very little difference in max signal strength. The tetramer was used for future experiments for ease of use and to corroborate with previous data (FIG. 27).

Time-course Assays

Following the identification of optimal conditions for all of the assay components, a time-course (0-100 minutes) was carried out to determine a linear part of the reaction velocity curve to set for future inhibitor work (FIG. 28). The experiment was performed on 2 different days to check the reproducibility of the data. In both experiments, a comparable and an approximately linear relationship is observed between the reaction time and the signal strength. The reaction time for future experiments was set at 60 minutes. It is evident that the data does not pass through the origin as would be expected but intercepts the y-axis. This may be a result of the 'stop' method. The assay stop contains EDTA which sequesters metal ions and hence prevents the Mg-ATP complex necessary for E1 function. However, the relatively large amount of E2 present means that even after the E1 has been halted, there may still be some ubiquitinated E2 present capable of p27 biotinylation leading to a 'lag' period after the stop has been added and an artificially high signal at each time point.

In order to assess the reproducibility of the final assay conditions, a Z' assay was carried out (FIG. 29)—64 wells (1 sector) of positive controls and 64 wells of negative (no ubiquitin) controls. The experiment was performed 3 different times to assess the reproducibility of the data. In each case the signal strength, signal/background ratio, positive control % CV and Z' values were within acceptable limits (Z'>0.6 (Zhang, Ji-Hu, Journal of Biomolecular Screening, Vol. 4, No. 2, 67-73 (1999)), % CV<15%).

Inhibitor Studies

Each of the assays in the p27 ubiquitination cascade (E1, E2 and E3) were tested against the E1 inhibitor PYR-41. No pre-charging of either the E1 or E2 was carried out prior to the introduction of the compound although in the E3 assay, p27 phosphorylation by CDK2/Cyclin E was carried out in the absence of inhibitor.

$IC_{50}$ values of 7.8 and 3.2 µM were generated for the E1 and E2 assays respectively—Comparable to the reported value of ~5 µM (Calbiochem). However, a significantly less potent $IC_{50}$ of 55 µM was seen for the E3 assay (FIGS. 30 (a) and (b)).

In order to test the feasibility of screening the E3 assay against a range of inhibitors, the assay was tested against a panel of 41 inhibitors (40 known kinase inhibitors and PYR-41) (FIG. 31). As expected, the PYR-41 showed a high degree of inhibition (>80%), and several other inhibitors also indicated moderate amounts of inhibition (Rottlerin, EGCG and K252c) (FIGS. 32 and 33). Using the same assay conditions, the E3 assay was tested against these inhibitors (FIG. 33). Both the Rottlerin and the EGCG inhibitors give $IC_{50}$ values in the µM range. The K252c inhibitor would appear to be a false positive result. One potential concern was that the inhibition was the result of inhibition of the CDK2/Cyclin E (and hence phosphorylation of the p27), despite the fact that phosphorylation was carried out in the absence of inhibitor. Comparison of the inhibition profiles for both the E3 assay and Cdk2/Cyclin E shows that this is not the case (FIG. 34).

Non-specific Binding Assays

Non-specific binding has previously been identified as a potential problem for both the biotinylated-ubiquitin on its own and for the E1 enzyme in the E2 assay. The NSB signal for the ubiquitin was minimized by limiting the amount of ubiquitin in the assay to 2 µM. Similarly, limiting the concentration of E1 enzyme in both the E2 and E3 assays to 5 nM allows decent E2 specific signal whilst reducing the non-specific signal from the E1 (FIG. 35).

Similar experiments have shown that non-specific binding signal is not a problem in the E2 assay. This indicates that under the E2 assay conditions neither the E2 (at any concentration), E1 (at 5 nM) or the ubiquitin (at 2 µM) contributes to a non-specific signal (FIG. 36).

Similar experiments have also been carried out for the E3 assay (FIG. 37). We again see a non-specific signal. However, our previous experiments have indicated that this signal is not the result of the E1 (at 5 nM), the ubiquitin (at 2 µM) or the E2 at any concentration. We must infer therefore that the NSB signal is the result of NSB from either the E3 or from the p27 complex. Further experiments have indicated that it is likely to be NSB of the p27 substrate itself. As a result, the non-specific signal is not an issue when testing the E3 assay.

Multiple approaches have been employed to minimize the proportion of non-specific signal (FIG. 38).

The invention claimed is:

1. A method of assaying ubiquitination in a sample comprising:
   (a) combining ubiquitin together with a substrate in a sample under conditions suitable for ubiquitination to take place and in the presence of a solid surface, wherein the sample includes the following components: UBE1; UbcH3; Skp2-isoform 1; Skp1; Cul1; Rbx1; Cks1; CDK2; and Cyclin E1, wherein each of the components and the substrate comprise an immobilisation tag which facilitates immobilisation of the substrate or component onto the solid surface, wherein each immobilisation tag is different, and wherein the Skp2-isoform 1 has the sequence comprising SEQ ID NO:3;
   (b) exposing the sample to a labeled binding partner which is specific for the ubiquitin; and
   (c) measuring the amount of labeled ubiquitin bound to any one of the substrate and components in the sample;
   wherein step (c) is performed two or more times in a single assay in order to measure the amount of labeled ubiquitin bound to two or more of the substrate and components in the sample, wherein each of the measured substrate and measured components are separated by being immobilized on the solid surface and the level of ubiquitination of two or more of the substrate and components can be measured simultaneously and/or sequentially to determine the amount of labeled ubiquitin bound to two or more of the measured substrate and measured components in the sample without changing the assay composition.

2. The method according to claim 1, wherein step (a) further comprises combining a potential modulator of ubiquitination.

3. The method according to claim 1, wherein the substrate, CDK2 and Cyclin E1 are combined prior to combination with the other components of (a).

4. The method of claim 1, wherein the substrate is P27.

5. The method of claim 1, wherein the UbcH3 is present at a final concentration between 750-1250 nM.

6. The method of claim 1, wherein measuring the amount of labeled ubiquitin bound to the substrate comprises Western blot analysis, Homogenous Time Resolved Fluorescence (HTRF), or electrochemiluminescence (ECL).

7. The method according to claim 1, wherein the UBE1 is added to a final concentration of 3-7 nM.

8. The method according to claim 1, wherein the Cks1 is added to a final concentration of 20-30 nM.

9. The method according to claim 1, wherein the CDK2 is added to a final concentration of 20-30 nM.

10. The method according to claim 1, wherein the Cyclin E1 is added to a final concentration of 20-30 nM.

11. The method according to claim 1, wherein the ubiquitin comprises a tag.

12. The method according to claim 11, wherein the ubiquitin tag is capable of interacting with the labeled binding partner to produce a detectable signal.

13. The method according to claim 12, wherein the ubiquitin tag and labeled binding partner form a FRET pair.

14. The method according to claim 1, wherein any one of the components and/or the substrate of (a) are immobilised on the solid surface.

15. The method according to claim 14, wherein the solid surface is an electrode.

16. The method according to claim 14 which comprises an additional wash step, (b'), which occurs between steps (b) and (c) and removes unbound components or substrate from the solid surface.

17. The method according to claim 1, wherein the Skp2 isoform 1, Skp1, Cul1 and Rbx1 are combined prior to combination with the other components of (a).

18. The method according to claim 17, wherein the Skp2-isoform 1, Skp1, Cul1 and Rbx1 are added as a tetramer to a final concentration of 20-30 nM.

19. The method according to claim 1, wherein step (a) further comprises combining ATP.

20. The method according to claim 19, wherein the ATP is added to a final concentration of 75-125 μM.

* * * * *

SEQUENCE LISTING

```
<160> NUMBER OF SEQ ID NOS: 18

<210> SEQ ID NO 1
<211> LENGTH: 1058
<212> TYPE: PRT
<213> ORGANISM: Homo sapiens

<400> SEQUENCE: 1

Met Ser Ser Ser Pro Leu Ser Lys Lys Arg Arg Val Ser Gly Pro Asp
1               5                   10                  15
```

```
Pro Lys Pro Gly Ser Asn Cys Ser Pro Ala Gln Ser Val Leu Ser Glu
            20                  25                  30
Val Pro Ser Val Pro Thr Asn Gly Met Ala Lys Asn Gly Ser Glu Ala
            35                  40                  45
Asp Ile Asp Glu Gly Leu Tyr Ser Arg Gln Leu Tyr Val Leu Gly His
    50                  55                      60
Glu Ala Met Lys Arg Leu Gln Thr Ser Ser Val Leu Val Ser Gly Leu
65                  70                  75                  80
Arg Gly Leu Gly Val Glu Ile Ala Lys Asn Ile Ile Leu Gly Gly Val
                85                  90                  95
Lys Ala Val Thr Leu His Asp Gln Gly Thr Ala Gln Trp Ala Asp Leu
            100                 105                 110
Ser Ser Gln Phe Tyr Leu Arg Glu Glu Asp Ile Gly Lys Asn Arg Ala
            115                 120                 125
Glu Val Ser Gln Pro Arg Leu Ala Glu Leu Asn Ser Tyr Val Pro Val
            130                 135                 140
Thr Ala Tyr Thr Gly Pro Leu Val Glu Asp Phe Leu Ser Gly Phe Gln
145                 150                 155                 160
Val Val Val Leu Thr Asn Thr Pro Leu Glu Asp Gln Leu Arg Val Gly
                165                 170                 175
Glu Phe Cys His Asn Arg Gly Ile Lys Leu Val Val Ala Asp Thr Arg
            180                 185                 190
Gly Leu Phe Gly Gln Leu Phe Cys Asp Phe Gly Glu Glu Met Ile Leu
            195                 200                 205
Thr Asp Ser Asn Gly Glu Gln Pro Leu Ser Ala Met Val Ser Met Val
210                 215                 220
Thr Lys Asp Asn Pro Gly Val Val Thr Cys Leu Asp Glu Ala Arg His
225                 230                 235                 240
Gly Phe Glu Ser Gly Asp Phe Val Ser Phe Ser Glu Val Gln Gly Met
                245                 250                 255
Val Glu Leu Asn Gly Asn Gln Pro Met Glu Ile Lys Val Leu Gly Pro
            260                 265                 270
Tyr Thr Phe Ser Ile Cys Asp Thr Ser Asn Phe Ser Asp Tyr Ile Arg
            275                 280                 285
Gly Gly Ile Val Ser Gln Val Lys Val Pro Lys Lys Ile Ser Phe Lys
290                 295                 300
Ser Leu Val Ala Ser Leu Ala Glu Pro Asp Phe Val Val Thr Asp Phe
305                 310                 315                 320
Ala Lys Phe Ser Arg Pro Ala Gln Leu His Ile Gly Phe Gln Ala Leu
            325                 330                 335
His Gln Phe Cys Ala Gln His Gly Arg Pro Pro Arg Pro Arg Asn Glu
            340                 345                 350
Glu Asp Ala Ala Glu Leu Val Ala Leu Ala Gln Ala Val Asn Ala Arg
            355                 360                 365
Ala Leu Pro Ala Val Gln Gln Asn Asn Leu Asp Glu Asp Leu Ile Arg
            370                 375                 380
Lys Leu Ala Tyr Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Val Leu Thr Glu Asp Lys Cys Leu Gln Arg Gln
```

```
            435                 440                 445
Asn Arg Tyr Asp Gly Gln Val Ala Val Phe Gly Ser Asp Leu Gln Glu
450                 455                 460
Lys Leu Gly Lys Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Gly Glu
                485                 490                 495
Gly Gly Glu Ile Ile Val Thr Asp Met Asp Thr Ile Glu Lys Ser Asn
                500                 505                 510
Leu Asn Arg Gln Phe Leu Phe Arg Pro Trp Asp Val Thr Lys Leu Lys
                515                 520                 525
Ser Asp Thr Ala Ala Ala Val Arg Gln Met Asn Pro His Ile Arg
530                 535                 540
Val Thr Ser His Gln Asn Arg Val Gly Pro Asp Thr Glu Arg Ile Tyr
545                 550                 555                 560
Asp Asp Asp Phe Phe Gln Asn Leu Asp Gly Val Ala Asn Ala Leu Asp
                565                 570                 575
Asn Val Asp Ala Arg Met Tyr Met Asp Arg Arg Cys Val Tyr Tyr Arg
                580                 585                 590
Lys Pro Leu Leu Glu Ser Gly Thr Leu Gly Thr Lys Gly Asn Val Gln
                595                 600                 605
Val Val Ile Pro Phe Leu Thr Glu Ser Tyr Ser Ser Ser Gln Asp Pro
610                 615                 620
Pro Glu Lys Ser Ile Pro Ile Cys Thr Leu Lys Asn Phe Pro Asn Ala
625                 630                 635                 640
Ile Glu His Thr Leu Gln Trp Ala Arg Asp Glu Phe Glu Gly Leu Phe
                645                 650                 655
Lys Gln Pro Ala Glu Asn Val Asn Gln Tyr Leu Thr Asp Pro Lys Phe
                660                 665                 670
Val Glu Arg Thr Leu Arg Leu Ala Gly Thr Gln Pro Leu Glu Val Leu
                675                 680                 685
Glu Ala Val Gln Arg Ser Leu Val Leu Gln Arg Pro Gln Thr Trp Ala
                690                 695                 700
Asp Cys Val Thr Trp Ala Cys His His Trp His Thr Gln Tyr Ser Asn
705                 710                 715                 720
Asn Ile Arg Gln Leu Leu His Asn Phe Pro Pro Asp Gln Leu Thr Ser
                725                 730                 735
Ser Gly Ala Pro Phe Trp Ser Gly Pro Lys Arg Cys Pro His Pro Leu
                740                 745                 750
Thr Phe Asp Val Asn Asn Pro Leu His Leu Asp Tyr Val Met Ala Ala
                755                 760                 765
Ala Asn Leu Phe Ala Gln Thr Tyr Gly Leu Thr Gly Ser Gln Asp Arg
                770                 775                 780
Ala Ala Val Ala Thr Phe Leu Gln Ser Val Gln Val Pro Glu Phe Thr
785                 790                 795                 800
Pro Lys Ser Gly Val Lys Ile His Val Ser Asp Gln Glu Leu Gln Ser
                805                 810                 815
Ala Asn Ala Ser Val Asp Asp Ser Arg Leu Glu Glu Leu Lys Ala Thr
                820                 825                 830
Leu Pro Ser Pro Asp Lys Leu Pro Gly Phe Lys Met Tyr Pro Ile Asp
                835                 840                 845
Phe Glu Lys Asp Asp Asp Ser Asn Phe His Met Asp Phe Ile Val Ala
850                 855                 860
```

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
        995                 1000                1005

Glu Arg Leu Asp Gln Pro Met Thr Glu Ile Val Ser Arg Val Ser
    1010                1015                1020

Lys Arg Lys Leu Gly Arg His Val Arg Ala Leu Val Leu Glu Leu
    1025                1030                1035

Cys Cys Asn Asp Glu Ser Gly Glu Asp Val Glu Val Pro Tyr Val
    1040                1045                1050

Arg Tyr Thr Ile Arg
    1055

<210> SEQ ID NO 2
<211> LENGTH: 236
<212> TYPE: PRT
<213> ORGANISM: Homo sapiens

<400> SEQUENCE: 2

Met Ala Arg Pro Leu Val Pro Ser Ser Gln Lys Ala Leu Leu Leu Glu
1               5                   10                  15

Leu Lys Gly Leu Gln Glu Glu Pro Val Glu Gly Phe Arg Val Thr Leu
            20                  25                  30

Val Asp Glu Gly Asp Leu Tyr Asn Trp Glu Val Ala Ile Phe Gly Pro
        35                  40                  45

Pro Asn Thr Tyr Tyr Glu Gly Gly Tyr Phe Lys Ala Arg Leu Lys Phe
    50                  55                  60

Pro Ile Asp Tyr Pro Tyr Ser Pro Pro Ala Phe Arg Phe Leu Thr Lys
65                  70                  75                  80

Met Trp His Pro Asn Ile Tyr Glu Thr Gly Asp Val Cys Ile Ser Ile
                85                  90                  95

Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Leu Leu Asn Glu Pro Asn Thr Phe Ser Pro Ala Asn Val Asp Ala
    130                 135                 140

Ser Val Met Tyr Arg Lys Trp Lys Glu Ser Lys Gly Lys Asp Arg Glu
145                 150                 155                 160

Tyr Thr Asp Ile Ile Arg Lys Gln Val Leu Gly Thr Lys Val Asp Ala

```
                165                 170                 175
Glu Arg Asp Gly Val Lys Val Pro Thr Thr Leu Ala Glu Tyr Cys Val
            180                 185                 190

Lys Thr Lys Ala Pro Ala Pro Asp Glu Gly Ser Asp Leu Phe Tyr Asp
        195                 200                 205

Asp Tyr Tyr Glu Asp Gly Glu Val Glu Glu Glu Ala Asp Ser Cys Phe
    210                 215                 220

Gly Asp Asp Glu Asp Asp Ser Gly Thr Glu Glu Ser
225                 230                 235

<210> SEQ ID NO 3
<211> LENGTH: 424
<212> TYPE: PRT
<213> ORGANISM: Homo sapiens

<400> SEQUENCE: 3

Met His Arg Lys His Leu Gln Glu Ile Pro Asp Leu Ser Ser Asn Val
1               5                  10                  15

Ala Thr Ser Phe Thr Trp Gly Trp Asp Ser Ser Lys Thr Ser Glu Leu
            20                  25                  30

Leu Ser Gly Met Gly Val Ser Ala Leu Glu Lys Glu Glu Pro Asp Ser
        35                  40                  45

Glu Asn Ile Pro Gln Glu Leu Leu Ser Asn Leu Gly His Pro Glu Ser
    50                  55                  60

Pro Pro Arg Lys Arg Leu Lys Ser Lys Gly Ser Asp Lys Asp Phe Val
65                  70                  75                  80

Ile Val Arg Arg Pro Lys Leu Asn Arg Glu Asn Phe Pro Gly Val Ser
                85                  90                  95

Trp Asp Ser Leu Pro Asp Glu Leu Leu Leu Gly Ile Phe Ser Cys Leu
            100                 105                 110

Cys Leu Pro Glu Leu Leu Lys Val Ser Gly Val Cys Lys Arg Trp Tyr
        115                 120                 125

Arg Leu Ala Ser Asp Glu Ser Leu Trp Gln Thr Leu Asp Leu Thr Gly
    130                 135                 140

Lys Asn Leu His Pro Asp Val Thr Gly Arg Leu Leu Ser Gln Gly Val
145                 150                 155                 160

Ile Ala Phe Arg Cys Pro Arg Ser Phe Met Asp Gln Pro Leu Ala Glu
                165                 170                 175

His Phe Ser Pro Phe Arg Val Gln His Met Asp Leu Ser Asn Ser Val
            180                 185                 190

Ile Glu Val Ser Thr Leu His Gly Ile Leu Ser Gln Cys Ser Lys Leu
        195                 200                 205

Gln Asn Leu Ser Leu Glu Gly Leu Arg Leu Ser Asp Pro Ile Val Asn
    210                 215                 220

Thr Leu Ala Lys Asn Ser Asn Leu Val Arg Leu Asn Leu Ser Gly Cys
225                 230                 235                 240

Ser Gly Phe Ser Glu Phe Ala Leu Gln Thr Leu Leu Ser Ser Cys Ser
                245                 250                 255

Arg Leu Asp Glu Leu Asn Leu Ser Trp Cys Phe Asp Phe Thr Glu Lys
            260                 265                 270

His Val Gln Val Ala Val Ala His Val Ser Glu Thr Ile Thr Gln Leu
        275                 280                 285

Asn Leu Ser Gly Tyr Arg Lys Asn Leu Gln Lys Ser Asp Leu Ser Thr
    290                 295                 300
```

```
Leu Val Arg Arg Cys Pro Asn Leu Val His Leu Asp Leu Ser Asp Ser
305                 310                 315                 320

Val Met Leu Lys Asn Asp Cys Phe Gln Glu Phe Phe Gln Leu Asn Tyr
            325                 330                 335

Leu Gln His Leu Ser Leu Ser Arg Cys Tyr Asp Ile Ile Pro Glu Thr
            340                 345                 350

Leu Leu Glu Leu Gly Glu Ile Pro Thr Leu Lys Thr Leu Gln Val Phe
            355                 360                 365

Gly Ile Val Pro Asp Gly Thr Leu Gln Leu Leu Lys Glu Ala Leu Pro
        370                 375                 380

His Leu Gln Ile Asn Cys Ser His Phe Thr Thr Ile Ala Arg Pro Thr
385                 390                 395                 400

Ile Gly Asn Lys Lys Asn Gln Glu Ile Trp Gly Ile Lys Cys Arg Leu
                405                 410                 415

Thr Leu Gln Lys Pro Ser Cys Leu
            420

<210> SEQ ID NO 4
<211> LENGTH: 160
<212> TYPE: PRT
<213> ORGANISM: Homo sapiens

<400> SEQUENCE: 4

Met Pro Ser Ile Lys Leu Gln Ser Ser Asp Gly Glu Ile Phe Glu Val
1               5                   10                  15

Asp Val Glu Ile Ala Lys Gln Ser Val Thr Ile Lys Thr Met Leu Glu
            20                  25                  30

Asp Leu Gly Met Asp Asp Glu Gly Asp Asp Pro Val Pro Leu Pro
            35                  40                  45

Asn Val Asn Ala Ala Ile Leu Lys Lys Val Ile Gln Trp Cys Thr His
        50                  55                  60

His Lys Asp Asp Pro Pro Pro Glu Asp Asp Glu Asn Lys Glu Lys
65                  70                  75                  80

Arg Thr Asp Asp Ile Pro Val Trp Asp Gln Glu Phe Leu Lys Val Asp
                85                  90                  95

Gln Gly Thr Leu Phe Glu Leu Ile Leu Ala Ala Asn Tyr Leu Asp Ile
            100                 105                 110

Lys Gly Leu Leu Asp Val Thr Cys Lys Thr Val Ala Asn Met Ile Lys
            115                 120                 125

Gly Lys Thr Pro Glu Glu Ile Arg Lys Thr Phe Asn Ile Lys Asn Asp
        130                 135                 140

Phe Thr Glu Glu Glu Glu Ala Gln Val Gly Ser Thr Gln Phe Cys Leu
145                 150                 155                 160

<210> SEQ ID NO 5
<211> LENGTH: 776
<212> TYPE: PRT
<213> ORGANISM: Homo sapiens

<400> SEQUENCE: 5

Met Ser Ser Thr Arg Ser Gln Asn Pro His Gly Leu Lys Gln Ile Gly
1               5                   10                  15

Leu Asp Gln Ile Trp Asp Asp Leu Arg Ala Gly Ile Gln Gln Val Tyr
            20                  25                  30

Thr Arg Gln Ser Met Ala Lys Ser Arg Tyr Met Glu Leu Tyr Thr His
            35                  40                  45
```

```
Val Tyr Asn Tyr Cys Thr Ser Val His Gln Ser Asn Gln Ala Arg Gly
 50                  55                  60
Ala Gly Val Pro Pro Ser Lys Ser Lys Gly Gln Thr Pro Gly Gly
 65                  70                  75                  80
Ala Gln Phe Val Gly Leu Glu Leu Tyr Lys Arg Leu Lys Glu Phe Leu
                 85                  90                  95
Lys Asn Tyr Leu Thr Asn Leu Leu Lys Asp Gly Glu Asp Leu Met Asp
            100                 105                 110
Glu Ser Val Leu Lys Phe Tyr Thr Gln Gln Trp Glu Asp Tyr Arg Phe
            115                 120                 125
Ser Ser Lys Val Leu Asn Gly Ile Cys Ala Tyr Leu Asn Arg His Trp
130                 135                 140
Val Arg Arg Glu Cys Asp Glu Gly Arg Lys Gly Ile Tyr Glu Ile Tyr
145                 150                 155                 160
Ser Leu Ala Leu Val Thr Trp Arg Asp Cys Leu Phe Arg Pro Leu Asn
                165                 170                 175
Lys Gln Val Thr Asn Ala Val Leu Lys Leu Ile Glu Lys Glu Arg Asn
            180                 185                 190
Gly Glu Thr Ile Asn Thr Arg Leu Ile Ser Gly Val Val Gln Ser Tyr
            195                 200                 205
Val Glu Leu Gly Leu Asn Glu Asp Asp Ala Phe Ala Lys Gly Pro Thr
210                 215                 220
Leu Thr Val Tyr Lys Glu Ser Phe Glu Ser Gln Phe Leu Ala Asp Thr
225                 230                 235                 240
Glu Arg Phe Tyr Thr Arg Glu Ser Thr Glu Phe Leu Gln Gln Asn Pro
                245                 250                 255
Val Thr Glu Tyr Met Lys Lys Ala Glu Ala Arg Leu Leu Glu Glu Gln
            260                 265                 270
Arg Arg Val Gln Val Tyr Leu His Glu Ser Thr Gln Asp Glu Leu Ala
            275                 280                 285
Arg Lys Cys Glu Gln Val Leu Ile Glu Lys His Leu Glu Ile Phe His
290                 295                 300
Thr Glu Phe Gln Asn Leu Leu Asp Ala Asp Lys Asn Glu Asp Leu Gly
305                 310                 315                 320
Arg Met Tyr Asn Leu Val Ser Arg Ile Gln Asp Gly Leu Gly Glu Leu
                325                 330                 335
Lys Lys Leu Leu Glu Thr His Ile His Asn Gln Gly Leu Ala Ala Ile
            340                 345                 350
Glu Lys Cys Gly Glu Ala Ala Leu Asn Asp Pro Lys Met Tyr Val Gln
            355                 360                 365
Thr Val Leu Asp Val His Lys Lys Tyr Asn Ala Leu Val Met Ser Ala
370                 375                 380
Phe Asn Asn Asp Ala Gly Phe Val Ala Ala Leu Asp Lys Ala Cys Gly
385                 390                 395                 400
Arg Phe Ile Asn Asn Ala Val Thr Lys Met Ala Gln Ser Ser Ser
                405                 410                 415
Lys Ser Pro Glu Leu Leu Ala Arg Tyr Cys Asp Ser Leu Leu Lys Lys
            420                 425                 430
Ser Ser Lys Asn Pro Glu Glu Ala Glu Leu Glu Asp Thr Leu Asn Gln
            435                 440                 445
Val Met Val Val Phe Lys Tyr Ile Glu Asp Lys Asp Val Phe Gln Lys
450                 455                 460
Phe Tyr Ala Lys Met Leu Ala Lys Arg Leu Val His Gln Asn Ser Ala
```

```
            465                 470                 475                 480

Ser Asp Asp Ala Glu Ala Ser Met Ile Ser Lys Leu Lys Gln Ala Cys
                    485                 490                 495

Gly Phe Glu Tyr Thr Ser Lys Leu Gln Arg Met Phe Gln Asp Ile Gly
                500                 505                 510

Val Ser Lys Asp Leu Asn Glu Gln Phe Lys Lys His Leu Thr Asn Ser
            515                 520                 525

Glu Pro Leu Asp Leu Asp Phe Ser Ile Gln Val Leu Ser Ser Gly Ser
        530                 535                 540

Trp Pro Phe Gln Gln Ser Cys Thr Phe Ala Leu Pro Ser Glu Leu Glu
545                 550                 555                 560

Arg Ser Tyr Gln Arg Phe Thr Ala Phe Tyr Ala Ser Arg His Ser Gly
                565                 570                 575

Arg Lys Leu Thr Trp Leu Tyr Gln Leu Ser Lys Gly Glu Leu Val Thr
                580                 585                 590

Asn Cys Phe Lys Asn Arg Tyr Thr Leu Gln Ala Ser Thr Phe Gln Met
            595                 600                 605

Ala Ile Leu Leu Gln Tyr Asn Thr Glu Asp Ala Tyr Thr Val Gln Gln
        610                 615                 620

Leu Thr Asp Ser Thr Gln Ile Lys Met Asp Ile Leu Ala Gln Val Leu
625                 630                 635                 640

Gln Ile Leu Leu Lys Ser Lys Leu Leu Val Leu Glu Asp Glu Asn Ala
                645                 650                 655

Asn Val Asp Glu Val Glu Leu Lys Pro Asp Thr Leu Ile Lys Leu Tyr
            660                 665                 670

Leu Gly Tyr Lys Asn Lys Lys Leu Arg Val Asn Ile Asn Val Pro Met
        675                 680                 685

Lys Thr Glu Gln Lys Gln Glu Gln Glu Thr Thr His Lys Asn Ile Glu
                690                 695                 700

Glu Asp Arg Lys Leu Leu Ile Gln Ala Ala Ile Val Arg Ile Met Lys
705                 710                 715                 720

Met Arg Lys Val Leu Lys His Gln Gln Leu Leu Gly Glu Val Leu Thr
                725                 730                 735

Gln Leu Ser Ser Arg Phe Lys Pro Arg Val Pro Val Ile Lys Lys Cys
                740                 745                 750

Ile Asp Ile Leu Ile Glu Lys Glu Tyr Leu Glu Arg Val Asp Gly Glu
            755                 760                 765

Lys Asp Thr Tyr Ser Tyr Leu Ala
        770                 775

<210> SEQ ID NO 6
<211> LENGTH: 108
<212> TYPE: PRT
<213> ORGANISM: Homo sapiens

<400> SEQUENCE: 6

Met Ala Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
                20                  25                  30

Trp Ala Trp Asp Ile Val Val Asp Asn Cys Ala Ile Cys Arg Asn His
            35                  40                  45

Ile Met Asp Leu Cys Ile Glu Cys Gln Ala Asn Gln Ala Ser Ala Thr
        50                  55                  60
```

-continued

```
Ser Glu Glu Cys Thr Val Ala Trp Gly Val Cys Asn His Ala Phe His
 65                  70                  75                  80

Phe His Cys Ile Ser Arg Trp Leu Lys Thr Arg Gln Val Cys Pro Leu
                 85                  90                  95

Asp Asn Arg Glu Trp Glu Phe Gln Lys Tyr Gly His
            100                 105
```

<210> SEQ ID NO 7
<211> LENGTH: 79
<212> TYPE: PRT
<213> ORGANISM: Homo sapiens

<400> SEQUENCE: 7

```
Met Ser His Lys Gln Ile Tyr Tyr Ser Asp Lys Tyr Asp Asp Glu Glu
 1               5                  10                  15

Phe Glu Tyr Arg His Val Met Leu Pro Lys Asp Ile Ala Lys Leu Val
                20                  25                  30

Pro Lys Thr His Leu Met Ser Glu Ser Glu Trp Arg Asn Leu Gly Val
            35                  40                  45

Gln Gln Ser Gln Gly Trp Val His Tyr Met Ile His Glu Pro Glu Pro
     50                  55                  60

His Ile Leu Leu Phe Arg Arg Pro Leu Pro Lys Pro Lys Lys
 65                  70                  75
```

<210> SEQ ID NO 8
<211> LENGTH: 298
<212> TYPE: PRT
<213> ORGANISM: Homo sapiens
<220> FEATURE:
<221> NAME/KEY: MOD_RES
<222> LOCATION: (37)..(37)
<223> OTHER INFORMATION: Any amino acid

<400> SEQUENCE: 8

```
Met Glu Asn Phe Gln Lys Val Glu Lys Ile Gly Glu Gly Thr Tyr Gly
 1               5                  10                  15

Val Val Tyr Lys Ala Arg Asn Lys Leu Thr Gly Glu Val Val Ala Leu
                20                  25                  30

Lys Lys Ile Arg Xaa Asp Thr Glu Thr Glu Gly Val Pro Ser Thr Ala
            35                  40                  45

Ile Arg Glu Ile Ser Leu Leu Lys Glu Leu Asn His Pro Asn Ile Val
     50                  55                  60

Lys Leu Leu Asp Val Ile His Thr Glu Asn Lys Leu Tyr Leu Val Phe
 65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
    115                 120                 125

Lys Pro Gln Asn Leu Leu Ile Asn Thr Glu Gly Ala Ile Lys Leu Ala
130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
            180                 185                 190
```

```
Phe Ala Glu Met Val Thr Arg Arg Ala Leu Phe Pro Gly Asp Ser Glu
            195                 200                 205

Ile Asp Gln Leu Phe Arg Ile Phe Arg Thr Leu Gly Thr Pro Asp Glu
    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
            260                 265                 270

Lys Arg Ile Ser Ala Lys Ala Ala Leu Ala His Pro Phe Phe Gln Asp
                275                 280                 285

Val Thr Lys Pro Val Pro His Leu Arg Leu
            290                 295

<210> SEQ ID NO 9
<211> LENGTH: 395
<212> TYPE: PRT
<213> ORGANISM: Homo sapiens

<400> SEQUENCE: 9

Met Lys Glu Asp Gly Gly Ala Glu Phe Ser Ala Arg Ser Arg Lys Arg
1               5                   10                  15

Lys Ala Asn Val Thr Val Phe Leu Gln Asp Pro Asp Glu Glu Met Ala
                20                  25                  30

Lys Ile Asp Arg Thr Ala Arg Asp Gln Cys Gly Ser Gln Pro Trp Asp
            35                  40                  45

Asn Asn Ala Val Cys Ala Asp Pro Cys Ser Leu Ile Pro Thr Pro Asp
        50                  55                  60

Lys Glu Asp Asp Asp Arg Val Tyr Pro Asn Ser Thr Cys Lys Pro Arg
65                  70                  75                  80

Ile Ile Ala Pro Ser Arg Gly Ser Pro Leu Pro Val Leu Ser Trp Ala
                85                  90                  95

Asn Arg Glu Glu Val Trp Lys Ile Met Leu Asn Lys Glu Lys Thr Tyr
                100                 105                 110

Leu Arg Asp Gln His Phe Leu Glu Gln His Pro Leu Leu Gln Pro Lys
            115                 120                 125

Met Arg Ala Ile Leu Leu Asp Trp Leu Met Glu Val Cys Glu Val Tyr
        130                 135                 140

Lys Leu His Arg Glu Thr Phe Tyr Leu Ala Gln Asp Phe Phe Asp Arg
145                 150                 155                 160

Tyr Met Ala Thr Gln Glu Asn Val Val Lys Thr Leu Leu Gln Leu Ile
                165                 170                 175

Gly Ile Ser Ser Leu Phe Ile Ala Ala Lys Leu Glu Glu Ile Tyr Pro
            180                 185                 190

Pro Lys Leu His Gln Phe Ala Tyr Val Thr Asp Gly Ala Cys Ser Gly
        195                 200                 205

Asp Glu Ile Leu Thr Met Glu Leu Met Ile Met Lys Ala Leu Lys Trp
    210                 215                 220

Arg Leu Ser Pro Leu Thr Ile Val Ser Trp Leu Asn Val Tyr Met Gln
225                 230                 235                 240

Val Ala Tyr Leu Asn Asp Leu His Glu Val Leu Leu Pro Gln Tyr Pro
                245                 250                 255

Gln Gln Ile Phe Ile Gln Ile Ala Glu Leu Leu Asp Leu Cys Val Leu
```

```
                    260                 265                 270
Asp Val Asp Cys Leu Glu Phe Pro Tyr Gly Ile Leu Ala Ala Ser Ala
            275                 280                 285

Leu Tyr His Phe Ser Ser Glu Leu Met Gln Lys Val Ser Gly Tyr
        290                 295                 300

Gln Trp Cys Asp Ile Glu Asn Cys Val Lys Trp Met Val Pro Phe Ala
305                 310                 315                 320

Met Val Ile Arg Glu Thr Gly Ser Ser Lys Lys His Phe Arg Gly
                325                 330                 335

Val Ala Asp Glu Asp Ala His Asn Ile Gln Thr His Arg Asp Ser Leu
            340                 345                 350

Asp Leu Leu Asp Lys Ala Arg Ala Lys Lys Ala Met Leu Ser Glu Gln
            355                 360                 365

Asn Arg Ala Ser Pro Leu Pro Ser Gly Leu Leu Thr Pro Pro Gln Ser
            370                 375                 380

Gly Lys Lys Gln Ser Ser Gly Pro Glu Met Ala
385                 390                 395

<210> SEQ ID NO 10
<211> LENGTH: 199
<212> TYPE: PRT
<213> ORGANISM: Homo sapiens

<400> SEQUENCE: 10

Met Ala Leu Asn Gly Ala Glu Val Asp Asp Phe Ser Trp Glu Pro Pro
1               5                   10                  15

Thr Glu Ala Glu Thr Lys Val Leu Gln Ala Arg Arg Glu Arg Gln Asp
            20                  25                  30

Arg Ile Ser Arg Leu Met Gly Asp Tyr Leu Leu Arg Gly Tyr Arg Met
        35                  40                  45

Leu Gly Glu Thr Cys Ala Asp Cys Gly Thr Ile Leu Leu Gln Asp Lys
    50                  55                  60

Gln Arg Lys Ile Tyr Cys Val Ala Cys Gln Glu Leu Asp Ser Asp Val
65                  70                  75                  80

Asp Lys Asp Asn Pro Ala Leu Asn Ala Gln Ala Ala Leu Ser Gln Ala
                85                  90                  95

Arg Glu His Gln Leu Ala Ser Ala Ser Glu Leu Pro Leu Gly Ser Arg
            100                 105                 110

Pro Ala Pro Gln Pro Pro Val Pro Arg Pro Glu His Cys Glu Gly Ala
        115                 120                 125

Ala Ala Gly Leu Lys Ala Ala Gln Gly Pro Pro Ala Pro Ala Val Pro
    130                 135                 140

Pro Asn Thr Asp Val Met Ala Cys Thr Gln Thr Ala Leu Leu Gln Lys
145                 150                 155                 160

Leu Thr Trp Ala Ser Ala Glu Leu Gly Ser Ser Thr Ser Leu Glu Thr
                165                 170                 175

Ser Ile Gln Leu Cys Gly Leu Ile Arg Ala Cys Ala Glu Ala Leu Arg
            180                 185                 190

Ser Leu Gln Gln Leu Gln His
        195

<210> SEQ ID NO 11
<211> LENGTH: 76
<212> TYPE: PRT
<213> ORGANISM: Homo sapiens
```

```
<400> SEQUENCE: 11

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 12
<211> LENGTH: 76
<212> TYPE: PRT
<213> ORGANISM: Mus musculus

<400> SEQUENCE: 12

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 13
<211> LENGTH: 76
<212> TYPE: PRT
<213> ORGANISM: Arabidopsis thaliana

<400> SEQUENCE: 13

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly
65                  70                  75

<210> SEQ ID NO 14
<211> LENGTH: 76
<212> TYPE: PRT
<213> ORGANISM: Saccharomyces cerevisiae

<400> SEQUENCE: 14

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45
```

Gln Leu Glu Asp Gly Arg Thr Leu Ser Asp Tyr Asn Ile Gln Lys Glu
            50                  55                  60

Ser Thr Leu His Leu Val Leu Arg Leu Arg Gly Gly
65                  70                  75

<210> SEQ ID NO 15
<211> LENGTH: 76
<212> TYPE: PRT
<213> ORGANISM: Drosophila melanogaster

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 16
<211> LENGTH: 76
<212> TYPE: PRT
<213> ORGANISM: Dictyostelium discoideum

<400> SEQUENCE: 16

Met Gln Ile Phe Val Lys Thr Leu Thr Gly Lys Thr Ile Thr Leu Glu
1               5                   10                  15

Val Glu Gly Ser Asp Asn Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 17
<211> LENGTH: 76
<212> TYPE: PRT
<213> ORGANISM: Bos taurus

<400> SEQUENCE: 17

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 18
<211> LENGTH: 53

```
<212> TYPE: PRT
<213> ORGANISM: Unknown
<220> FEATURE:
<223> OTHER INFORMATION: Description of Unknown: Rad23 protein
      sequence

<400> SEQUENCE: 18

Glu Gly Ser Phe Gln Val Asp Tyr Thr Pro Glu Asp Gln Ala Ile
1               5                   10                  15

Ser Arg Leu Ser Glu Leu Gly Phe Glu Arg Asp Leu Val Ile Gln Val
            20                  25                  30

Tyr Phe Ala Ser Asp Lys Asn Glu Glu Ala Ala Ala Asn Ile Leu Phe
        35                  40                  45

Ser Asp His Ala Asp
    50
```